(12) United States Patent
Thomas et al.

(10) Patent No.: US 12,390,418 B2
(45) Date of Patent: Aug. 19, 2025

(54) BIPHASIC COMPOSITIONS COMPRISING ONE OR BOTH OF CARBONATE AND PHOSPHATE

(71) Applicant: NATURAL EXTRACTION SYSTEMS, LLC, Boulder, CO (US)

(72) Inventors: C. Russell Thomas, Boulder, CO (US); Douglas G. Metcalf, Boulder, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

(21) Appl. No.: 18/700,209

(22) PCT Filed: Oct. 11, 2022

(86) PCT No.: PCT/US2022/046340
§ 371 (c)(1),
(2) Date: Apr. 10, 2024

(87) PCT Pub. No.: WO2023/064318
PCT Pub. Date: Apr. 20, 2023

(65) Prior Publication Data
US 2025/0009655 A1    Jan. 9, 2025

Related U.S. Application Data

(60) Provisional application No. 63/282,129, filed on Nov. 22, 2021, provisional application No. 63/256,461, filed on Oct. 15, 2021, provisional application No. 63/254,440, filed on Oct. 11, 2021.

(51) Int. Cl.
*A61K 9/10* (2006.01)
*A61K 9/00* (2006.01)
*A61K 9/16* (2006.01)
*A61K 31/00* (2006.01)

(52) U.S. Cl.
CPC .............. *A61K 9/10* (2013.01); *A61K 9/0095* (2013.01); *A61K 9/1611* (2013.01); *A61K 9/1623* (2013.01); *A61K 31/658* (2023.05)

(58) Field of Classification Search
None
See application file for complete search history.

(56) References Cited

U.S. PATENT DOCUMENTS 9,833,408 B1    12/2017   Greenspoon
10,555,914 B1*   2/2020   Metcalf .................... A23L 2/52
2021/0177739 A1  6/2021   Gerardi et al.

FOREIGN PATENT DOCUMENTS

WO    WO-2020123976 A1    6/2020

* cited by examiner

*Primary Examiner* — Robert A Wax
*Assistant Examiner* — William Craigo
(74) *Attorney, Agent, or Firm* — Douglas G. Metcalf

(57) ABSTRACT

Various aspects of this disclosure relate to biphasic compositions comprising one or both of solid-phase carbonate and solid-phase phosphate, which are capable of buffering a liquid phase to stabilize a liquid-phase anion.

9 Claims, No Drawings

BIPHASIC COMPOSITIONS COMPRISING ONE OR BOTH OF CARBONATE AND PHOSPHATE

CROSS-REFERENCE TO RELATED APPLICATIONS

This is a national phase application of International Application No. PCT/US2022/046340, filed Oct. 11, 2022, which claims priority to U.S. Provisional Patent Application No. 63/254,440, filed Oct. 11, 2021, U.S. Provisional Patent Application No. 63/256,461, filed Oct. 15, 2021, and U.S. Provisional Patent Application No. 63/282,129, filed Nov. 22, 2021, each of which is incorporated by reference in its entirety.

BACKGROUND

The "Rule of Five" states that a druglike agent generally has a common logarithm of its octanol-water partition coefficient that is no greater than 5. A generally-applicable strategy to overcome this limitation of the Rule of Five is desirable, and excipients that stabilize formulations that can overcome the limitation are also desirable.

SUMMARY

Various aspects of this disclosure relate to the discovery that solid-phase carbonate and phosphate salts can exchange cations for protons to buffer liquid phases in which the carbonate and phosphate salts lack robust solubility. The solid-phase carbonate or phosphate salts of a composition comprising a liquid phase can, for example, deprotonate a solute of the liquid phase to produce a weak base. The solid-phase carbonate and phosphate salts of a composition comprising a liquid phase can also, for example, inhibit the protonation of a weak base that is dissolved in the liquid phase. The solid-phase carbonate and phosphate salts of a composition comprising a liquid phase can also, for example, inhibit the protonation of a weak base after the composition is combined with an aqueous phase. These compositions are useful, for example, when a weak base anion displays one or both of improved compatibility with a desired formulation and improved pharmacokinetics relative to its conjugate acid, such as when the conjugate acid of the weak base lacks robust solubility in water. Such weak bases are described, for example, in PCT Patent Application Publication No. WO 2021/158575 A1. In some embodiments, a composition comprising a solid-phase buffer and a liquid-phase weak base is formulated as a biphasic powder for combination with an aqueous phase, such as a beverage, to facilitate the oral administration of one or both of the weak base and its conjugate acid.

The mechanism of cation/proton exchange is presently unknown, irrelevant to utility, and may include one or both of (i) partitioning a carbonate or phosphate salt into the liquid phase and partitioning a bicarbonate or hydrogen phosphate salt out of the liquid phase, and (ii) direct exchange of a cation for a proton at an interface between the solid phase and the liquid phase.

DETAILED DESCRIPTION

Various aspects of the disclosure relate to a composition, comprising each of a buffer, a conjugate acid, an excipient, an anion, and a solvent at both a concentration by mass and an amount by mole.

"Comprising" and "comprises" refer to open sets. A composition comprising a buffer, a conjugate acid, an excipient, an anion, and a solvent, for example, may also comprise one or more of a second excipient, a cosolvent, a molecule, and a cation.

In some embodiments, the buffer is carbonate.

In some embodiments, the buffer is a carbonate salt. In some specific embodiments, the buffer is sodium carbonate or potassium carbonate. In some very specific embodiments, the buffer is sodium carbonate.

In some embodiments, the buffer is phosphate.

In some embodiments, the buffer is a phosphate salt. In some specific embodiments, the buffer is trisodium phosphate or tripotassium phosphate. In some very specific embodiments, the buffer is trisodium phosphate.

In some embodiments, the conjugate acid is the conjugate acid of the buffer.

In some embodiments, the conjugate acid is bicarbonate.

In some embodiments, the conjugate acid is a bicarbonate salt. In some specific embodiments, the conjugate acid is sodium bicarbonate or potassium bicarbonate. In some very specific embodiments, the conjugate acid is sodium bicarbonate.

In some embodiments, the conjugate acid is hydrogen phosphate.

In some embodiments, the conjugate acid is a hydrogen phosphate salt. In some specific embodiments, the buffer is disodium phosphate or dipotassium phosphate. In some very specific embodiments, the buffer is disodium phosphate.

In some embodiments, the composition comprises the buffer and the conjugate acid at a combined concentration by mass of at least 0.05 percent and no greater than 2 percent.

In some embodiments, the concentration by mass of the excipient in the composition is greater than the combined concentration by mass of the buffer and the conjugate acid in the composition.

In some embodiments, the excipient comprises sugar alcohols. In some specific embodiments, the excipient comprises one or more of erythritol, threitol, arabitol, xylitol, ribitol, mannitol, sorbitol, galactitol, fucitol, iditol, inositol, and volemitol. In some even more specific embodiments, the excipient comprises one or more of erythritol, xylitol, mannitol, and sorbitol. In some very specific embodiments, the excipient comprises xylitol.

In some embodiments, the excipient consists of sugar alcohols. In some specific embodiments, the excipient consists of one or more of erythritol, threitol, arabitol, xylitol, ribitol, mannitol, sorbitol, galactitol, fucitol, iditol, inositol, and volemitol. In some even more specific embodiments, the excipient consists of one or more of erythritol, xylitol, mannitol, and sorbitol. In some very specific embodiments, the excipient consists of xylitol.

In some embodiments, the solvent is propylene glycol.

In some embodiments, the solvent is glycerol.

In some embodiments, the liquid phase comprises a cosolvent. In some specific embodiments, the liquid phase comprises a cosolvent; and the cosolvent is water.

In some embodiments, the concentration by mass of the solvent in the composition is greater than the concentration by mass of the anion in the composition.

In some embodiments, the composition comprises the buffer and the conjugate acid at a combined amount by mole that is greater than the amount by mole of the anion in the composition.

In some embodiments, the amount by mole of the solvent in the composition is at least 5 times greater than the amount by mole of the anion in the composition.

In some embodiments, the composition comprises the buffer and the conjugate acid at a ratio by mole of at least 1:800 and no greater than 80:1.

In some embodiments, the composition comprises a solid phase at a concentration of at least 88 percent and no greater than 98 percent by mass.

In some embodiments, the composition comprises a liquid phase at a concentration of at least 2 percent and no greater than 12 percent by mass.

In some embodiments, the solid phase and the liquid phase are in chemical communication such that the buffer, the conjugate acid, and excipient of the solid phase can dissolve into the liquid phase and such that the buffer, the conjugate acid, and excipient of the liquid phase can precipitate into the solid phase.

In some embodiments, the buffer has a solubility in the liquid phase, which is the maximum mass of the buffer that will dissolve in the liquid phase at thermodynamic equilibrium per volume of the liquid phase. In some embodiments, the conjugate acid has a solubility in the liquid phase, which is the maximum mass of the conjugate acid that will dissolve in the liquid phase at thermodynamic equilibrium per volume of the liquid phase. In some embodiments, the composition comprises one or both of (i) a mass-to-volume ratio of the buffer-to-liquid-phase that is greater than the solubility of the buffer in the liquid phase and (ii) a mass-to-volume ratio of the conjugate acid-to-liquid-phase that is greater than the solubility of the conjugate acid in the liquid phase.

In some embodiments, the excipient has a solubility in the liquid phase, which is the maximum mass of the excipient that will dissolve in the liquid phase at thermodynamic equilibrium per volume of the liquid phase. In some embodiments, the composition comprises a mass-to-volume ratio of excipient-to-liquid-phase that is greater than the solubility of the excipient in the liquid phase.

In some embodiments, each of the buffer, the conjugate acid, and the anion have an association constant for protonation in water at 20 degrees Celsius ("$K_{b,buffer}$", "$K_{b,conjugate\ acid}$", and "$K_{b,anion}$"). In some embodiments, the association constant for protonation of the anion is both greater than the association constant for protonation of the conjugate acid and less than the product of the association constant for protonation of the buffer and the ratio by mole of the buffer and the conjugate acid ($K_{b,conjugate\ acid} < K_{b,anion} < K_{b,buffer} \times$ ratio by mole of the buffer and the conjugate acid). In some specific embodiments, the association constant for protonation of the anion is both greater than 10 times the association constant for protonation of the conjugate acid and less than the product of the association constant for protonation of the buffer and the ratio by mole of the buffer and the conjugate acid ($10 \times K_{b,conjugate\ acid} < K_{b,anion} < K_{b,buffer} \times$ ratio by mole of the buffer and the conjugate acid). In some very specific embodiments, the association constant for protonation of the anion is both greater than 10 times the association constant for protonation of the conjugate acid and less than 10 percent of the product of the association constant for protonation of the buffer and the ratio by mole of the buffer and the conjugate acid ($10 \times K_{b,conjugate\ acid} < K_{b,anion} < 10\% \times K_{b,buffer} \times$ ratio by mole of the buffer and the conjugate acid). The association constant for protonation of carbonate in water at 20 degrees Celsius is approximately 210 micromolar, and the association constant for protonation of bicarbonate in water at 20 degrees Celsius is approximately 22 nanomolar. The association constant for protonation of phosphate in water at 20 degrees Celsius is approximately 23 millimolar, and the association constant for protonation of hydrogen phosphate in water at 20 degrees Celsius is approximately 160 nanomolar.

The term "ratio by mole of the buffer and the conjugate acid" refers to moles of the buffer divided by moles of the conjugate acid.

In some embodiments, the liquid phase comprises each of the anion and the solvent at both an amount by mass and an amount by mole.

In some embodiments, the amount by mass of the solvent in the liquid phase is greater than the amount by mass of the anion in the liquid phase.

In some embodiments, the amount by mole of the solvent in the liquid phase is at least 5 times greater than the amount by mole of the anion in the liquid phase.

In some embodiments, the liquid phase lacks each of the buffer, the conjugate acid, and the excipient at an amount by mole that is greater than the amount by mole of the solvent in the liquid phase.

In some embodiments, the solid phase lacks an amount by mass of the anion that is greater than the amount by mass of the anion in the liquid phase.

In some embodiments, the solid phase lacks an amount by mass of the solvent that is greater than the amount by mass of the solvent in the liquid phase.

In some embodiments, the solid phase comprises the excipient at an amount by mass.

In some embodiments, the solid phase comprises the buffer and the conjugate acid at a combined amount by mass that is less than the amount by mass of the excipient in the solid phase.

In some embodiments, and the liquid phase lacks an amount by mass of the excipient that is greater than the amount by mass of the excipient in the solid phase.

In some embodiments, the composition comprises the buffer and the conjugate acid at a combined concentration by mass of at least 0.1 percent. In some embodiments, the composition comprises the buffer and the conjugate acid at a combined concentration by mass of at least 0.2 percent. In some embodiments, the composition comprises the buffer and the conjugate acid at a combined concentration by mass of at least 0.4 percent. In some embodiments, the composition comprises the buffer and the conjugate acid at a combined concentration by mass of at least 0.6 percent. In some embodiments, the composition comprises the buffer and the conjugate acid at a combined concentration by mass of at least 0.8 percent. In some embodiments, the composition comprises the buffer and the conjugate acid at a combined concentration by mass of at least 1.0 percent.

In some embodiments, the composition comprises the buffer and the conjugate acid at a combined concentration by mass of no greater than 1.0 percent. In some embodiments, the composition comprises the buffer and the conjugate acid at a combined concentration by mass of no greater than 0.8 percent. In some embodiments, the composition comprises the buffer and the conjugate acid at a combined concentration by mass of no greater than 0.6 percent. In some embodiments, the composition comprises the buffer and the conjugate acid at a combined concentration by mass of no greater than 0.4 percent. In some embodiments, the composition comprises the buffer and the conjugate acid at a combined concentration by mass of no greater than 0.2 percent. In some embodiments, the composition comprises the buffer and the conjugate acid at a combined concentration by mass of no greater than 0.1 percent.

In some embodiments, the composition comprises a concentration by mass of the excipient that is at least 50 percent greater than the combined concentration by mass of the buffer and the conjugate acid in the composition. In some embodiments, the composition comprises a concentration by mass of the excipient that is at least 100 percent greater than the combined concentration by mass of the buffer and the conjugate acid in the composition. In some embodiments, the composition comprises a concentration by mass of the excipient that is at least 200 percent greater than the combined concentration by mass of the buffer and the conjugate acid in the composition. In some embodiments, the composition comprises a concentration by mass of the excipient that is at least 400 percent greater than the combined concentration by mass of the buffer and the conjugate acid in the composition. In some embodiments, the composition comprises a concentration by mass of the excipient that is at least 800 percent greater than the combined concentration by mass of the buffer and the conjugate acid in the composition. In some embodiments, the composition comprises a concentration by mass of the excipient that is at least 1600 percent greater than the combined concentration by mass of the buffer and the conjugate acid in the composition. In some embodiments, the composition comprises a concentration by mass of the excipient that is at least 3200 percent greater than the combined concentration by mass of the buffer and the conjugate acid in the composition. In some embodiments, the composition comprises a concentration by mass of the excipient that is at least 6400 percent greater than the combined concentration by mass of the buffer and the conjugate acid in the composition.

In some embodiments, the composition comprises a concentration by mass of the solvent that is at least 10 percent greater than the concentration by mass of the anion in the composition. In some embodiments, the composition comprises a concentration by mass of the solvent that is at least 20 percent greater than the concentration by mass of the anion in the composition. In some embodiments, the composition comprises a concentration by mass of the solvent that is at least 40 percent greater than the concentration by mass of the anion in the composition. In some embodiments, the composition comprises a concentration by mass of the solvent that is at least 80 percent greater than the concentration by mass of the anion in the composition. In some embodiments, the composition comprises a concentration by mass of the solvent that is at least 160 percent greater than the concentration by mass of the anion in the composition. In some embodiments, the composition comprises a concentration by mass of the solvent that is at least 320 percent greater than the concentration by mass of the anion in the composition. In some embodiments, the composition comprises a concentration by mass of the solvent that is at least 640 percent greater than the concentration by mass of the anion in the composition.

In some embodiments, the composition comprises a concentration by mole of the anion that is at least 20 percent of the concentration by mole of the conjugate acid in the composition. In some embodiments, the composition comprises a concentration by mole of the anion that is at least 40 percent of the concentration by mole of the conjugate acid in the composition. In some embodiments, the composition comprises a concentration by mole of the anion that is at least 60 percent of the concentration by mole of the conjugate acid in the composition. In some embodiments, the composition comprises a concentration by mole of the anion that is at least 80 percent of the concentration by mole of the conjugate acid in the composition.

In some embodiments, the composition comprises a concentration by mass of the anion that is at least 1 percent of the combined concentration by mass of the buffer and the conjugate acid in the composition. In some embodiments, the composition comprises a concentration by mass of the anion that is at least 2 percent of the combined concentration by mass of the buffer and the conjugate acid in the composition. In some embodiments, the composition comprises a concentration by mass of the anion that is at least 4 percent of the combined concentration by mass of the buffer and the conjugate acid in the composition. In some embodiments, the composition comprises a concentration by mass of the anion that is at least 8 percent of the combined concentration by mass of the buffer and the conjugate acid in the composition. In some embodiments, the composition comprises a concentration by mass of the anion that is at least 16 percent of the combined concentration by mass of the buffer and the conjugate acid in the composition. In some embodiments, the composition comprises a concentration by mass of the anion that is at least 32 percent of the combined concentration by mass of the buffer and the conjugate acid in the composition. In some embodiments, the composition comprises a concentration by mass of the anion that is at least 64 percent of the combined concentration by mass of the buffer and the conjugate acid in the composition.

In some embodiments, the composition comprises the buffer and the conjugate acid at a combined amount by mole that is at least 5 percent greater than the amount by mole of the anion in the composition. In some embodiments, the composition comprises the buffer and the conjugate acid at a combined amount by mole that is at least 10 percent greater than the amount by mole of the anion in the composition. In some embodiments, the composition comprises the buffer and the conjugate acid at a combined amount by mole that is at least 20 percent greater than the amount by mole of the anion in the composition. In some embodiments, the composition comprises the buffer and the conjugate acid at a combined amount by mole that is at least 40 percent greater than the amount by mole of the anion in the composition. In some embodiments, the composition comprises the buffer and the conjugate acid at a combined amount by mole that is at least 80 percent greater than the amount by mole of the anion in the composition.

In some embodiments, the amount by mole of the solvent in the composition is at least 10 times greater than the amount by mole of the anion in the composition. In some embodiments, the amount by mole of the solvent in the composition is at least 20 times greater than the amount by mole of the anion in the composition. In some embodiments, the amount by mole of the solvent in the composition is at least 40 times greater than the amount by mole of the anion in the composition.

In some embodiments, the composition comprises the buffer and the conjugate acid at a ratio by mole of at least 1:400. In some embodiments, the composition comprises the buffer and the conjugate acid at a ratio by mole of at least 1:200. In some embodiments, the composition comprises the buffer and the conjugate acid at a ratio by mole of at least 1:100. In some embodiments, the composition comprises the buffer and the conjugate acid at a ratio by mole of at least 1:50. In some embodiments, the composition comprises the buffer and the conjugate acid at a ratio by mole of at least 1:25. In some embodiments, the composition comprises the buffer and the conjugate acid at a ratio by mole of at least 1:10. In some embodiments, the composition comprises the buffer and the conjugate acid at a ratio by mole of at least 1:5. In some embodiments, the composition comprises the buffer and the conjugate acid at a ratio by mole of at least 1:2. In some embodiments, the composition comprises the buffer and the conjugate acid at a ratio by mole of at least 1:1. In some embodiments, the composition comprises the buffer and the conjugate acid at a ratio by mole of at least 2:1. In some embodiments, the composition comprises the buffer and the conjugate acid at a ratio by mole of at least 5:1.

In some embodiments, the composition comprises the buffer and the conjugate acid at a ratio by mole of no greater than 40:1. In some embodiments, the composition comprises the buffer and the conjugate acid at a ratio by mole of no greater than 20:1. In some embodiments, the composition comprises the buffer and the conjugate acid at a ratio by mole of no greater than 10:1. In some embodiments, the composition comprises the buffer and the conjugate acid at a ratio by mole of no greater than 5:1. In some embodiments, the composition comprises the buffer and the conjugate acid at a ratio by mole of no greater than 2:1. In some embodiments, the composition comprises the buffer and the conjugate acid at a ratio by mole of no greater than 1:1. In some embodiments, the composition comprises the buffer and the conjugate acid at a ratio by mole of no greater than 1:2. In some embodiments, the composition comprises the buffer and the conjugate acid at a ratio by mole of no greater than 1:5. In some embodiments, the composition comprises the buffer and the conjugate acid at a ratio by mole of no greater than 1:10. In some embodiments, the composition comprises the buffer and the conjugate acid at a ratio by mole of no greater than 1:25. In some embodiments, the composition comprises the buffer and the conjugate acid at a ratio by mole of no greater than 1:50. In some embodiments, the composition comprises the buffer and the conjugate acid at a ratio by mole of no greater than 1:100.

In some embodiments, the composition comprises the solid phase at a concentration of at least 90 percent by mass. In some embodiments, the composition comprises the solid phase at a concentration of at least 92 percent by mass. In some embodiments, the composition comprises the solid phase at a concentration of at least 94 percent by mass. In some embodiments, the composition comprises the solid phase at a concentration of at least 96 percent by mass.

In some embodiments, the composition comprises the solid phase at a concentration of no greater than 96 percent by mass. In some embodiments, the composition comprises the solid phase at a concentration of no greater than 94 percent by mass. In some embodiments, the composition comprises the solid phase at a concentration of no greater than 92 percent by mass. In some embodiments, the composition comprises the solid phase at a concentration of no greater than 90 percent by mass.

In some embodiments, the composition comprises the liquid phase at a concentration of at least 4 percent by mass. In some embodiments, the composition comprises the liquid phase at a concentration of at least 6 percent by mass. In some embodiments, the composition comprises the liquid phase at a concentration of at least 8 percent by mass. In some embodiments, the composition comprises the liquid phase at a concentration of at least 10 percent by mass.

In some embodiments, the composition comprises the liquid phase at a concentration of no greater than 10 percent by mass. In some embodiments, the composition comprises the liquid phase at a concentration of no greater than 8 percent by mass. In some embodiments, the composition comprises the liquid phase at a concentration of no greater than 6 percent by mass. In some embodiments, the composition comprises the liquid phase at a concentration of no greater than 4 percent by mass.

In some embodiments, the composition comprises a mass-to-volume ratio of the buffer-to-liquid-phase that is greater than the solubility of the buffer in the liquid phase. In some embodiments, the composition comprises a mass-to-volume ratio of the buffer-to-liquid-phase that is at least 10 percent greater than the solubility of the buffer in the liquid phase. In some embodiments, the composition comprises a mass-to-volume ratio of the buffer-to-liquid-phase that is at least 20 percent greater than the solubility of the buffer in the liquid phase. In some embodiments, the composition comprises a mass-to-volume ratio of the buffer-to-liquid-phase that is at least 40 percent greater than the solubility of the buffer in the liquid phase. In some embodiments, the composition comprises a mass-to-volume ratio of the buffer-to-liquid-phase that is at least 80 percent greater than the solubility of the buffer in the liquid phase. In some embodiments, the composition comprises a mass-to-volume ratio of the buffer-to-liquid-phase that is at least 160 percent greater than the solubility of the buffer in the liquid phase. In some embodiments, the composition comprises a mass-to-volume ratio of the buffer-to-liquid-phase that is at least 320 percent greater than the solubility of the buffer in the liquid phase. In some embodiments, the composition comprises a mass-to-volume ratio of the buffer-to-liquid-phase that is at least 640 percent greater than the solubility of the buffer in the liquid phase. In some embodiments, the composition comprises a mass-to-volume ratio of the buffer-to-liquid-phase that is at least 1280 percent greater than the solubility of the buffer in the liquid phase.

In some embodiments, the composition comprises a mass-to-volume ratio of the conjugate acid-to-liquid-phase that is greater than the solubility of the conjugate acid in the liquid phase. In some embodiments, the composition comprises a mass-to-volume ratio of the conjugate acid-to-liquid-phase that is at least 10 percent greater than the solubility of the conjugate acid in the liquid phase. In some embodiments, the composition comprises a mass-to-volume ratio of the conjugate acid-to-liquid-phase that is at least 20 percent greater than the solubility of the conjugate acid in the liquid phase. In some embodiments, the composition comprises a mass-to-volume ratio of the conjugate acid-to-liquid-phase that is at least 40 percent greater than the solubility of the conjugate acid in the liquid phase. In some embodiments, the composition comprises a mass-to-volume ratio of the conjugate acid-to-liquid-phase that is at least 80 percent greater than the solubility of the conjugate acid in the liquid phase. In some embodiments, the composition comprises a mass-to-volume ratio of the conjugate acid-to-liquid-phase that is at least 160 percent greater than the solubility of the conjugate acid in the liquid phase. In some embodiments, the composition comprises a mass-to-volume ratio of the conjugate acid-to-liquid-phase that is at least 320 percent greater than the solubility of the conjugate acid in the liquid phase. In some embodiments, the composition comprises a mass-to-volume ratio of the conjugate acid-to-liquid-phase that is at least 640 percent greater than the solubility of the conjugate acid in the liquid phase. In some embodiments, the composition comprises a mass-to-volume ratio of the conjugate acid-to-liquid-phase that is at least 1280 percent greater than the solubility of the conjugate acid in the liquid phase.

In some embodiments, the composition comprises a mass-to-volume ratio of excipient-to-liquid-phase that is at least 2 times greater than the solubility of the excipient in the liquid phase. In some embodiments, the composition comprises a mass-to-volume ratio of excipient-to-liquid-phase that is at least 4 times greater than the solubility of the excipient in the liquid phase. In some embodiments, the composition comprises a mass-to-volume ratio of excipient-to-liquid-phase that is at least 8 times greater than the solubility of the excipient in the liquid phase. In some embodiments, the composition comprises a mass-to-volume ratio of excipient-to-liquid-phase that is at least 16 times greater than the solubility of the excipient in the liquid phase. In some embodiments, the composition comprises a mass-to-volume ratio of excipient-to-liquid-phase that is at least 32 times greater than the solubility of the excipient in the liquid phase. In some embodiments, the composition comprises a mass-to-volume ratio of excipient-to-liquid-phase that is at least 64 times greater than the solubility of the excipient in the liquid phase. In some embodiments, the composition comprises a mass-to-volume ratio of excipient-to-liquid-phase that is at least 128 times greater than the solubility of the excipient in the liquid phase.

In some embodiments, the association constant for protonation of the anion is at least 20 times the association constant for protonation of the conjugate acid. In some embodiments, the association constant for protonation of the anion is at least 40 times the association constant for protonation of the conjugate acid. In some embodiments, the association constant for protonation of the anion is at least 60 times the association constant for protonation of the conjugate acid. In some embodiments, the association constant for protonation of the anion is at least 80 times the association constant for protonation of the conjugate acid.

In some embodiments, the association constant for protonation of the anion is less than 64 percent of the product of the association constant for protonation of the buffer and the ratio by mole of the buffer and the conjugate acid. In some embodiments, the association constant for protonation of the anion is less than 32 percent of the product of the association constant for protonation of the buffer and the ratio by mole of the buffer and the conjugate acid. In some embodiments, the association constant for protonation of the anion is less than 16 percent of the product of the association constant for protonation of the buffer and the ratio by mole of the buffer and the conjugate acid. In some embodiments, the association constant for protonation of the anion is less than 8 percent of the product of the association constant for protonation of the buffer and the ratio by mole of the buffer and the conjugate acid. In some embodiments, the association constant for protonation of the anion is less than 4 percent of the product of the association constant for protonation of the buffer and the ratio by mole of the buffer and the conjugate acid. In some embodiments, the association constant for protonation of the anion is less than 2 percent of the product of the association constant for protonation of the buffer and the ratio by mole of the buffer and the conjugate acid. In some embodiments, the association constant for protonation of the anion is less than 1 percent of the product of the association constant for protonation of the buffer and the ratio by mole of the buffer and the conjugate acid.

In some embodiments, the association constant for protonation of the anion is less than the association constant for protonation of the buffer. In some embodiments, the association constant for protonation of the anion is less than 64 percent of the association constant for protonation of the buffer. In some embodiments, the association constant for protonation of the anion is less than 32 percent of the association constant for protonation of the buffer. In some embodiments, the association constant for protonation of the anion is less than 16 percent of the association constant for protonation of the buffer. In some embodiments, the association constant for protonation of the anion is less than 8 percent of the association constant for protonation of the buffer. In some embodiments, the association constant for protonation of the anion is less than 4 percent of the association constant for protonation of the buffer. In some embodiments, the association constant for protonation of the anion is less than 2 percent of the association constant for protonation of the buffer. In some embodiments, the association constant for protonation of the anion is less than 1 percent of the association constant for protonation of the buffer.

In some embodiments, the amount by mass of the solvent in the liquid phase is at least 10 percent greater than the amount by mass of the anion in the liquid phase. In some embodiments, the amount by mass of the solvent in the liquid phase is at least 20 percent greater than the amount by mass of the anion in the liquid phase. In some embodiments, the amount by mass of the solvent in the liquid phase is at least 40 percent greater than the amount by mass of the anion in the liquid phase. In some embodiments, the amount by mass of the solvent in the liquid phase is at least 80 percent greater than the amount by mass of the anion in the liquid phase. In some embodiments, the amount by mass of the solvent in the liquid phase is at least 160 percent greater than the amount by mass of the anion in the liquid phase. In some embodiments, the amount by mass of the solvent in the liquid phase is at least 320 percent greater than the amount by mass of the anion in the liquid phase. In some embodiments, the amount by mass of the solvent in the liquid phase is at least 640 percent greater than the amount by mass of the anion in the liquid phase.

In some embodiments, the amount by mole of the solvent in the liquid phase is at least 10 times greater than the amount by mole of the anion in the liquid phase. In some embodiments, the amount by mole of the solvent in the liquid phase is at least 20 times greater than the amount by mole of the anion in the liquid phase. In some embodiments, the amount by mole of the solvent in the liquid phase is at least 30 times greater than the amount by mole of the anion in the liquid phase. In some embodiments, the amount by mole of the solvent in the liquid phase is at least 40 times greater than the amount by mole of the anion in the liquid phase.

In some embodiments, the liquid phase lacks the buffer at an amount by mole that is greater than 64 percent of the amount by mole of the solvent in the liquid phase. In some embodiments, the liquid phase lacks the buffer at an amount by mole that is greater than 32 percent of the amount by mole of the solvent in the liquid phase. In some embodiments, the liquid phase lacks the buffer at an amount by mole that is greater than 16 percent of the amount by mole of the solvent in the liquid phase. In some embodiments, the liquid phase lacks the buffer at an amount by mole that is greater than 8 percent of the amount by mole of the solvent in the liquid phase. In some embodiments, the liquid phase lacks the buffer at an amount by mole that is greater than 4 percent of the amount by mole of the solvent in the liquid phase. In some embodiments, the liquid phase lacks the buffer at an amount by mole that is greater than 2 percent of the amount by mole of the solvent in the liquid phase. In some embodiments, the liquid phase lacks the buffer at an amount by mole that is greater than 1 percent of the amount by mole of the solvent in the liquid phase.

In some embodiments, the liquid phase lacks the conjugate acid at an amount by mole that is greater than 64 percent of the amount by mole of the solvent in the liquid phase. In some embodiments, the liquid phase lacks the conjugate acid at an amount by mole that is greater than 32 percent of the amount by mole of the solvent in the liquid phase. In some embodiments, the liquid phase lacks the conjugate acid at an amount by mole that is greater than 16 percent of the amount by mole of the solvent in the liquid phase. In some embodiments, the liquid phase lacks the conjugate acid at an amount by mole that is greater than 8 percent of the amount by mole of the solvent in the liquid phase. In some embodiments, the liquid phase lacks the conjugate acid at an amount by mole that is greater than 4 percent of the amount by mole of the solvent in the liquid phase. In some embodiments, the liquid phase lacks the conjugate acid at an amount by mole that is greater than 2 percent of the amount by mole of the solvent in the liquid phase. In some embodiments, the liquid phase lacks the conjugate acid at an amount by mole that is greater than 1 percent of the amount by mole of the solvent in the liquid phase.

In some embodiments, the liquid phase lacks the excipient at an amount by mole that is greater than 64 percent of the amount by mole of the solvent in the liquid phase. In some embodiments, the liquid phase lacks the excipient at an amount by mole that is greater than 32 percent of the amount by mole of the solvent in the liquid phase. In some embodiments, the liquid phase lacks the excipient at an amount by mole that is greater than 16 percent of the amount by mole of the solvent in the liquid phase. In some embodiments, the liquid phase lacks the excipient at an amount by mole that is greater than 8 percent of the amount by mole of the solvent in the liquid phase. In some embodiments, the liquid phase lacks the excipient at an amount by mole that is greater than 4 percent of the amount by mole of the solvent in the liquid phase. In some embodiments, the liquid phase lacks the excipient at an amount by mole that is greater than 2 percent of the amount by mole of the solvent in the liquid phase. In some embodiments, the liquid phase lacks the excipient at an amount by mole that is greater than 1 percent of the amount by mole of the solvent in the liquid phase.

In some embodiments, the solid phase lacks an amount by mass of the anion that is greater than 80 percent of the amount by mass of the anion in the liquid phase. In some embodiments, the solid phase lacks an amount by mass of the anion that is greater than 60 percent of the amount by mass of the anion in the liquid phase. In some embodiments, the solid phase lacks an amount by mass of the anion that is greater than 40 percent of the amount by mass of the anion in the liquid phase. In some embodiments, the solid phase lacks an amount by mass of the anion that is greater than 20 percent of the amount by mass of the anion in the liquid phase. In some embodiments, the solid phase lacks an amount by mass of the anion that is greater than 10 percent of the amount by mass of the anion in the liquid phase.

In some embodiments, the solid phase lacks an amount by mass of the solvent that is greater than 80 percent of the amount by mass of the solvent in the liquid phase. In some embodiments, the solid phase lacks an amount by mass of the solvent that is greater than 60 percent of the amount by mass of the solvent in the liquid phase. In some embodiments, the solid phase lacks an amount by mass of the solvent that is greater than 40 percent of the amount by mass of the solvent in the liquid phase. In some embodiments, the solid phase lacks an amount by mass of the solvent that is greater than 20 percent of the amount by mass of the solvent in the liquid phase. In some embodiments, the solid phase lacks an amount by mass of the solvent that is greater than 10 percent of the amount by mass of the solvent in the liquid phase.

In some embodiments, the solid phase comprises the buffer and the conjugate acid at a combined amount by mass that is no greater than 64 percent of the amount by mass of the excipient in the solid phase. In some embodiments, the solid phase comprises the buffer and the conjugate acid at a combined amount by mass that is no greater than 32 percent of the amount by mass of the excipient in the solid phase. In some embodiments, the solid phase comprises the buffer and the conjugate acid at a combined amount by mass that is no greater than 16 percent of the amount by mass of the excipient in the solid phase. In some embodiments, the solid phase comprises the buffer and the conjugate acid at a combined amount by mass that is no greater than 8 percent of the amount by mass of the excipient in the solid phase. In some embodiments, the solid phase comprises the buffer and the conjugate acid at a combined amount by mass that is no greater than 4 percent of the amount by mass of the excipient in the solid phase. In some embodiments, the solid phase comprises the buffer and the conjugate acid at a combined amount by mass that is no greater than 2 percent of the amount by mass of the excipient in the solid phase.

In some embodiments, the liquid phase lacks an amount by mass of the excipient that is greater than 10 percent of the amount by mass of the excipient in the solid phase. In some embodiments, the liquid phase lacks an amount by mass of the excipient that is greater than 5 percent of the amount by mass of the excipient in the solid phase. In some embodiments, the liquid phase lacks an amount by mass of the excipient that is greater than 2 percent of the amount by mass of the excipient in the solid phase. In some embodiments, the liquid phase lacks an amount by mass of the excipient that is greater than 1 percent of the amount by mass of the excipient in the solid phase. In some embodiments, the liquid phase lacks an amount by mass of the excipient that is greater than 0.5 percent of the amount by mass of the excipient in the solid phase.

In some embodiments, the liquid phase lacks the buffer at an amount by mass that is greater than the amount by mass of the anion in the liquid phase.

In some embodiments, the liquid phase lacks the conjugate acid at an amount by mass that is greater than the amount by mass of the anion in the liquid phase.

In some embodiments, the liquid phase lacks the buffer and the conjugate acid at a combined amount by mass that is greater than the amount by mass of the anion in the liquid phase.

In some embodiments, the liquid phase lacks the buffer at an amount by mole that is greater than the amount by mole of the anion in the liquid phase.

In some embodiments, the liquid phase lacks the conjugate acid at an amount by mole that is greater than the amount by mole of the anion in the liquid phase.

In some embodiments, the liquid phase lacks the buffer and the conjugate acid at a combined amount by mole that is greater than the amount by mole of the anion in the liquid phase.

In some embodiments, the liquid phase lacks a combined amount by mole of the buffer and the conjugate acid that is greater than the combined amount by mole of the buffer and the conjugate acid in the solid phase. In some embodiments, the liquid phase lacks a combined amount by mole of the buffer and the conjugate acid that is greater than 64 percent of the combined amount by mole of the buffer and the conjugate acid in the solid phase. In some embodiments, the liquid phase lacks a combined amount by mole of the buffer and the conjugate acid that is greater than 32 percent of the combined amount by mole of the buffer and the conjugate acid in the solid phase. In some embodiments, the liquid phase lacks a combined amount by mole of the buffer and the conjugate acid that is greater than 16 percent of the combined amount by mole of the buffer and the conjugate acid in the solid phase. In some embodiments, the liquid phase lacks a combined amount by mole of the buffer and the conjugate acid that is greater than 8 percent of the combined amount by mole of the buffer and the conjugate acid in the solid phase.

In some embodiments, the liquid phase lacks an amount by mole of the buffer that is greater than the amount by mole of the buffer in the solid phase. In some embodiments, the liquid phase lacks an amount by mole of the buffer that is greater than 64 percent of the amount by mole of the buffer in the solid phase. In some embodiments, the liquid phase lacks an amount by mole of the buffer that is greater than 32 percent of the amount by mole of the buffer in the solid phase. In some embodiments, the liquid phase lacks an amount by mole of the buffer that is greater than 16 percent of the amount by mole of the buffer in the solid phase. In some embodiments, the liquid phase lacks an amount by mole of the buffer that is greater than 8 percent of the amount by mole of the buffer in the solid phase.

In some embodiments, the liquid phase lacks an amount by mole of the conjugate acid that is greater than the amount by mole of the conjugate acid in the solid phase. In some embodiments, the liquid phase lacks an amount by mole of the conjugate acid that is greater than 64 percent of the amount by mole of the conjugate acid in the solid phase. In some embodiments, the liquid phase lacks an amount by mole of the conjugate acid that is greater than 32 percent of the amount by mole of the conjugate acid in the solid phase. In some embodiments, the liquid phase lacks an amount by mole of the conjugate acid that is greater than 16 percent of the amount by mole of the conjugate acid in the solid phase. In some embodiments, the liquid phase lacks an amount by mole of the conjugate acid that is greater than 8 percent of the amount by mole of the conjugate acid in the solid phase.

In some embodiments, the composition comprises a gas phase in fluid communication with the liquid phase, wherein a container inhibits fluid communication between the liquid phase and any gas other than the gas phase.

In some embodiments, the composition comprises the gas phase at a concentration of no greater than 1 percent by mass. In some embodiments, the composition comprises the gas phase at a concentration of no greater than 0.8 percent by mass. In some embodiments, the composition comprises the gas phase at a concentration of no greater than 0.6 percent by mass. In some embodiments, the composition comprises the gas phase at a concentration of no greater than 0.4 percent by mass. In some embodiments, the composition comprises the gas phase at a concentration of no greater than 0.2 percent by mass.

In some embodiments, the gas phase lacks a partial pressure of the solvent that is greater than 1600 pascals. In some embodiments, the gas phase lacks a partial pressure of the solvent that is greater than 800 pascals. In some embodiments, the gas phase lacks a partial pressure of the solvent that is greater than 400 pascals. In some embodiments, the gas phase lacks a partial pressure of the solvent that is greater than 200 pascals. In some embodiments, the gas phase lacks a partial pressure of the solvent that is greater than 100 pascals. In some embodiments, the gas phase lacks a partial pressure of the solvent that is greater than 50 pascals.

In some embodiments, the gas phase lacks a partial pressure of molecular oxygen that is greater than 20 kilopascals. In some embodiments, the gas phase lacks a partial pressure of molecular oxygen that is greater than 10 kilopascals. In some embodiments, the gas phase lacks a partial pressure of molecular oxygen that is greater than 5 kilopascals. In some embodiments, the gas phase lacks a partial pressure of molecular oxygen that is greater than 2 kilopascals. In some embodiments, the gas phase lacks a partial pressure of molecular oxygen that is greater than 1 kilopascal.

In some embodiments, the composition lacks an amount by mole of molecular oxygen that is greater than the amount by mole of the anion in the composition. In some embodiments, the composition lacks an amount by mole of molecular oxygen that is greater than 50 percent of the amount by mole of the anion in the composition. In some embodiments, the composition lacks an amount by mole of molecular oxygen that is greater than 25 percent of the amount by mole of the anion in the composition. In some embodiments, the composition lacks an amount by mole of molecular oxygen that is greater than 10 percent of the amount by mole of the anion in the composition. In some embodiments, the composition lacks an amount by mole of molecular oxygen that is greater than 5 percent of the amount by mole of the anion in the composition. In some embodiments, the composition lacks an amount by mole of molecular oxygen that is greater than 2 percent of the amount by mole of the anion in the composition.

In some embodiments, the anion is selected from 5-hydroxy-4-oxo-2-(4-methoxyphenyl)-4H-chromene-7-oxide; 7-hydroxy-4-oxo-2-(4-methoxyphenyl)-4H-chromene-5-oxide; 4,6-dimethyl-2-[1-oxo-2-(2,6-dioxopiperidin-4-yl)ethyl]phenolate; 6-amino-21,28-dihydroxy-24-methoxy-7-methyl-5,19-dioxo-14,16,26-trioxa-6-azaheptacyclo[15.11.1.0$^{2,11}$.0$^{4,9}$.0$^{13,29}$.0$^{18,27}$ 0$^{20,25}$]nonacosa-1(28),2(11),3,7,9,17(29),18(27),20(25)-octaene-3-oxide; 6-amino-3,21-dihydroxy-24-methoxy-7-methyl-5,19-dioxo-14,16,26-trioxa-6-azaheptacyclo[15.11.1.0$^{2,11}$.0$^{4,9}$.0$^{13,29}$.0$^{18,27}$.0$^{20,25}$]nonacosa-1(28),2(11),3,7,9,17(29),18(27),20(25)-octaene-28-oxide; 1-hydroxy-9,10-dioxoanthracene-2-oxide; 2-hydroxy-9,10-dioxoanthracene-1-oxide; 1-methoxy-9,10-dioxoanthracene-2-oxide; 2-methoxy-9,10-dioxoanthracene-1-oxide; 4-hydroxy-5,8-dioxo-7-(1-hydroxy-4-methylpent-3-enyl)naphthalene-1-oxide; 4-hydroxy-5,8-dioxo-6-(1-hydroxy-4-methylpent-3-enyl)naphthalene-1-oxide; 8-hydroxy-3-(hydroxymethyl)-9,10-dioxoanthracene-1-oxide; 8-hydroxy-6-(hydroxymethyl)-9,10-dioxoanthracene-1-oxide; 17-hydroxy-13-methyl-6,7,8,9,11,12,14,15,16,17-decahydrocyclopenta[a]phenanthrene-3-oxide; 5-hydroxy-3-methoxy-4-methyl-2-(2-methyl-1-oxopropyl)-6-{[2,6-dihydroxy-4-methoxy-5-methyl-3-(2-methyl-1-oxopropyl)phenyl]methyl}phenolate; 3-hydroxy-5-methoxy-6-methyl-4-(2-methyl-1-oxopropyl)-2-{[2,6-dihydroxy-4-methoxy-5-methyl-3-(2-methyl-1-oxopropyl)phenyl]methyl}phenolate; 4-[3-oxo-1-(4-hydroxynaphthalen-1-yl)-2-benzofuran-1-yl]napthalene-1-oxide; 8-oxo-9-(4-hydroxy-3,5-dimethoxyphenyl)-5a,6,8a,9-tetrahydro-5H-[2]benzofuro[5,6-f][1,3]benzodioxol-4-oxide; 2,6-dimethoxy-4-(4-hydroxy-8-oxo-5a,6,8a,9-tetrahydro-5H-[2]benzofuro[5,6-f][1,3]benzodioxol-9-yl)phenolate; 2-isopropyl-7-oxocyclohepta-1,3,5-triene-1-oxide; 2,5,7,8-tetramethyl-2-(4,8,12-trimethyltridecyl)-3,4-dihydro-2H-chromene-6-oxide; 2,5,7,8-tetramethyl-2-(4,8,12-trimethyltrideca-3,7,11-trieneyl)-3,4-dihydro-2H-chromene-6-oxide; 8,18-dihydroxy-4-methyl-2-oxo-3-oxabicyclo[12.4.0]octadeca-12,14(15),16,18-tetraene-16-oxide; 8,16-dihydroxy-4-methyl-2-oxo-3-oxabicyclo[12.4.0]octadeca-12,14(15),16,18-tetraene-18-oxide; 3,7-dihydroxy-4-oxo-2-(3,4,5-trihydroxyphenyl)-2, 3-dihydro-4H-chromene-5-oxide; 3,5-dihydroxy-4-oxo-2-(3,4,5-trihydroxyphenyl)-2,3-dihydro-4H-chromene-7-oxide; 2,6-dihydroxy-4-(3,5,7-trihydroxy-4-oxo-2,3-dihydro-4H-chromen-2-yl)phenolate; 2,3-dihydroxy-5-(3,5,7-trihydroxy-4-oxo-2,3-dihydro-4H-chromen-2-yl)phenolate; 1,3-dihydroxy-9,10-dioxoanthracene-2-oxide; 2,3-dihydroxy-9,10-dioxoanthracene-1-oxide; 3,4-dihydroxy-9,10-dioxoanthracene-2-oxide; 8-hydroxy-9-oxo-9,10-dihydroanthracene-1-oxide; anthracene-9-oxide; 2,7-dihydroxy-9,10-dioxoanthracene-1-oxide; 1,7-dihydroxy-9,10-dioxoanthracene-2-oxide; 7,8-dihydroxy-9,10-dioxoanthracene-2-oxide; 1,10-dihydroxy-anthracene-2-oxide; 2,10-dihydroxy-anthracene-1-oxide; 1,2-dihydroxy-anthracene-10-oxide; 5-hydroxy-9,10-dioxoanthracene-1-oxide; 7-hydroxy-4-oxo-2-(4-hydroxyphenyl)-4H-chromene-5-oxide; 5-hydroxy-4-oxo-2-(4-hydroxyphenyl)-4H-chromene-7-oxide; 4-(5,7-dihydroxy-4-oxo-4H-chromen-2-yl)phenolate; 4-acetyl-2-methoxyphenolate; 2-hydroxy-4-[1-hydroxy-2-{N-[4-(4-hydroxyphenyl)butyl]amino}ethyl]phenolate; 2-hydroxy-5-[1-hydroxy-2-{N-[4-(4-hydroxyphenyl)butyl]amino}ethyl]phenolate; (4-{N-[2-hydroxy-2-(3,4-dihydroxyphenyl)ethyl]amino}butyl)phenolate; 3-hydroxy-4-methyl-5-methoxy-2-(1-oxobutyl)phenolate; 3-hydroxy-6-methyl-5-methoxy-2-(1-oxobutyl)phenolate; 3-[4-(4-chlorophenyl)cyclohexyl]-1,4-dioxonaphthalene-2-oxide; 2-formyl-3-hydroxy-5-methyl-4-[({3-hydroxy-2,5-dimethyl-4-[(methoxy)carbonyl]phenyl}oxy)carbonyl]phenolate; 2-formyl-3-hydroxy-5-methyl-6-[({3-hydroxy-2,5-dimethyl-4-[(methoxy)carbonyl]phenyl}oxy)carbonyl]phenolate; 2,5-dimethyl-6-[(methoxy)carbonyl]-3-{[(3-formyl-2,4-dihydroxy-6-methylphenyl)carbonyl]oxy}phenolate; 2-methoxy-4-{N-(3-hydroxy-1-oxooctyl)amino]methyl}phenolate; 5,6-hydroxy-4-oxo-2-phenyl-4H-chromene-7-oxide; 5,7-hydroxy-4-oxo-2-phenyl-4H-chromene-6-oxide; 6,7-hydroxy-4-oxo-2-phenyl-4H-chromene-5-oxide; 3-(3,4,5-trihydroxyphenyl)-4-oxo-4H-chromene-7-oxide; 5-(7-hydroxy-4-oxo-4H-chromen-3-yl)-2,3-dihydroxyphenolate; 4-(7-hydroxy-4-oxo-4H-chromen-3-yl)-2,6-dihydroxyphenolate; 4-[(2-ethyl-1-benzofuran-3-yl)carbonyl]phenolate; 2,6-dibromo-4-[(2-ethyl-1-benzofuran-3-yl)carbonyl]phenolate; 4-[3-ethyl-4-(4-hydroxyphenyl)hex-2-yl]phenolate; 4-[4-ethyl-5-(4-hydroxyphenyl)hex-3-yl]phenolate; 4-[(2-ethyl-1-benzofuran-3-yl)carbonyl]-2,6-diiodophenolate; 5-methoxy-2-[(2-hydroxy-4-methoxyphenyl)carbonyl]phenolate; (2-hydroxy-4-methoxyphen-1-yl)-(6-oxo-2-methoxycyclohexa-1,3-dien-5-ylidene)methane-oxide; 3-hydroxy-4-(phenylcarbonyl)phenolate; 3-hydroxy-6-(phenylcarbonyl)phenolate; 3,5-dihydroxy-6-methyl-2-(2-methyl-1-oxopropyl)-4-{[2-hydroxy-4,6-dimethoxy-3-methyl-5-(2-methyl-1-oxopropyl)phenyl]methyl}phenolate; 3,5-dihydroxy-4-methyl-6-(2-methyl-1-oxopropyl)-2-{[2-hydroxy-4,6-dimethoxy-3-methyl-5-(2-methyl-1-oxopropyl)phenyl]methyl}phenolate; 3,5-dihydroxy-6-methyl-4-(2-methyl-1-oxopropyl)-2-{[2-hydroxy-4,6-dimethoxy-3-methyl-5-(2-methyl-1-oxopropyl)phenyl]methyl}phenolate; 3,5-dimethoxy-6-methyl-4-(2-methyl-1-oxopropyl)-2-{[2,4,6-trihydroxy-5-methyl-3-(2-methyl-1-oxopropyl)phenyl]methyl}phenolate; 6-hydroxy-2,8-diisoprenyl-3,7-dimethoxy-9-oxoxanthene-1-oxide; 8-hydroxy-1,7-diisoprenyl-2,6-dimethoxy-9-oxoxanthene-3-oxide; 8-oxo-9-(3,4,5-trimethoxyphenyl)-5a,6,8a,9-tetrahydro-5H-[2]benzofuro[5,6-f][1,3]benzodioxol-4-oxide; 4-formyl-3-hydroxyphenolate; 6-formyl-3-hydroxyphenolate; 3-isopropyl-7-oxocyclohepta-1,3,5-triene-1-oxide; 2,5,8-trimethyl-2-(4,8,12-trimethyltridecyl)-3,4-dihydro-2H-chromene-6-oxide; 2,5,8-trimethyl-2-(4,8,12-trimethyltrideca-3,7,11-trieneyl)-3,4-dihydro-2H-chromene-6-oxide; 2-fluoro-4-[3-(3-fluoro-4-hydroxyphenyl)pent-2-yl]phenolate; 2-fluoro-4-[2-(3-fluoro-4-hydroxyphenyl)pent-3-yl]phenolate; 5-hydroxy-4-oxo-3-(4-methoxyphenyl)-4H-chromene-7-oxide; 7-hydroxy-4-oxo-3-(4-methoxyphenyl)-4H-chromene-5-oxide; 4-[2-(4-hydroxyphenyl)prop-2-yl]phenolate; 4-[2-(4-hydroxyphenyl)but-2-yl]phenolate; 3,6a,10-trihydroxy-7,11b-dihydro-6H-indeno[2,1-c]chromene-9-oxide; 3,6a,9-trihydroxy-7,11b-dihydro-6H-indeno[2,1-c]chromene-10-oxide; 6a,9,10-trihydroxy-7,11b-dihydro-6H-indeno[2,1-c]chromene-3-oxide; 2-oxo-3-{3-[4-(4-bromophenyl)phenyl]-1,2,3,4-tetrahydronaphthalen-1-yl}-2H-chromene-4-oxide; 2-oxo-3-{3-hydroxy-1-phenyl-3-[4-(4-bromophenyl)phenyl]propyl}-2H-chromene-4-oxide; 4-bromo-2-[N-(4-chlorophenyl)carbamoyl]phenolate; 4-bromo-2-(hydroxymethyl)phenolate; 3-{[4-(tert-butyl)cyclohexyl]methyl}-1,4-dioxonaphthalene-2-oxide; 1-(butyloxy)-6-methyl-1,4-dioxohepta-2,5-diene-2-oxide; 2-(tert-butyl)-4-(methoxy)phenolate; 3-(tert-butyl)-4-(methoxy)phenolate; 2,6-bis(tert-butyl)-4-methylphenolate; 4-[(butoxy)carbonyl]phenolate; 4-[4-hydroxy-3-methylbut-2-enyl]-6a,12a-dihydro-(1,3)dioxolo(5,6)[1]benzofuro[3,2-c]chromene-3(6H)-oxide; 2-[4-hydroxy-3-methylbutyl]-6a,12a-dihydro-(1,3)dioxolo(5,6)[1]benzofuro[3,2-c]chromene-3(6H)-oxide; 3-hydroxy-5-pentyl-2-(3-methyl-6-isopropenylcyclohex-2-enyl)phenolate; 5-heptyl-3-hydroxy-2-(3-methyl-6-isopropenylcyclohex-2-enyl)phenolate; 3-hydroxy-5-propyl-2-(3-methyl-6-isopropenylcyclohex-2-enyl)phenolate; 6,6,9-trimethyl-3-pentyl-benzo[c]chromene-1-oxide; 2-methoxy-4-{[N-(8-methyl-1-oxononan-6-enyl)amino]methyl}phenolate; 5-isopropyl-2-methylphenolate; 3,5-dihydroxy-2-(3,4-dihydroxyphenyl)-3,4-dihydro-2H-chromene-7-oxide; 3,7-dihydroxy-2-(3,4-dihydroxyphenyl)-3,4-dihydro-2H-chromene-5-oxide; 2-hydroxy-4-(3,5,7-trihydroxy-3,4-dihydro-2H-chromen-2-yl)phenolate; 6-hydroxy-3-(3,5,7-trihydroxy-3,4-dihydro-2H-chromen-2-yl)phenolate; 16,24-dihydroxy-14-oxahexacyclo[13.9.3.2$^{10,13}$.0$^{2,7}$.0$^{19,27}$.0$^{22,26}$]nonacosa-1(24),2,4,6,10,12,15,17,19(27),22,25,28-dodecaene-5-oxide; 5,24-dihydroxy-14-oxahexacyclo[13.9.3.2$^{10,13}$.0$^{2,7}$.0$^{19,27}$.0$^{22,26}$]nonacosa-1(24),2,4,6,10,12,15,17,19(27),22,25,28-dodecaene-16-oxide; 5,16-dihydroxy-14-oxahexacyclo[13.9.3.2$^{10,13}$.0$^{2,7}$.0$^{19,27}$.0$^{22,26}$]nonacosa-1(24),2,4,6,10,12,15,17,19(27),22,25,28-dodecaene-24-oxide; 4-(prop-2-enyl)phenolate; 7-chloro-2,3-dihydro-1H-indene-4-oxide; 8-hydroxy-3-methyl-9-oxo-10H-anthracen-1-oxide; 8-hydroxy-6-methyl-9-oxo-10H-anthracen-1-oxide; 5-hydroxy-4-oxo-2-phenyl-4H-chromene-7-oxide; 7-hydroxy-4-oxo-2-phenyl-4H-chromene-5-oxide; 2-[(2,4-dichlorophenyl)methyl]-4-(2,4,4-trimethylpent-2-yl)phenolate; 2-benzyl-4-chlorophenolate; 8-hydroxy-1-oxo-3-[(methoxy)carbonyl]-6-[2-(8-hydroxy-5,7-dimethoxy-4,9-dioxo-4,9-dihydro-benzo[f][1]benzofuran-2-yl)ethyl]-1H-isochromene-7-oxide; 7-hydroxy-1-oxo-3-[(methoxy)carbonyl]-6-[2-(8-hydroxy-5,7-dimethoxy-4,9-dioxo-4,9-dihydro-benzo[f][1]benzofuran-2-yl)ethyl]-1H-isochromene-8-oxide; 5,7-dimethoxy-4,9-dioxo-2-({7,8-dihydroxy-1-oxo-3-[(methoxy)carbonyl]-1H-isochromen-6-yl}ethyl)-4,9-dihydro-benzo[f][1]benzofuran-8-oxide; 2-methoxy-5-[2-hydroxy-2-(3,4,5-trimethoxyphenyl)ethyl]phenolate; 2-hydroxy-3-methoxy-6-[2-(3,4,5-trimethoxyphenyl)ethenyl]phenolate; 6-hydroxy-2-methoxy-5-[2-(3,4,5-trimethoxyphenyl)ethenyl]phenolate; 2-methoxy-5-[2-(3,4,5-trimethoxyphenyl)ethenyl]phenolate; 2-hydroxy-3-methoxy-6-[2-(3,4,5-trimethoxyphenyl)ethyl]phenolate; 6-hydroxy-2-methoxy-5-[2-(3,4,5-trimethoxyphenyl)ethyl]phenolate; 2-methoxy-4-(3-hydroxyprop-1-enyl)phenolate;

2-(phenylcarbonyl)-3-hydroxy-5-(methoxy)phenolate; 2-oxo-3-[1-(furan-2-yl)-3-oxobutyl]-2H-chromene-4-oxide; 9-hydroxy-6-oxobenzofurano[3,2-c]chromen-3-oxide; 3-hydroxy-6-oxobenzofurano[3,2-c]chromen-9-oxide; 2-methoxy-4-[3,5-dioxo-7-(4-hydroxy-3-methoxyphenyl)hepta-1,6-dieneyl]phenolate; 13-hydroxy-5-methyl-3,11-dioxo-4-oxabicyclo[10.4.0]hexadeca-1(12),13,15-triene-15-oxide; 15-hydroxy-5-methyl-3,11-dioxo-4-oxabicyclo[10.4.0]hexadeca-1(12),13,15-triene-13-oxide; 2-methoxy-4-[(2-oxo-3-{[4-hydroxy-3-(methyoxy)phenyl]methylidene}cyclohexylidene)methyl]phenolate; 4-oxo-3-(4-hydroxyphenyl)-4H-chromene-7-oxide; 4-(7-hydroxy-4-oxo-4H-chromen-3-yl)phenolate; 8-hydroxy-9,10-dioxoanthracene-1-oxide; 8-hydroxy-2-oxo-2H-chromene-7-oxide; 7-hydroxy-2-oxo-2H-chromene-8-oxide; 5,7-dihydroxy-4-oxo-2-(2-hydroxyphenyl)-4H-chromene-3-oxide; 3,7-dihydroxy-4-oxo-2-(2-hydroxyphenyl)-4H-chromene-5-oxide; 3,5-dihydroxy-4-oxo-2-(2-hydroxyphenyl)-4H-chromene-7-oxide; 2-(3,5,7-trihydroxy-4-oxo-4H-chromen-2-yl)phenolate; 5-methyl-2,4-bis(tert-butyl)phenolate; 1,2-dimethyl-4-oxo-1H-pyridin-3-oxide; 3-(4-hydroxyphenyl)-2H-chromene-7-oxide; 4-(7-hydroxy-2H-chromen-3-yl)phenolate; 6,6,9-trimethyl-3-pentyl-6a,7,10,10a-tetrahydro-6H-benzo[c]chromene-1-oxide; 2,8-dimethyl-2-(4,8,12-trimethyltridecyl)-3,4-dihydro-2H-chromene-6-oxide; 6,6-dimethyl-9-(hydroxymethyl)-3-(2-methyloct-2-yl)-6a,7,10,10a-tetrahydro-6H-benzo[c]chromene-1-oxide; 4-chloro-2-[(3-chloro-6-hydroxyphenyl)methyl]phenolate; 2-oxo-3-[(4-hydroxy-2-oxo-2H-chromen-3-yl)methyl]-2H-chromene-4-oxide; 4-[4-(4-hydroxyphenyl)hexa-2,4-dien-3-yl]phenolate; 4-[4-(4-hydroxyphenyl)hex-3-en-3-yl]phenolate; 4-{4-[4-(benzyloxy)phenyl]hex-3-en-3-yl}phenolate; 2-oxo-3-[3-(4-phenylphenyl)-1,2,3,4-tetrahydronaphthalen-1-yl]-2H-chromene-4-oxide; 2-methoxy-4-{[N-(8-methyl-1-oxononyl)amino]methyl}phenolate; 3,7-dihydroxy-4-oxo-2-(4-methoxyphenyl)-2,3-dihydro-4H-chromene-5-oxide; 3,5-dihydroxy-4-oxo-2-(4-methoxyphenyl)-2,3-dihydro-4H-chromene-7-oxide; 3,7-dihydroxy-4-oxo-2-(4-hydroxyphenyl)-2,3-dihydro-4H-chromene-5-oxide; 3,5-dihydroxy-4-oxo-2-(4-hydroxyphenyl)-2,3-dihydro-4H-chromene-7-oxide; 4-(3,5,7-trihydroxy-4-oxo-2,3-dihydro-4H-chromen-2-yl)phenolate; 4-[2-(3,5-dihydroxyphenyl)ethyl]phenolate; 3-hydroxy-5-[2-(4-hydroxyphenyl)ethyl]phenolate; 3-hydroxy-2-(3-methyl-6-isopropenylcyclohex-2-enyl)-5-(2-methyloctan-2-yl)phenolate; 4-[3-(4-hydroxyphenyl)but-2-en-2-yl]phenolate; 2-[(2-hydroxy-4-methoxyphenyl)carbonyl]phenolate; 3-methoxy-6-[(2-hydroxyphenyl)carbonyl]phenolate; 2-hydroxy-4-(2-{N-[4-(4-hydroxyphenyl)but-2-yl]amino}ethyl)phenolate; 2-hydroxy-5-(2-{N-[4-(4-hydroxyphenyl)but-2-yl]amino}ethyl)phenolate; 4-(3-{N-[2-(3,4-dihydroxyphenyl)ethyl]amino}butyl)phenolate; 5-hydroxy-3-undecyl-1,4-benzoquinone-2-oxide; 5-hydroxy-6-undecyl-1,4-benzoquinone-3-oxide; 4,5-dihydroxy-7-methyl-9,10-dioxoanthracene-2-oxide; 3,8-dihydroxy-6-methyl-9,10-dioxoanthracene-1-oxide; 6,8-dihydroxy-3-methyl-9,10-dioxoanthracene-1-oxide; 3-({4-oxo-5-[(3-hydroxyphenyl)methyl]-3-oxacyclopentyl}methyl)phenolate; 3-({2-oxo-5-[(3-hydroxyphenyl)methyl]-3-oxacyclopentyl}methyl)phenolate; 3-oxo-1-[9a-methyl-2,9-dioxo-6-(hydroxymethyl)-5,6-dihydro-2H-furo[3,2-g]isochromen-3-yl]deca-1,4,6,8-tetraene-1-oxide; 2,3-dihydroxy-5-({[5,7-dihydroxy-2-(3,4,5-trihydroxyphenyl)-3,4-dihydro-2H-chromen-3-yl]oxy}carbonyl)phenolate; 2,6-dihydroxy-4-({[5,7-dihydroxy-2-(3,4,5-trihydroxyphenyl)-3,4-dihydro-2H-chromen-3-yl]oxy}carbonyl)phenolate; 7-hydroxy-2-(3,4,5-trihydroxyphenyl)-3-{[(3,4,5-trihydroxyphenyl)carbonyl]oxy}-3,4-dihydro-2H-chromene-5-oxide; 5-hydroxy-2-(3,4,5-trihydroxyphenyl)-3-{[(3,4,5-trihydroxyphenyl)carbonyl]oxy}-3,4-dihydro-2H-chromene-7-oxide; 2,3-dihydroxy-5-(5,7-dihydroxy-3-{[(3,4,5-trihydroxyphenyl)carbonyl]oxy}-3,4-dihydro-2H-chromen-2-yl)phenolate; 2,6-dihydroxy-4-(5,7-dihydroxy-3-{[(3,4,5-trihydroxyphenyl)carbonyl]oxy}-3,4-dihydro-2H-chromen-2-yl)phenolate; 13-methyl-17-oxo-12,14,15,16-tetrahydro-11H-cyclopenta[a]phenanthrene-3-oxide; 13-methyl-17-oxo-9,11,12,14,15,16-hexahydro-6H-cyclopenta[a]phenanthrene-3-oxide; 3-(4-hydroxyphenyl)-3,4-dihydro-2H-chromene-7-oxide; 4-(7-hydroxy-3,4-dihydro-2H-chromen-3-yl)phenolate; 4,9a-dihydroxy-3-methyl-9-oxo-1,4a-(oxycarbonyl-0,1-diyl)-7-[4,8,9a-trihydroxy-3-methyl-9-oxo-1,4a-(oxycarbonyl-0,1-diyl)-1,2,3,4-tetrahydroxanthen-7-yl]-1,2,3,4-tetrahydroxanthene-8-oxide; 5-hydroxy-4-oxo-2-(3,4-dihydroxyphenyl)-2,3-dihydro-4H-chromene-7-oxide; 7-hydroxy-4-oxo-2-(3,4-dihydroxyphenyl)-2,3-dihydro-4H-chromene-5-oxide; 2-hydroxy-4-(5,7-dihydroxy-4-oxo-2,3-dihydro-4H-chromen-2-yl)phenolate; 2-hydroxy-5-(5,7-dihydroxy-4-oxo-2,3-dihydro-4H-chromen-2-yl)phenolate; 6-hydroxy-2-oxo-2H-chromene-7-oxide; 7-hydroxy-2-oxo-2H-chromene-6-oxide; 17-hydroxy-13-methyl-6,7,8,9,11,12,14,15,16,17-decahydrocyclopenta[a]phenanthrene-3-oxide; 13-methyl-17-{[1-oxo-3-(cyclopentyl)propyl]oxy}-6,7,8,9,11,12,14,15,16,17-decahydrocyclopenta[a]phenanthrene-3-oxide; 13-methyl-17-[(1-oxoheptyl)oxy]-6,7,8,9,11,12,14,15,16,17-decahydrocyclopenta[a]phenanthrene-3-oxide; 13-methyl-17-[(1-oxoundecyl)oxy]-6,7,8,9,11,12,14,15,16,17-decahydrocyclopenta[a]phenanthrene-3-oxide; 13-methyl-17-[(1-oxopentyl)oxy]-6,7,8,9,11,12,14,15,16,17-decahydrocyclopenta[a]phenanthrene-3-oxide; 16,17-dihydroxy-13-methyl-6,7,8,9,11,12,14,15,16,17-decahydrocyclopenta[a]phenanthrene-3-oxide; 13-methyl-17-oxo-7,8,9,11,12,14,15,16-octahydro-6H-cyclopenta[a]phenanthrene-3-oxide; 2,7-dimethyl-2-(4,8,12-trimethyltridecyl)-3,4-dihydro-2H-chromene-6-oxide; 17-ethynyl-17-hydroxy-13-methyl-7,8,9,11,12,14,15,16-octahydro-6H-cyclopenta[a]phenanthrene-3-oxide; 2-oxo-3-[2-(ethoxy)-2-oxo-1-(4-hydroxy-2-oxo-2H-chromen-3-yl)ethyl]-2H-chromene-4-oxide; 2-ethyl-4-oxo-4H-pyran-3-oxide; 2-ethoxy-4-formylphenolate; 2-oxo-3-[1-(4-hydroxy-2-oxo-2H-chromen-3-yl)ethyl]-2H-chromene-4-oxide; 4-[(ethoxy)carbonyl]phenolate; 2-methoxy-4-(prop-2-enyl)phenolate; 5-acetyl-2-isopropenyl-1-benzofuran-6-oxide; 6,7-dimethoxy-4-oxo-2-(3-hydroxy-4-methoxyphenyl)-4H-chromene-5-oxide; 2-methoxy-5-(5-hydroxy-6,7-dimethoxy-4-oxo-4H-chromen-2-yl)phenolate; 3-hydroxy-5-(1-hydroxy-2-{N-[1-(4-hydroxyphenyl)prop-2-yl]amino}ethyl)phenolate; 4-(2-{N-[2-hydroxy-2-(3,5-dihydroxyphenyl)ethyl]amino}propyl)phenolate; 4-{N-[3,7-dimethyl-1-oxo-9-(2,6,6-trimethylcyclohex-1-enyl)nona-2,4,6,8-tetraenyl]amino}phenolate; 7-hydroxy-4-oxo-2-(3,4-dihydroxyphenyl)-4H-chromene-3-oxide; 3-hydroxy-4-oxo-2-(3,4-dihydroxyphenyl)-4H-chromene-7-oxide; 2-hydroxy-4-(3,7-dihydroxy-4-oxo-4H-chromen-2-yl)phenolate; 2-hydroxy-5-(3,7-dihydroxy-4-oxo-4H-chromen-2-yl)phenolate; 2,6-dihydroxy-9,10-dioxoanthracene-1-oxide; 1,6-dihydroxy-9,10-dioxoanthracene-2-oxide; 5,6-dihydroxy-9,10-dioxoanthracene-2-oxide; 2-oxo-3-{3-[4-({[4-(trifluoromethyl)phenyl]methyl}oxy)phenyl]-1,2,3,4-tetrahydronaphthalen-1-yl}-2H-chromene-4-oxide; 3,5-dihydroxy-2-(1-oxopropyl)phenolate; 3,5-dihydroxy-4-(1-oxopropyl)phenolate; 6'-hydroxy-3-oxospiro(2-benzofuran-1,9'-xanthene)-3'-oxide; 10,13-methyl-3,17-dioxo-2,6,7,8,9, 11,12,14,15,16-decahydro-1H-cyclopenta[a]phenanthrene-4-oxide; 4-oxo-3-(4-methoxyphenyl)-4H-chromene-7-oxide; 8-hydroxy-6-methoxy-2-oxo-2H-chromene-7-oxide; 7-hydroxy-6-methoxy-2-oxo-2H-chromene-8-oxide; 17-hydroxy-13-methyl-7-{9-[(4,4,5,5,5-pentafluoropentyl)sulfinyl]nonyl}-6,7,8,9,11,12,14,15,16,17-decahydrocyclopenta[a]phenanthrene-3-oxide; 6-methyl-3-methoxy-1,4-benzoquinone-2-oxide; 3,10-dihydroxy-3-methyl-7-methoxy-6,9-dioxo-1,4-dihydrobenzo[g]isochromene-5-oxide; 3,5-dihydroxy-3-methyl-7-methoxy-6,9-dioxo-1,4-dihydrobenzo[g]isochromene-10-oxide; 4,8,8-trimethyl-2,6-dioxo-9,10-dihydro-4H-pyrano[3,2-f]isochromene-5-oxide; 3-hydroxy-4-oxo-2-(3,4-dihydroxyphenyl)-2,3-dihydro-4H-chromene-7-oxide; 2-hydroxy-4-(3,7-dihydroxy-4-oxo-2,3-dihydro-4H-chromen-2-yl)phenolate; 2-hydroxy-5-(3,7-dihydroxy-4-oxo-2,3-dihydro-4H-chromen-2-yl)phenolate; 3,5-dihydroxy-4-oxo-2-phenyl-4H-chromene-7-oxide; 3,7-dihydroxy-4-oxo-2-phenyl-4H-chromene-5-oxide; 5,7-dihydroxy-4-oxo-2-phenyl-4H-chromene-3-oxide; 4',5',6'-trihydroxy-1-oxospiro[2-benzofuran-3,9'-xanthene]-3'-oxide; 3',5',6'-trihydroxy-1-oxospiro[2-benzofuran-3,9'-xanthene]-4'-oxide; 3,5-dihydroxy-2-(3,4,5-trihydroxyphenyl)-3,4-dihydro-2H-chromene-7-oxide; 3,7-dihydroxy-2-(3,4,5-trihydroxyphenyl)-3,4-dihydro-2H-chromene-5-oxide; 2,6-dihydroxy-4-(3,5,7-trihydroxy-3,4-dihydro-2H-chromen-2-yl)phenolate; 2,3-dihydroxy-5-(3,5,7-trihydroxy-3,4-dihydro-2H-chromen-2-yl)phenolate; 3,6,7-trihydroxy-2,8-diisoprenyl-9-oxoxanthene-1-oxide; 3,6,8-trihydroxy-1,7-diisoprenyl-9-oxoxanthene-2-oxide; 1,6,7-trihydroxy-2,8-diisoprenyl-9-oxoxanthene-3-oxide; 2,6,8-trihydroxy-1,7-diisoprenyl-9-oxoxanthene-3-oxide; 4-isopropyl-7-oxocyclohepta-1,3,5-triene-1-oxide; 2,7,8-trimethyl-2-(4,8,12-trimethyltridecyl)-3,4-dihydro-2H-chromene-6-oxide; 6,7,8-trimethoxy-4-oxo-2-(3,4,5-trimethoxyphenyl)-4H-chromene-5-oxide; 6,7,8-trimethoxy-4-oxo-2-(4-methoxyphenyl)-4H-chromene-5-oxide; 6,7,8-trimethoxy-4-oxo-2-(3-hydroxy-4,5-dimethoxyphenyl)-4H-chromene-5-oxide; 2,3-dimethoxy-5-(5-hydroxy-6,7,8-trimethoxy-4-oxo-4H-chromen-2-yl)phenolate; 6,7,8-trimethoxy-4-oxo-2-(3-hydroxy-4-methoxyphenyl)-4H-chromene-5-oxide; 2-methoxy-5-(5-hydroxy-6,7,8-trimethoxy-4-oxo-4H-chromen-2-yl)phenolate; 6,7,8-trimethoxy-4-oxo-2-(3,5-dihydroxy-4-methoxyphenyl)-4H-chromene-5-oxide; 3-hydroxy-2-methoxy-5-(5-hydroxy-6,7,8-trimethoxy-4-oxo-4H-chromen-2-yl)phenolate; 5-hydroxy-4-oxo-3-(4-hydroxyphenyl)-4H-chromene-7-oxide; 7-hydroxy-4-oxo-3-(4-hydroxyphenyl)-4H-chromene-5-oxide; 4-(5,7-dihydroxy-4-oxo-4H-chromen-3-yl)phenolate; 8-hydroxy-6-methoxy-9-oxoxanthene-2-oxide; 7-hydroxy-3-methoxy-9-oxoxanthene-1-oxide; 4-hydroxy-2-(hydroxymethyl)phenolate; 4-hydroxy-3-(hydroxymethyl)phenolate; 2-geranyl-4-hydroxyphenolate; 3-geranyl-4-hydroxyphenolate; 8-formyl-6,7-dihydroxy-5-isopropyl-3-methyl-2-(8-formyl-1,6,7-trihydroxy-5-isopropyl-3-methylnapthalen-2-yl)napthalene-1-oxide; 1-formyl-3,8-dihydroxy-4-isopropyl-6-methyl-7-(8-formyl-1,6,7-trihydroxy-5-isopropyl-3-methylnapthalen-2-yl)napthalene-2-oxide; 4-formyl-3,5-dihydroxy-1-isopropyl-7-methyl-6-(8-formyl-1,6,7-trihydroxy-5-isopropyl-3-methylnapthalen-2-yl)napthalene-2-oxide; 2-methoxyphenolate; 3,4,6a-trihydroxy-9-oxo-6,7-dihydroindeno[2,1-c]chromene-10-oxide; 3,6a,10-trihydroxy-9-oxo-6,7-dihydroindeno[2,1-c]chromene-4-oxide; 4,6a,10-trihydroxy-9-oxo-6,7-dihydroindeno[2,1-c]chromene-3-oxide; 3,4,6a,9-tetrahydroxy-7,11b-dihydro-6H-indeno[2,1-c]chromene-10-oxide; 3,4,6a,10-tetrahydroxy-7,11b-dihydro-6H-indeno[2,1-c]chromene-9-oxide; 3,6a,9,10-tetrahydroxy-7,11b-dihydro-6H-indeno[2,1-c]chromene-4-oxide; 4,6a,9,10-tetrahydroxy-7,11b-dihydro-6H-indeno[2,1-c]chromene-3-oxide; 2-hydroxy-4-[2,3-dimethyl-4-(4-hydroxy-3-methoxyphenyl)butyl]phenolate; 2-hydroxy-5-[2,3-dimethyl-4-(4-hydroxy-3-methoxyphenyl)butyl]phenolate; 2-methoxy-4-[2,3-dimethyl-4-(3,4-dihydroxyphenyl)butyl]phenolate; 6,7a-dihydroxy-5-methoxy-1,8,8,9-tetramethyl-3,7-dioxo-9H-phenaleno[1,2-b]furan-4-oxide; 4,7a-dihydroxy-5-methoxy-1,8,8,9-tetramethyl-3,7-dioxo-9H-phenaleno[1,2-b]furan-6-oxide; 5-hydroxy-4-oxo-2-(3-hydroxy-4-methoxyphenyl)-2,3-dihydro-4H-chromene-7-oxide; 7-hydroxy-4-oxo-2-(3-hydroxy-4-methoxyphenyl)-2,3-dihydro-4H-chromene-5-oxide; 2-methoxy-5-(5,7-dihydroxy-4-oxo-2,3-dihydro-4H-chromen-2-yl)phenolate; 4-[4-(4-hydroxyphenyl)hex-3-yl]phenolate; 2-methoxy-4-{[N-(9-methyl-1-oxodec-6-enyl)amino]methyl}phenolate; 2-methoxy-4-{[N-(8-methyl-1-oxodec-6-enyl)amino]methyl}phenolate; 2-methoxy-4-{[N-(9-methyl-1-oxodecyl)amino]methyl}phenolate; 5-hydroxy-4-oxo-2-(4-hydroxy-3-methoxyphenyl)-2,3-dihydro-4H-chromene-7-oxide; 7-hydroxy-4-oxo-2-(4-hydroxy-3-methoxyphenyl)-2,3-dihydro-4H-chromene-5-oxide; 2-methoxy-4-(5,7-dihydroxy-4-oxo-2,3-dihydro-4H-chromen-2-yl)phenolate; 2-{[(3,3,5-trimethylcyclohexyl)oxy]carbonyl}phenolate; 4-(2-hydroxyethyl)-2-methoxyphenolate; 2-(prop-2-enyl)-4-[2-hydroxy-5-(prop-2-enyl)phenyl]phenolate; 4-(prop-2-enyl)-2-[4-hydroxy-3-(prop-2-enyl)phenyl]phenolate; 3,4-dihydroquinoline-2-oxide; 2-hydroxy-4-(2-hydroxyethyl)phenolate; 2-hydroxy-5-(2-hydroxyethyl)phenolate; 4-methyl-2-oxo-2H-chromene-7-oxide; 7-oxo-4-methyl-7H-chromene-2-oxide; 5-methoxy-3-[(1,2,4a-trimethyl-5-methylidene-3,4,6,7,8,8a-hexahydro-2H-naphthalen-1-yl)methyl]-1,4-benzoquinone-2-oxide; 5-hydroxy-6-methoxy-4-oxo-3-(3-hydroxy-4,5-dimethoxyphenyl)-4H-chromene-7-oxide; 7-hydroxy-6-methoxy-4-oxo-3-(3-hydroxy-4,5-dimethoxyphenyl)-4H-chromene-5-oxide; 2,3-dimethoxy-5-(5,7-dihydroxy-6-methoxy-4-oxo-4H-chromen-3-yl)phenolate; 4-(9-methoxy-8-oxo-[1,3]diolxolo[4,5-g]chromen-7-yl)phenolate; 17-hydroxy-13-methyl-6,7,8,9,11,12,14,15,16,17-decahydrocyclopenta[a]phenanthrene-3-oxide; 2-methoxy-4-(prop-1-enyl)phenolate; 2-acetylfuran-3-oxide; 3,7-dihydroxy-4-oxo-2-[3-(4-hydroxy-3-methoxyphenyl)-2-(hydroxymethyl)-2,3-dihydro-1,4-benzodioxin-7-yl]-2,3-dihydro-4H-chromene-5-oxide; 3,5-dihydroxy-4-oxo-2-[3-(4-hydroxy-3-methoxyphenyl)-2-(hydroxymethyl)-2,3-dihydro-1,4-benzodioxin-7-yl]-2,3-dihydro-4H-chromene-7-oxide; 2-methoxy-4-[2-hydroxymethyl-7-(3,5,7-trihydroxy-4-oxo-2,3-dihydro-4H-chromen-2-yl)-2,3-dihydro-1,4-benzodioxin-3-yl]phenolate; 3-{N-[(4-oxo-1H-quinolin-3-yl)carbonyl]amino}-4,6-bis(tert-butyl)phenolate; 4-hydroxy-2-methoxy-6-methyl-5,8-dioxo-7-(2-oxopropyl)naphthalene-1-oxide; 5,8-dioxo-4-hydroxy-3-methoxy-7-methyl-6-(2-oxo-propyl)-naphthalene-1-oxide; 5,8-dioxonaphthalene-1-oxide; 5,7-dihydroxy-4-oxo-2-(4-hydroxyphenyl)-4H-chromene-3-oxide; 3,7-dihydroxy-4-oxo-2-(4-hydroxyphenyl)-4H-chromene-5-oxide; 3,5-dihydroxy-4-oxo-2-(4-hydroxyphenyl)-4H-chromene-7-oxide; 4-(3,5,7-trihydroxy-4-oxo-4H-chromen-2-yl)phenolate; 3-isoprenyl-1,4-dioxonaphthalene-2-oxide; 1,4-dioxonaphthalene-2-oxide; 3,4,7-trihydroxy-2-(3,4-dihydroxyphenyl)-3,4-dihydro-2H-chromene-6-oxide; 3,4,5-trihydroxy-2-(3,4-dihydroxyphenyl)-3,4-dihydro-2H-chromene-7-oxide; 2-hydroxy-4-(3,4,5,7-tetrahydroxy-3,4-dihydro-2H-chromen-2-yl)phenolate; 2-hydroxy-5-(3,4,5,7-tetrahydroxy-3,4-dihydro-2H-chromen-2-yl)phenolate; 4-{1-oxo-3-[4-hydroxy-2- methoxy-5-(2-methylbut-3-en-2-yl)phenyl]prop-2-enyl}phenolate; 3-methoxy-6-(2-methylbut-3-en-2-yl)-4-[3-oxo-3-(4-hydroxyphenyl)prop-1-enyl]phenolate; 4-[1-oxo-3-(3,4-dihydroxy-2-methoxyphenyl)prop-2-enyl]phenolate; 2-hydroxy-3-methoxy-4-[3-oxo-3-(4-hydroxyphenyl)prop-1-enyl]phenolate; 6-hydroxy-2-methoxy-3-[3-oxo-3-(4-hydroxyphenyl)prop-1-enyl]phenolate; 4-{1-oxo-3-[4-hydroxy-3-isoprenyl-2-methoxyphenyl]prop-2-enyl}phenolate; 2-isoprenyl-3-methoxy-4-[3-oxo-3-(4-hydroxyphenyl)prop-1-enyl]phenolate; 2-isoprenyl-4-[1-oxo-3-(3,4-dihydroxy-2-methoxyphenyl)prop-2-enyl]phenolate; 2-hydroxy-3-methoxy-4-[3-oxo-3-(4-hydroxy-3-isoprenylphenyl)prop-1-enyl]phenolate; 6-hydroxy-2-methoxy-3-[3-oxo-3-(4-hydroxy-3-isoprenylphenyl)prop-1-enyl]phenolate; 4-{1-oxo-3-[4-hydroxy-2-methoxy-5-(3-methylbut-3-en-2-yl)phenyl]prop-2-enyl}phenolate; 3-methoxy-6-(3-methylbut-3-en-2-yl)-4-[3-oxo-3-(4-hydroxyphenyl)prop-1-enyl]phenolate; 4-{1-oxo-3-[4-hydroxy-2-methoxy-3-(3-methylbut-3-en-2-yl)phenyl]prop-2-enyl}phenolate; 3-methoxy-2-(3-methylbut-3-en-2-yl)-4-[3-oxo-3-(4-hydroxyphenyl)prop-1-enyl]phenolate; N-methyl-2-oxo-3-[(N-methyl-N-phenylamino)carbonyl]-1,2-dihydroquinoline-4-oxide; 7-hydroxy-4-oxo-2-(3,4-dihydroxyphenyl)-4H-chromene-5-oxide; 5-hydroxy-4-oxo-2-(3,4-dihydroxyphenyl)-4H-chromene-7-oxide; 2-hydroxy-4-(5,7-dihydroxy-4-oxo-4H-chromen-2-yl)phenolate; 2-hydroxy-5-(5,7-dihydroxy-4-oxo-4H-chromen-2-yl)phenolate; 4-(prop-2-enyl)-2-[2-hydroxy-5-(prop-2-enyl)phenyl]phenolate; 2-methyl-4-oxo-4H-pyran-3-oxide; 6,8-dihydroxy-1,7-diisoprenyl-2-methoxy-9-oxoxanthene-3-oxide; 3,6-dihydroxy-2,8-diisoprenyl-7-methoxy-9-oxoxanthene-1-oxide; 1,6-dihydroxy-2,8-diisoprenyl-7-methoxy-9-oxoxanthene-3-oxide; 6-oxo-(1,3)dioxolo(5,6)[1]benzofuro[3,2-c]chromene-3-oxide; 9-methoxy-6a,11a-dihydro-6H-[1]benzofuro[3,2-c]chromene-3-oxide; 4-hydroxy-2-methylnaphthalene-1-oxide; 4-hydroxy-3-methyl-naphthalene-1-oxide; 4-[4-(4-methoxyphenyl)hex-3-en-3-yl]phenolate; 3-methylphenolate; 2-methyl-4-[4-(4-hydroxy-3-methylphenyl)hex-3-yl]phenolate; 5-hydroxy-3-methyl-4-oxo-2-phenyl-4H-chromene-7-oxide; 7-hydroxy-3-methyl-4-oxo-2-phenyl-4H-chromene-5-oxide; 4-[(methoxy)carbonyl]phenolate; 3-methoxy-6-[(4-methylphenyl)carbonyl]phenolate; 4-[(benzyl)oxy]phenolate; 5,7-dihydroxy-4-oxo-2-(2,4-dihydroxyphenyl)-4H-chromene-3-oxide; 3,7-dihydroxy-4-oxo-2-(2,4-dihydroxyphenyl)-4H-chromene-5-oxide; 3,5-dihydroxy-4-oxo-2-(2,4-dihydroxyphenyl)-4H-chromene-7-oxide; 3-hydroxy-4-(3,5,7-trihydroxy-4-oxo-4H-chromen-2-yl)phenolate; 3-hydroxy-6-(3,5,7-trihydroxy-4-oxo-4H-chromen-2-yl)phenolate; phenanthro[4,5-bcd]furan-3-oxide; 17-ethynyl-17-hydroxy-11-methoxy-13-methyl-7,8,9,11,12,14,15,16-octahydro-6H-cyclopenta[a]phenanthrene-3-oxide; 5,7-dihydroxy-4-oxo-2-(3,4,5-trihydroxyphenyl)-4H-chromene-3-oxide; 3,7-dihydroxy-4-oxo-2-(3,4,5-trihydroxyphenyl)-4H-chromene-5-oxide; 3,5-dihydroxy-4-oxo-2-(3,4,5-trihydroxyphenyl)-4H-chromene-7-oxide; 2,6-dihydroxy-4-(3,5,7-trihydroxy-4-oxo-4H-chromen-2-yl)phenolate; 2,3-dihydroxy-5-(3,5,7-trihydroxy-4-oxo-4H-chromen-2-yl)phenolate; 6,6-dimethyl-9-oxo-3-(2-methyloct-2-yl)-7,8,10,10a-tetrahydro-6aH-benzo[c]chromene-1-oxide; 3-hydroxynapthalene-1-oxide; 4-hydroxynapthalene-2-oxide; 7-hydroxy-4-oxo-2-(4-hydroxyphenyl)-2,3-dihydro-4H-chromene-5-oxide; 5-hydroxy-4-oxo-2-(4-hydroxyphenyl)-2,3-dihydro-4H-chromene-7-oxide; 4-(5,7-dihydroxy-4-oxo-2,3-dihydro-4H-chromen-2-yl)phenolate; 2,4b,8,8-tetramethyl-10-oxo-4b,5,6,7,8a,9-hexahydrophenanthrene-3-oxide; 2-methoxy-4-{[N-(1-oxononyl)amine]methyl}phenolate; 2-methoxy-4-{[N-(7-methyl-1-oxooctyl)amino]methyl}phenolate; 2-hydroxy-4-[2,3-dimethyl-4-(3,4-dihydroxyphenyl)butyl]phenolate; 2-hydroxy-5-[2,3-dimethyl-4-(3,4-dihydroxyphenyl)butyl]phenolate; 6-[(phenyl)carbonyl]-3-[(octyl)oxy]phenolate; 4-(2-{[3-(2-oxoethyl)-4-formyl-1-oxohex-4-enyl]oxy}ethyl)phenolate; 7-hydroxy-6-methoxy-4-oxo-2-phenyl-4H-chromene-5-oxide; 5-hydroxy-6-methoxy-4-oxo-2-phenyl-4H-chromene-7-oxide; 2-benzylphenolate; 2-amino-4-(methoxycarbonyl)phenolate; 2-methylphenolate; 2-methoxy-4-(3-oxo-3-{[4,4,13,14-tetramethyl-9,10-methanediyl-17-(6-methylhept-5-en-2-yl)-1,2,3,5,6,7,8,11,12,15,16,17-dodecahydrocyclopenta[a]phenanthren-3-yl]oxy}prop-1-enyl)phenolate; 2-methoxy-4-(3-oxo-3-{[4,4,13,14-tetramethyl-9,10-methanediyl-17-(5-methylidene-6-methylhept-2-yl)-1,2,3,5,6,7,8,11,12,15,16,17-dodecahydrocyclopenta[a]phenanthren-3-yl]oxy}prop-1-enyl)phenolate; 6-isoprenyl-8,8-dimethyl-4-oxo-3-(4-hydroxyphenyl)pyrano[2,3-h]chromene-5-oxide; 4-(5-hydroxy-6-isoprenyl-8,8-dimethyl-4-oxopyrano[2,3-h]chromen-3-yl)phenolate; 2-[N-(4-hydroxyphenyl)carbamoyl]phenolate; 4-{N-[(2-hydroxyphenyl)carbonyl]amino}phenolate; 6-geranyl-2-oxo-2H-chromene-7-oxide; 3,5-dihydroxy-2-(3,5-dihydroxy-4-methoxyphenyl)-3,4-dihydro-2H-chromene-7-oxide; 3,7-dihydroxy-2-(3,5-dihydroxy-4-methoxyphenyl)-3,4-dihydro-2H-chromene-5-oxide; 3-hydroxy-2-methoxy-5-(3,5,7-trihydroxy-3,4-dihydro-2H-chromen-2-yl)phenolate; (8R,9S,10R,13S,14S,17S)-17-hydroxy-13-methyl-3-oxo-2,6,7,8,9,10,11,12,14,15,16,17-dodecahydro-1H-cyclopenta[a]phenanthrene-4-oxide; (8R,9S,10R,13S,14S,17S)-13-methyl-3-oxo-17-[(3-cyclopentyl-1-oxopropyl)oxy]-2,6,7,8,9,10,11,12,14,15,16,17-dodecahydro-1H-cyclopenta[a]phenanthrene-4-oxide; 3-methoxy-6-[(phenyl)carbonyl]phenolate; 17-hydroxy-10,13,17-trimethyl-3-oxo-2,6,7,8,9,11,12,14,15,16-decahydro-1H-cyclopenta[a]phenanthrene-4-oxide; [17-hydroxy-10,13,17-trimethyl-3-oxo-1,4,5,6,7,8,9,11,12,14,15,16-dodecahydrocyclopenta[a]phenanthren-2-ylidene]methane-oxide; 4-(4-butyl-3,5-dioxo-2-phenylpyrazolidin-1-yl)phenolate; 4-(prop-1-enyl)phenolate; 4-benzylphenolate; 4-methylphenolate; 4-(tert-pentyl)phenolate; 4-ethenyl-2-methoxyphenolate; 8-hydroxy-6-methyl-3-methoxy-9,10-dioxoanthracene-1-oxide; 8-hydroxy-3-methyl-6-methoxy-9,10-dioxoanthracene-1-oxide; 4-(1-oxopropyl)phenolate; 3-cyclohexyl-1,4-dioxonaphthalene-2-oxide; 7-hydroxy-6-methoxy-4-oxo-2-(4-methoxyphenyl)-4H-chromene-5-oxide; 5-hydroxy-6-methoxy-4-oxo-2-(4-methoxyphenyl)-4H-chromene-7-oxide; 6-methyl-3-(6-methylhept-5-en-2-yl)-1,4-benzoquinone-2-oxide; 3,3-dimethyl-7,12b-dihydro-6bH-furo[3,2-c:5,4-f]dichromen-10-oxide; 4-{(4-hydroxyphenyl)-[2-(hydroxymethyl)phenyl]methyl}phenolate; 2-oxo-3-(1-phenylpropyl)-2H-chromene-4-oxide; 3,5-dihydroxy-2-[1-oxo-3-(4-hydroxyphenyl)propyl]phenolate; 3,5-dihydroxy-4-[1-oxo-3-(4-hydroxyphenyl)propyl]phenolate; 4-[3-oxo-3-(2,4,6-trihydroxyphenyl)propyl]phenolate; 3-methyl-1,4-dioxonaphthalene-2-oxide; 3-hydroxy-5-(2-phenylethenyl)phenolate; 3-methoxy-5-(2-phenylethenyl)phenolate; 6-methyl-5,8-dioxonaphthalene-1-oxide; 7-hydroxy-4-oxo-3-(3-hydroxy-4-methoxyphenyl)-4H-chromene-5-oxide; 5-hydroxy-4-oxo-3-(3-hydroxy-4-methoxyphenyl)-4H-chromene-7-oxide; 2-methoxy-5-(5,7-dihydroxy-4-oxo-4H-chromen-3-yl)phenolate; 2,6-di-tert-butyl-4-({2-[(3,5-di-tert-butyl-4-hydroxyphenyl)sulfanyl]prop-2-yl}sulfanyl)phenolate; 4-isoprenyl-5-isopropenyl-7-oxocyclohepta-1,3,5-trien-1-oxide; 2,6-diisopropylphenolate; 2,3-dihydroxy-5-[(propoxy)carbonyl]phenolate; 2,6-dihydroxy-4-[(propoxy)

carbonyl]phenolate; 4-[(propoxy)carbonyl]phenolate; 4-hydroxy-2,5-bis{[(propyl)oxy]carbonyl}thiophene-3-oxide; 4-formyl-2-hydroxyphenolate; 5-formyl-2-hydroxyphenolate; 7-methoxy-4-oxo-3-(4-hydroxyphenyl)-4H-chromene-5-oxide; 4-(5-hydroxy-7-methoxy-4-oxo-4H-chromen-3-yl)phenolate; 3-(1,3-benzodioxol-5-yl)-4-oxo-4H-chromene-7-oxide; 4,6-diformyl-7-hydroxy-10,13,13,17-tetramethyl-9-phenyl-2-oxapentacyclo[8.7.2.0$^{1,11}$.0$^{3,8}$.0$^{12,14}$]nonadeca-3,5,7-triene-5-oxide; 4,6-diformyl-5-hydroxy-10,13,13,17-tetramethyl-9-phenyl-2-oxapentacyclo[8.7.2.0$^{1,11}$.0$^{3,8}$.0$^{12,14}$]nonadeca-3,5,7-triene-7-oxide; 4,6-diformyl-7-hydroxy-13,16,16-trimethyl-9-phenyl-2-oxapentacyclo[11.6.1.0$^{1,10}$.0$^{3,8}$.0$^{14,17}$]icosa-3,5,7-triene-5-oxide; 4,6-diformyl-5-hydroxy-13,16,16-trimethyl-9-phenyl-2-oxapentacyclo[11.6.1.0$^{1,10}$.0$^{3,8}$.0$^{14,17}$]icosa-3,5,7-triene-7-oxide; 4,6-diformyl-7-hydroxy-10,14,19,19-tetramethyl-9-phenyl-2,13-dioxapentacyclo[8.10.0.0$^{3,8}$.0$^{12,14}$.0$^{18,20}$]icosa-3,5,7-triene-5-oxide; 4,6-diformyl-5-hydroxy-10,14,19,19-tetramethyl-9-phenyl-2,13-dioxapentacyclo[8.10.0.0$^{3,8}$.0$^{12,14}$.0$^{18,20}$]icosa-3,5,7-triene-7-oxide; 4,6-diformyl-7-hydroxy-10,14,18,18-tetramethyl-9-phenyl-2-oxa-tetracyclo[8.10.0.0$^{3,8}$.0$^{17,19}$]nonadeca-3,5,7,13-tetraene-5-oxide; 4,6-diformyl-5-hydroxy-10,14,18,18-tetramethyl-9-phenyl-2-oxa-tetracyclo[8.10.0.0$^{3,8}$.0$^{17,19}$]nonadeca-3,5,7,13-tetraene-7-oxide; 9-hydroxy-2-isoprenyl-6-oxo-[1]benzofurano[3,2-c]chromene-3-oxide; 3-hydroxy-2-isoprenyl-6-oxo-[1]benzofurano[3,2-c]chromene-9-oxide; 2,4-dihydroxy-9,10-dioxoanthracene-1-oxide; 1,4-dihydroxy-9,10-dioxoanthracene-2-oxide; 3,4-dihydroxy-9,10-dioxoanthracene-1-oxide; 3-hydroxy-4-methoxy-9,10-dioxoanthracene-1-oxide; 4-hydroxy-1-methoxy-9,10-dioxoanthracene-2-oxide; 2,4-dimethoxy-9,10-dioxoanthracene-1-oxide; 4-hydroxy-2-methoxy-9,10-dioxoanthracene-1-oxide; 4-hydroxy-3-methoxy-9,10-dioxoanthracene-1-oxide; 3,4,6-trihydroxy-5-oxobenzo[7]annulen-2-oxide; 1,3,8-trihydroxy-9-oxobenzo[7]annulen-2-oxide; 2,3,8-trihydroxy-9-oxobenzo[7]annulen-1-oxide; 2,3,4-trihydroxy-5-oxobenzo[7]annulen-6-oxide; 5,6,7-trihydroxy-4-oxo-2-(3,4-dihydroxyphenyl)-4H-chromene-3-oxide; 3,6,7-trihydroxy-4-oxo-2-(3,4-dihydroxyphenyl)-4H-chromene-5-oxide; 3,5,7-trihydroxy-4-oxo-2-(3,4-dihydroxyphenyl)-4H-chromene-6-oxide; 3,5,6-trihydroxy-4-oxo-2-(3,4-dihydroxyphenyl)-4H-chromene-7-oxide; 2-hydroxy-4-(3,5,6,7-tetrahydroxy-4-oxo-4H-chromen-2-yl)phenolate; 2-hydroxy-5-(3,5,6,7-tetrahydroxy-4-oxo-4H-chromen-2-yl)phenolate; 5,7-dihydroxy-4-oxo-2-(3,4-dihydroxyphenyl)-4H-chromene-3-oxide; 3,7-dihydroxy-4-oxo-2-(3,4-dihydroxyphenyl)-4H-chromene-5-oxide; 3,5-dihydroxy-4-oxo-2-(3,4-dihydroxyphenyl)-4H-chromene-7-oxide; 2-hydroxy-4-(3,5,7-trihydroxy-4-oxo-4H-chromen-2-yl)phenolate; 2-hydroxy-5-(3,5,7-trihydroxy-4-oxo-4H-chromen-2-yl)phenolate; 2,5,8-trihydroxy-9,10-dioxoanthracene-1-oxide; 1,5,8-trihydroxy-9,10-dioxoanthracene-2-oxide; 4,5,6-trihydroxy-9,10-dioxoanthracene-1-oxide; 4,7,8-trihydroxy-9,10-dioxoanthracene-1-oxide; 4-(3-oxobutyl)phenolate; 4-acetyl-3-hydroxyphenolate; 6-acetyl-3-hydroxyphenolate; 4-[2-(3,5-dihydroxyphenyl)ethenyl]phenolate; 3-hydroxy-5-[2-(4-hydroxyphenyl)ethenyl]phenolate; 5-hydroxy-7-methoxy-4-oxo-2-(3,4-hydroxyphenyl)-4H-chromene-3-oxide; 3-hydroxy-7-methoxy-4-oxo-2-(3,4-hydroxyphenyl)-4H-chromene-5-oxide; 2-hydroxy-4-(3,5-dihydroxy-7-methoxy-4-oxo-4H-chromen-2-yl)phenolate; 2-hydroxy-5-(3,5-dihydroxy-7-methoxy-4-oxo-4H-chromen-2-yl)phenolate; 7-hydroxy-2,2-dimethyl-8-(1-oxo-3-phenylprop-2-enyl)-6-[(3-acetyl-2,4,6-trihydroxy-5-methylphenyl)methyl]-2H-chromene-5-oxide; 5-hydroxy-2,2-dimethyl-8-(1-oxo-3-phenylprop-2-enyl)-6-[(3-acetyl-2,4,6-trihydroxy-5-methylphenyl)methyl]-2H-chromene-7-oxide; 2-acetyl-3,5-dihydroxy-4-methyl-6-{[5,7-dihydroxy-2,2-dimethyl-8-(1-oxo-3-phenylprop-2-enyl)-2H-chromen-6-yl]methyl}phenolate; 4-acetyl-3,5-dihydroxy-6-methyl-2-{[5,7-dihydroxy-2,2-dimethyl-8-(1-oxo-3-phenylprop-2-enyl)-2H-chromen-6-yl]methyl}phenolate; 2-acetyl-3,5-dihydroxy-6-methyl-4-{[5,7-dihydroxy-2,2-dimethyl-8-(1-oxo-3-phenylprop-2-enyl)-2H-chromen-6-yl]methyl}phenolate; 2-acetyl-3,5-dihydroxy-4-methyl-6-{[5,7-dimethoxy-2,2-dimethyl-8-(1-oxo-3-phenylprop-2-enyl)-2H-chromen-6-yl]methyl}phenolate; 2-acetyl-3,5-dihydroxy-6-methyl-4-{[5,7-dimethoxy-2,2-dimethyl-8-(1-oxo-3-phenylprop-2-enyl)-2H-chromen-6-yl]methyl}phenolate; 4-acetyl-3,5-dihydroxy-6-methyl-2-{[5,7-dimethoxy-2,2-dimethyl-8-(1-oxo-3-phenylprop-2-enyl)-2H-chromen-6-yl]methyl}phenolate; 3-hydroxy-2-methyl-9,10-dioxoanthracene-1-oxide; 4-hydroxy-3-methyl-9,10-dioxoanthracene-2-oxide; 2-(hydroxymethyl)phenolate; 2-formylphenolate; 2-[(N-phenylamino)carbonyl]phenolate; 6-methoxy-2-oxo-2H-chromene-7-oxide; 6,7-dihydroxy-4-oxo-2-(4-hydroxyphenyl)-4H-chromene-5-oxide; 5,7-dihydroxy-4-oxo-2-(4-hydroxyphenyl)-4H-chromene-6-oxide; 5,6-dihydroxy-4-oxo-2-(4-hydroxyphenyl)-4H-chromene-7-oxide; 4-(5,6,7-trihydroxy-4-oxo-4H-chromen-2-yl)phenolate; 8,12,16,16-tetramethyl-3,11-dioxapentacyclo[10.7.1.0$^{1,15}$.0$^{4,20}$.0$^{5,10}$]icosa-5,7,9-triene-6-oxide; 3,7-dihydroxy-4-oxo-2-[3-(4-hydroxy-3-methoxyphenyl)-2-(hydroxymethyl)-2,3-dihydro-1,4-benzodioxin-6-yl]-2,3-dihydro-4H-chromene-5-oxide; 3,5-dihydroxy-4-oxo-2-[3-(4-hydroxy-3-methoxyphenyl)-2-(hydroxymethyl)-2,3-dihydro-1,4-benzodioxin-6-yl]-2,3-dihydro-4H-chromene-7-oxide; 2-methoxy-4-[2-hydroxymethyl-6-(3,5,7-trihydroxy-4-oxo-2,3-dihydro-4H-chromen-2-yl)-2,3-dihydro-1,4-benzodioxin-3-yl]phenolate; 3-methoxy-6-methoxycarbonyl-5-methylphenolate; 4-[2-(4-hydroxyphenyl)ethenyl]phenolate; 2-[(isoprenyl)oxy]-5-{6-methoxy-5-[(methoxy)carbonyl]-4-methylhexa-1,3,5-trienyl}phenolate; 3-oxo-2-[(3,4-dihydroxyphenyl)methylidene]-1-benzofuran-6-oxide; 2-hydroxy-4-[(6-hydroxy-3-oxo-1-benzofuran-2-ylidene)methyl]phenolate; 2-hydroxy-5-[(6-hydroxy-3-oxo-1-benzofuran-2-ylidene)methyl]phenolate; 2-isopropenyl-8,9-dihydroxy-6-oxo-2,6a,12,12a-tetrahydro-1H-chromeno[3,4-b]furo[2,3-h]chromene-5-oxide; 3-hexyl-6,6,9-trimethyl-7,8,9,10-tetrahydro-6H-benzo[c]chromene-1-oxide; 4-formyl-2,6-dimethoxyphenolate; 2-isopropyl-4b,8,8-trimethyl-3,9-dioxo-5,6,7,8a-tetrahydrophenanthrene-4-oxide; 7-hydroxy-6-methoxy-4-oxo-3-(4-hydroxyphenyl)-4H-chromene-5-oxide; 5-hydroxy-6-methoxy-4-oxo-3-(4-hydroxyphenyl)-4H-chromene-7-oxide; 4-(5,7-dihydroxy-6-methoxy-4-oxo-4H-chromen-3-yl)phenolate; 6,6,9-trimethyl-3-pentyl-6a,7,8,10a-tetrahydro-6H-benzo[c]chromene-1-oxide; 3-butyl-6,6,9-trimethyl-6a,7,8,10a-tetrahydro-6H-benzo[c]chromene-1-oxide; 3,6,6,9-tetramethyl-6a,7,8,10a-tetrahydro-6H-benzo[c]chromene-1-oxide; 3-heptyl-6,6,9-trimethyl-6a,7,8,10a-tetrahydro-6H-benzo[c]chromene-1-oxide; 6,6,9-trimethyl-3-propyl-6a,7,8,10a-tetrahydro-6H-benzo[c]chromene-1-oxide; 7-hydroxy-2,2-dimethyl-8-(1-oxo-3-phenylpropyl)-6-[(3-acetyl-2,4,6-trihydroxy-5-methylphenyl)methyl]-3,4-dihydro-2H-chromene-5-oxide; 5-hydroxy-2,2-dimethyl-8-(1-oxo-3-phenylpropyl)-6-[(3-acetyl-2,4,6-trihydroxy-5-methylphenyl)methyl]-3,4-dihydro-2H-chromene-7-oxide; 2-acetyl-3,5-dihydroxy-4-methyl-6-{[5,7-dihydroxy-2,2-dimethyl-8-(1-oxo-3-phenylpropyl)-3,4-dihydro-2H-chromen-6-yl]methyl}phenolate; 4-acetyl-3,5-dihydroxy-6- methyl-2-{[5,7-dihydroxy-2,2-dimethyl-8-(1-oxo-3-phenylpropyl)-3,4-dihydro-2H-chromen-6-yl]methyl}phenolate; 2-acetyl-3,5-dihydroxy-6-methyl-4-{[5,7-dihydroxy-2,2-dimethyl-8-(1-oxo-3-phenylpropyl)-3,4-dihydro-2H-chromen-6-yl]methyl}phenolate; 2-isopropyl-5-methylphenolate; 2-oxo-3-[3-hydroxy-3-(4-chlorophenyl)-1-(5-chlorothiophen-2-yl)propyl]-2H-chromene-4-oxide; 2-hydroxy-3-nitro-5-[(4-methylphenyl)carbonyl]phenolate; 6-hydroxy-2-nitro-4-[(4-methylphenyl)carbonyl]phenolate; 2-cyano-4,5-epoxy-17-hydroxy-10,13-dimethyl-1,4,6,7,8,9,11,12,14,15,16,17-dodecahydrocyclopenta[a]phenanthrene-3-oxide; 4-(2-hydroxyethyl)phenolate; 5-hydroxy-6,6-dimethyl-3-oxo-4-(2-methyl-1-oxopropyl)-2-{[2,4,6-trihydroxy-5-isoprenyl-3-(2-methyl-1-oxopropyl)phenyl]methyl}cyclohexa-1,4-diene-1-oxide; 5-hydroxy-6,6-dimethyl-3-oxo-2-(2-methyl-1-oxopropyl)-4-{[2,4,6-trihydroxy-5-isoprenyl-3-(2-methyl-1-oxopropyl)phenyl]methyl}cyclohexa-1,4-diene-1-oxide; 3,5-dihydroxy-4-isoprenyl-6-(2-methyl-1-oxopropyl)-2-{[2,4-dihydroxy-3,3-dimethyl-6-oxo-5-(2-methyl-1-oxopropyl)cyclohexa-1,4-dien-1-yl]methyl}phenolate; 3,5-dihydroxy-6-isoprenyl-4-(2-methyl-1-oxopropyl)-2-{[2,4-dihydroxy-3,3-dimethyl-6-oxo-5-(2-methyl-1-oxopropyl)cyclohexa-1,4-dien-1-yl]methyl}phenolate; 3,5-dihydroxy-6-isoprenyl-2-(2-methyl-1-oxopropyl)-4-{[2,4-dihydroxy-3,3-dimethyl-6-oxo-5-(2-methyl-1-oxopropyl)cyclohexa-1,4-dien-1-yl]methyl}phenolate; 5-hydroxy-6,6-dimethyl-3-oxo-4-(2-methyl-1-oxopropyl)-2-{[5,7-dihydroxy-2,2-dimethyl-8-(2-methyl-1-oxopropyl)-2H-chromen-6-yl]methyl}cyclohexa-1,4-dien-1-oxide; 5-hydroxy-6,6-dimethyl-3-oxo-2-(2-methyl-1-oxopropyl)-4-{[5,7-dihydroxy-2,2-dimethyl-8-(2-methyl-1-oxopropyl)-2H-chromen-6-yl]methyl}cyclohexa-1,4-dien-1-oxide; 7-hydroxy-2,2-dimethyl-8-(2-methyl-1-oxopropyl)-6-{[2,4-dihydroxy-3,3-dimethyl-6-oxo-5-(2-methyl-1-oxopropyl)cyclohexa-1,4-dien-1-yl]methyl}-2H-chromene-5-oxide; 5-hydroxy-2,2-dimethyl-8-(2-methyl-1-oxopropyl)-6-{[2,4-dihydroxy-3,3-dimethyl-6-oxo-5-(2-methyl-1-oxopropyl)cyclohexa-1,4-dien-1-yl]methyl}-2H-chromene-7-oxide; 2-oxo-2H-chromene-7-oxide; 4-formyl-2-methoxyphenolate; 4-(hydroxymethyl)-2-methoxyphenolate; 3-[5-oxo-4-(2-oxo-1H-indol-3-ylidene)-1H-pyrrol-2-yl]-1H-indol-5-oxide; 4-phenyl-2-oxo-1H-quinolin-3-oxide; 2-acetyl-3,5-dimethoxyphenolate; 4,5-dimethyl-2-[1,7,7-trimethylbicyclo[2.2.1]hept-2-yl]phenolate; 18-hydroxy-4-methyl-2,8-dioxo-3-oxabicyclo[12.4.0]octadeca-12,14,16,18-tetraene-16-oxide; 16-hydroxy-4-methyl-2,8-dioxo-3-oxabicyclo[12.4.0]octadeca-12,14,16,18-tetraene-18-oxide; 8,18-dihydroxy-4-methyl-2-oxo-3-oxabicyclo[12.4.0]octadeca-14,16,18-triene-16-oxide; 8,16-dihydroxy-4-methyl-2-oxo-3-oxabicyclo[12.4.0]octadeca-14,16,18-triene-18-oxide; 2,5,7-trimethyl-2-(4,8,12-trimethyltridecyl)-3,4-dihydro-2H-chromene-6-oxide; 4-(3-oxobutyl)-2-methoxyphenolate; 2-methoxy-4-(5-hydroxy-3-oxopentyl)phenolate; 2-methoxy-4-(5-hydroxy-3-oxotetradecyl)phenolate; 2-methoxy-4-(5-hydroxy-3-oxohexadecyl)phenolate; 2-methoxy-4-(5-hydroxy-3-oxooctadecyl)phenolate; 2-methoxy-4-(5-hydroxy-3-oxoicosyl)phenolate; 2-methoxy-4-(5-hydroxy-3-oxohexyl)phenolate; 2-methoxy-4-(5-hydroxy-3-oxoheptyl)phenolate; 2-methoxy-4-(5-hydroxy-3-oxooctyl)phenolate; 2-methoxy-4-(5-hydroxy-3-oxononyl)phenolate; 2-methoxy-4-(5-hydroxy-3-oxodecyl)phenolate; 2-methoxy-4-(5-hydroxy-3-oxoundecyl)phenolate; 2-methoxy-4-(5-hydroxy-3-oxododecyl)phenolate; 2-methoxy-4-(5-hydroxy-3-oxotridecyl)phenolate; 16,17-dihydroxy-13-methyl-6,7,8,9,11,12,14,15,16,17-decahydrocyclopenta[a]phenanthrene-3-oxide; 17-hydroxy-13-methyl-6,9,11,12,14,15,16,17-octahydrocyclopenta[a]phenanthrene-3-oxide; 4-hydroxy-2,5-bis(2-methylbut-2-yl)phenolate; 2',7'-dichloro-6'-hydroxy-3-oxospiro(2-benzofuran-1,9'-xanthene)-3'-oxide; naphthalene-2-oxide; 2,8-diisoprenyl-3,6,7-trimethoxy-9-oxoxanthene-1-oxide; 2-methoxy-4-(1,2-dihydroxyethyl)phenolate; 4',5'-dichloro-6'-hydroxy-3-oxospiro(2-benzofuran-1,9'-xanthene)-3'-oxide; 6'-hydroxy-4',5'-diiodo-3-oxospiro(2-benzofuran-1,9'-xanthene)-3'-oxide; 4-fluoro-3-hydroxy-5-pentyl-2-(3-methyl-6-isopropenylcyclohex-2-enyl)phenolate; 6-fluoro-3-hydroxy-5-pentyl-2-(3-methyl-6-isopropenylcyclohex-2-enyl)phenolate; 4-hexyl-3-hydroxyphenolate; 6-hexyl-3-hydroxyphenolate; 4-(prop-2-enyl)-2-[4-methoxy-3-(prop-2-enyl)phenyl]phenolate; 5,7-dihydroxy-4-oxo-2-(4-methoxyphenyl)-4H-chromene-3-oxide; 3,7-dihydroxy-4-oxo-2-(4-methoxyphenyl)-4H-chromene-5-oxide; 3,5-dihydroxy-4-oxo-2-(4-methoxyphenyl)-4H-chromene-7-oxide; 2-methoxy-4-(5-ethoxy-3-oxotetradecyl)phenolate; 2-methoxy-4-(5-methoxy-3-oxotridecyl)phenolate; 3,7-dihydroxy-2,8-diisoprenyl-9-oxoxanthene-1-oxide; 6,8-dihydroxy-1,7-diisoprenyl-9-oxoxanthene-2-oxide; 1,7-dihydroxy-2,8-diisoprenyl-9-oxoxanthene-3-oxide; 13-methyl-17-oxo-7,8,9,11,12,14,15,16-octahydro-6H-cyclopenta[a]phenanthrene-3-oxide; 2-methoxy-4-(5,9-dihydroxy-3-oxodecyl)phenolate; 2-oxo-5-[1-hydroxy-2-(N-{6-[(2,2-difluoro-2-phenylethyl)oxy]hexyl}amino)ethyl]-1H-quinoline-8-oxide; 3-hydroxy-5-pentyl-4-(3-methyl-6-isopropenylcyclohex-2-enyl)phenolate; 7-hydroxy-6,8-dimethoxy-4-oxo-2-(3-hydroxy-4-methoxyphenyl)-4H-chromene-5-oxide; 5-hydroxy-6,8-dimethoxy-4-oxo-2-(3-hydroxy-4-methoxyphenyl)-4H-chromene-7-oxide; 2-methoxy-5-(5,7-dihydroxy-6,8-dimethoxy-4-oxo-4H-chromen-2-yl)phenolate; 4-acetyl-2,6-dimethoxyphenolate; 3-hydroxy-5-pentadecylphenolate; 3,7-dihydroxy-2-(4-hydroxyphenyl)-3,4-dihydro-2H-chromene-5-oxide; 3,5-dihydroxy-2-(4-hydroxyphenyl)-3,4-dihydro-2H-chromene-7-oxide; 4-(3,5,7-trihydroxy-3,4-dihydro-2H-chromen-2-yl)phenolate; 2,6-dimethoxy-4-[2-hydroxymethyl-5-methoxy-8-oxo-2,3-dihydropyrano[2,3-h][1,4]benzodioxin-3-yl]phenolate; 6,7,8-trimethoxy-2-phenyl-4-oxo-4H-chromene-5-oxide; 7,9-dihydroxy-1-methyl-6-oxo-6H-benzo[c]chromene-3-oxide; 3-(6-bromo-2-methylhex-2-yl)-6,6,9-trimethyl-6a,7,10,10a-tetrahydrobenzo[c]chromene-1-oxide; 9-hydroxy-3-(2-methyloct-2-yl)-6-oxo-6H-benzo[c]chromene-1-oxide; 3-(1-hexylcyclobutyl)-9-hydroxy-6,6-dimethyl-6a,7,8,9,10,10a-hexahydro-6H-benzo[c]chromene-1-oxide; 9-(hydroxymethyl)-6-(3-hydroxyprop-1-enyl)-6-methyl-3-(2-methyloct-2-yl)-6a,7,8,9,10,10a-hexahydro-6H-benzo[c]chromene-1-oxide; 4-[N-(1-oxoicosa-5,8,11,14-tetraenyl)amino]phenolate; 3-(1-adamantyl)-6,6,9-trimethyl-6a,7,10,10a-tetrahydro-6H-benzo[c]chromene-1-oxide; 8-hexyl-2,5,5-trimethyl-1,4,4a,8,9,10,11,12b-octahydronaphtho[3,2-c]isochromen-12-oxide; 3-(hept-1-enyl)-9-(hydroxymethyl)-6,6-dimethyl-6a,7,8,9,10,10a-hexahydro-6H-benzo[c]chromene-1-oxide; 9-(hydroxymethyl)-6-(3-hydroxypropyl)-6-methyl-3-(2-methyloct-2-yl)-6a,7,8,9,10,10a-hexahydro-6H-benzo[c]chromene-1-oxide; 9-(hydroxymethyl)-6-(3-hydroxyprop-1-ynyl)-6-methyl-3-(2-methyloct-2-yl)-6a,7,8,9,10,10a-hexahydro-6H-benzo[c]chromene-1-oxide; 7-hydroxy-2-(4-hydroxyphenyl)-4-oxo-8-[2-hydroxy-5-(5,7-dihydroxy-4-oxo-4H-chromen-2-yl)phenyl]-4H-chromene-5-oxide; 5-hydroxy-2-(4-hydroxyphenyl)-4-oxo-8-[2-hydroxy-5-(5,7-dihydroxy-4-oxo-4H-chromen-2-yl)phenyl]-4H-chromene-7-oxide; 4-{5,7-dihydroxy-4-oxo-8-[2-hydroxy- 5-(5,7-dihydroxy-4-oxo-4H-chromen-2-yl)phenyl]-4H-chromen-2-yl}phenolate; 7-hydroxy-4-oxo-2-[4-hydroxy-5-(5,7-dihydroxy-2-(4-hydroxyphenyl)-4-oxo-4H-chromen-8-yl)phenyl]-4H-chromene-5-oxide; 5-hydroxy-4-oxo-2-[4-hydroxy-5-(5,7-dihydroxy-2-(4-hydroxyphenyl)-4-oxo-4H-chromen-8-yl)phenyl]-4H-chromene-7-oxide; 3-(hept-1-ynyl)-6,6,9-trimethyl-6a,7,10,10a-tetrahydro-6H-benzo[c]chromene-1-oxide; 3-(1-hexylcyclopentyl)-6,6,9-trimethyl-6a,7,10,10a-tetrahydro-6H-benzo[c]chromene-1-oxide; 3-(1-hexylcyclopropyl)-6,6,9-trimethyl-6a,7,10,10a-tetrahydro-6H-benzo[c]chromene-1-oxide; 5-methyl-2-pentylphenolate; 4,7-dihydroxy-2-(4-hydroxyphenyl)-3,4-dihydro-2H-chromene-5-oxide; 4,5-dihydroxy-2-(4-hydroxyphenyl)-3,4-dihydro-2H-chromene-7-oxide; 4-(4,5,7-trihydroxy-3,4-dihydro-2H-chromen-2-yl)phenolate; 2-methoxy-4-({2-oxo-5-[(3,4-dimethoxyphenyl)methyl]-3-oxacyclopentyl}methyl)phenolate; 7-methoxy-4-oxo-2-(2,4-dihydroxyphenol)-4H-chromene-5-oxide; 3-hydroxy-4-(5-hydroxy-7-methoxy-4-oxo-4H-chromen-2-yl)phenolate; 3-hydroxy-6-(5-hydroxy-7-methoxy-4-oxo-4H-chromen-2-yl)phenolate; 3,6-diisoprenyl-7-methoxy-4-oxo-2-(2,4-dihydroxyphenyl)-4H-chromene-5-oxide; 3-hydroxy-4-(5-hydroxy-3,6-diisoprenyl-7-methoxy-4-oxo-4H-chromen-2-yl)phenolate; 3-hydroxy-6-(5-hydroxy-3,6-diisoprenyl-7-methoxy-4-oxo-4H-chromen-2-yl)phenolate; 2-chloro-4-formyl-5-hydroxy-3-methyl-6-[3-methyl-7-(3-oxo-4,4-dimethyl-5-oxacyclopentyl)octa-2,6-dienyl]phenolate; 4-chloro-6-formyl-3-hydroxy-5-methyl-2-[3-methyl-7-(3-oxo-4,4-dimethyl-5-oxacyclopentyl)octa-2,6-dienyl]phenolate; 4-hydroxy-3-oxo-2-[(3,4-dihydroxyphenyl)methylidene]-1-benzofuran-6-oxide; 6-hydroxy-3-oxo-2-[(3,4-dihydroxyphenyl)methylidene]-1-benzofuran-4-oxide; 2-hydroxy-4-[(4,6-dihydroxy-3-oxo-1-benzofuran-2-ylidene)methyl]phenolate; 2-hydroxy-5-[(4,6-dihydroxy-3-oxo-1-benzofuran-2-ylidene)methyl]phenolate; 5-hydroxy-3,6-dimethoxy-4-oxo-2-(3,4-dihydroxyphenyl)-4H-chromene-7-oxide; 7-hydroxy-3,6-dimethoxy-4-oxo-2-(3,4-dihydroxyphenyl)-4H-chromene-5-oxide; 2-hydroxy-4-(5,7-dihydroxy-3,6-dimethoxy-4-oxo-4H-chromen-2-yl)phenolate; 2-hydroxy-5-(5,7-dihydroxy-3,6-dimethoxy-4-oxo-4H-chromen-2-yl)phenolate; 7-hydroxy-5-methoxy-4-oxo-2-(2,4-dihydroxyphenyl)-4H-chromene-3-oxide; 3-hydroxy-5-methoxy-4-oxo-2-(2,4-dihydroxyphenyl)-4H-chromene-7-oxide; 2-hydroxy-4-(3,7-dihydroxy-5-methoxy-4-oxo-4H-chromen-2-yl)phenolate; 2-hydroxy-5-(3,7-dihydroxy-5-methoxy-4-oxo-4H-chromen-2-yl)phenolate; 4-(3-ethenyl-3,7-dimethylocta-1,6-dienyl)phenolate; 2-methoxy-4-[3-hydroxymethyl-7-methoxy-5-(3-oxoprop-1-enyl)-2,3-dihydro-1-benzofuran-2-yl]phenolate; 3-hydroxy-4-[(2,4-dihydroyphenyl)carbonyl]phenolate; 3-hydroxy-6-[(2,4-dihydroyphenyl)carbonyl]phenolate; 3-hydroxy-5-(pentadec-8-enyl)phenolate; 4-[3,5-dioxo-7-(4-hydroxyphenyl)hepta-1,6-dieneyl]phenolate; 4-[(4-hydroxyphenyl)methyl]phenolate; 7-methoxy-4-oxo-2-(3,5-dihydroxyphenyl)-2,3-dihydro-4H-chromene-5-oxide; 3-hydroxy-5-(5-hydroxy-7-methoxy-4-oxo-2,3-dihydro-4H-chromen-2-yl)phenolate; 4-oxo-2-(3,4-dihydroxyphenyl)-2,3-dihydro-4H-chromene-7-oxide; 2-hydroxy-4-(7-hydroxy-4-oxo-2,3-dihydro-4H-chromen-2-yl)phenolate; 2-hydroxy-5-(7-hydroxy-4-oxo-2,3-dihydro-4H-chromen-2-yl)phenolate; 7-hydroxy-8-isoprenyl-4-oxo-2-(4-hydroxy-3-methoxyphenyl)-4H-chromene-5-oxide; 5-hydroxy-8-isoprenyl-4-oxo-2-(4-hydroxy-3-methoxyphenyl)-4H-chromene-7-oxide; 2-methoxy-4-(5,7-dihydroxy-8-isoprenyl-4-oxo-4H-chromen-2-yl)phenolate; 10-hydroxy-2,6,7,11-tetramethoxy-4,9-dioxo-1,12-bis[2-(benzoyloxy)propyl]perylene-3-oxide; 10-hydroxy-2,6,7,11-tetramethoxy-4,9-dioxo-12-(2-hydroxypropyl)-1-[2-(benzoyloxy)propyl]perylene-3-oxide; 10-hydroxy-2,6,7,11-tetramethoxy-4,9-dioxo-1-(2-hydroxypropyl)-12-[2-(benzoyloxy)propyl]perylene-3-oxide; 10-hydroxy-2,6,7,11-tetramethoxy-4,9-dioxo-12-[2-(benzoyloxy)propyl]-1-[2-({[(4-hydroxyphenyl)oxy]carbonyl}oxy)propyl]perylene-3-oxide; 10-hydroxy-2,6,7,11-tetramethoxy-4,9-dioxo-1-[2-(benzoyloxy)propyl]-12-[2-({[(4-hydroxyphenyl)oxy]carbonyl}oxy)propyl]perylene-3-oxide; 10-hydroxy-2,6,7,11-tetramethoxy-4,9-dioxo-1,12-bis(2-hydroxypropyl)perylene-3-oxide; 4-oxo-3-(3-hydroxy-4-methoxyphenyl)-4H-chromene-7-oxide; 2-methoxy-5-(7-hydroxy-4-oxo-4H-chromen-3-yl)phenolate; 2-methoxy-4-(3-oxo-3-{[10,13-dimethyl-17-(5,6-dimethylhept-2-yl)-2,3,4,7,8,9,11,12,14,15,16,17-dodecahydro-1H-cyclopenta[a]phenanthren-3-yl]oxy}prop-1-enyl)phenolate; 9-hydroxy-6,6-dimethyl-3-(2-methyloct-2-yl)-6a,7,8,9,10,10a-hexahydro-6H-benzo[c]chromene-1-oxide; 2-methyl-7-pentyl-2-(4-methylpent-3-enyl)-2H-chromene-5-oxide; 2-(3-hydroxycyclohexyl)-5-(2-methylnonan-2-yl)phenolate; 9,13,13-trimethyl-5-pentyl-8-oxatetracyclo[7.4.1.0$^{2,7}$.0$^{12,14}$]tetradeca-2,4,6-trien-3-oxide; 9,13,13-trimethyl-5-propyl-8-oxatetracyclo[7.4.1.0$^{2,7}$.0$^{12,14}$]tetradeca-2,4,6-trien-3-oxide; 3-hydroxy-2-geranyl-5-pentylphenolate; 3-hydroxy-2-geranyl-5-propylphenolate; 6-geranyl-7-hydroxy-4-oxo-2-(4-hydroxy-3-methoxyphenolate)-4H-chromene-5-oxide; 6-geranyl-5-hydroxy-4-oxo-2-(4-hydroxy-3-methoxyphenolate)-4H-chromene-7-oxide; 2-methoxy-4-(6-geranyl-5,7-dihydroxy-4-oxo-4H-chromen-2-yl)phenolate; 7-hydroxy-6-isoprenyl-4-oxo-2-(4-hydroxy-3-methoxyphenolate)-4H-chromene-5-oxide; 5-hydroxy-6-isoprenyl-4-oxo-2-(4-hydroxy-3-methoxyphenolate)-4H-chromene-7-oxide; 2-methoxy-4-(5,7-dihydroxy-6-isoprenyl-4-oxo-4H-chromen-2-yl)phenolate; 8-geranyl-7-hydroxy-4-oxo-2-(4-hydroxy-3-methoxyphenolate)-4H-chromene-5-oxide; 8-geranyl-5-hydroxy-4-oxo-2-(4-hydroxy-3-methoxyphenolate)-4H-chromene-7-oxide; 2-methoxy-4-(8-geranyl-5,7-dihydroxy-4-oxo-4H-chromen-2-yl)phenolate; 4-ethenyl-2,6-dimethoxyphenolate; 6,8-dihydroxy-2,3-dimethyl-4-oxo-9-(5,6,8-trihydroxy-2,3-dimethyl-4-oxo-2,3-dihydrobenzo[g]chromen-9-yl)-2,3-dihydrobenzo[g]chromene-5-oxide; 5,8-dihydroxy-2,3-dimethyl-4-oxo-9-(5,6,8-trihydroxy-2,3-dimethyl-4-oxo-2,3-dihydrobenzo[g]chromen-9-yl)-2,3-dihydrobenzo[g]chromene-6-oxide; 5,6-dihydroxy-2,3-dimethyl-4-oxo-9-(5,6,8-trihydroxy-2,3-dimethyl-4-oxo-2,3-dihydrobenzo[g]chromen-9-yl)-2,3-dihydrobenzo[g]chromene-8-oxide; 6,8-dihydroxy-2,3-dimethyl-4-oxo-9-(5,6,8-trihydroxy-2-methyl-4-oxo-2,3-dihydrobenzo[g]chromen-9-yl)-2,3-dihydrobenzo[g]chromene-5-oxide; 5,8-dihydroxy-2,3-dimethyl-4-oxo-9-(5,6,8-trihydroxy-2-methyl-4-oxo-2,3-dihydrobenzo[g]chromen-9-yl)-2,3-dihydrobenzo[g]chromene-6-oxide; 5,6-dihydroxy-2,3-dimethyl-4-oxo-9-(5,6,8-trihydroxy-2-methyl-4-oxo-2,3-dihydrobenzo[g]chromen-9-yl)-2,3-dihydrobenzo[g]chromene-8-oxide; 6,8-dihydroxy-2-methyl-4-oxo-9-(5,6,8-trihydroxy-2,3-dimethyl-4-oxo-2,3-dihydrobenzo[g]chromen-9-yl)-2,3-dihydrobenzo[g]chromene-5-oxide; 5,8-dihydroxy-2-methyl-4-oxo-9-(5,6,8-trihydroxy-2,3-dimethyl-4-oxo-2,3-dihydrobenzo[g]chromen-9-yl)-2,3-dihydrobenzo[g]chromene-6-oxide; 5,6-dihydroxy-2-methyl-4-oxo-9-(5,6,8-trihydroxy-2,3-dimethyl-4-oxo-2,3-dihydrobenzo[g]chromen-9-yl)-2,3-dihydrobenzo[g]chromene-8-oxide; 5,6-dihydroxy-2,3-dimethyl-8-oxo-9-(5,6,8-trihydroxy-2,3-dimethyl-4-oxo-2,3-dihydrobenzo[g]chromen-9-yl)benzo[g]chromene-4-oxide; 4,6-dihydroxy-2,3-dimethyl-8-oxo-9-(5,6,8-trihydroxy-2,3-dimethyl-4-oxo-2,3-dihydrobenzo[g]

chromen-9-yl)benzo[g]chromene-5-oxide; 4,5-dihydroxy-2,3-dimethyl-8-oxo-9-(5,6,8-trihydroxy-2,3-dimethyl-4-oxo-2,3-dihydrobenzo[g]chromen-9-yl)benzo[g]chromene-6-oxide; 6,8-dihydroxy-2,3-dimethyl-4-oxo-9-(4,5,6-trihydroxy-2,3-dimethyl-8-oxo-benzo[g]chromen-9-yl)-2,3-dihydrobenzo[g]chromene-5-oxide; 5,8-dihydroxy-2,3-dimethyl-4-oxo-9-(4,5,6-trihydroxy-2,3-dimethyl-8-oxo-benzo[g]chromen-9-yl)-2,3-dihydrobenzo[g]chromene-6-oxide; 5,6-dihydroxy-2,3-dimethyl-4-oxo-9-(4,5,6-trihydroxy-2,3-dimethyl-8-oxo-benzo[g]chromen-9-yl)-2,3-dihydrobenzo[g]chromene-8-oxide; 2-methoxy-5-(prop-2-enyl)phenolate; 7-hydroxy-4-oxo-2-(4-hydroxy-3-methoxyphenyl)-4H-chromene-5-oxide; 5-hydroxy-4-oxo-2-(4-hydroxy-3-methoxyphenyl)-4H-chromene-7-oxide; 2-methoxy-4-(5,7-dihydroxy-4-oxo-4H-chromen-2-yl)phenolate; 6,7-dimethoxy-4-oxo-2-(4-hydroxy-3-methoxyphenyl)-4H-chromene-5-oxide; 2-methoxy-4-(5-hydroxy-6,7-dimethoxy-4-oxo-4H-chromen-2-yl)phenolate; 6,7-dimethoxy-4-oxo-2-(3,4-dihydroxyphenyl)-4H-chromene-5-oxide; 2-hydroxy-4-(5-hydroxy-6,7-dimethoxy-4-oxo-4H-chromen-2-yl)phenolate; 2-hydroxy-5-(5-hydroxy-6,7-dimethoxy-4-oxo-4H-chromen-2-yl)phenolate; 6,7-dimethoxy-4-oxo-2-(4-hydroxyphenyl)-4H-chromene-5-oxide; 4-(5-hydroxy-6,7-dimethoxy-4-oxo-4H-chromen-2-yl)phenolate; 7-methoxy-4-oxo-2-(3,4,5-trimethoxyphenyl)-4H-chromene-5-oxide; 2-oxo-3-(1,2,3,4-tetrahydronaphthalen-1-yl)-2H-chromene-4-oxide; 2-[3-hydroxy-7-(hydroxymethyl)-1,2,3,4,4a,5,6,7,8,8a-decahydronaphthalen-1-yl]-5-(2-methyloct-2-yl)phenolate; 2-[3-hydroxy-6-(3-hydroxypropyl)cyclohexyl]-5-(2-methyloct-2-yl)phenolate; 3-formyl-4-methoxy-9,10-dioxoanthracene-2-oxide; 2-hexyl-3-hydroxy-5-propylphenolate; 10-hydroxy-2,5-dimethyl-7,12-dioxo-5-(4-methylpent-3-enyl)-3,4,4a,12b-tetrahydrodibenzo[c,g]chromene-8-oxide; 8-hydroxy-2,5-dimethyl-7,12-dioxo-5-(4-methylpent-3-enyl)-3,4,4a,12b-tetrahydrodibenzo[c,g]chromene-10-oxide; 2,8-dimethyl-2-(4,8,12-trimethyltrideca-3,7,11-trienyl)-3,4-dihydro-2H-chromene-6-oxide; 4-[7-(4-hydroxy-3-methoxyphenyl)-3,5-dioxohepta-1,6-dienyl]phenolate; 2-methoxy-4-[7-(4-hydroxyphenyl)-3,5-dioxohepta-1,6-dienyl]phenolate; 7-hydroxy-6-isoprenyl-4-oxo-3-(1,3-benzodioxol-5-yl)-4H-chromene-5-oxide; 5-hydroxy-6-isoprenyl-4-oxo-3-(1,3-benzodioxol-5-yl)-4H-chromene-7-oxide; 4-[3-(4-hydroxyphenyl)-2-methylpent-1-enyl]phenolate; 4-[1-(4-hydroxyphenyl)-2-methylpent-1-en-3-yl]phenolate; 3,4,5,6-tetramethoxy-2-(3-phenyl-1-oxopropyl)phenolate; 3,7-dihydroxy-4-oxo-2-(2,4-dihydroxyphenyl)-2,3-dihydro-4H-chromene-5-oxide; 3,5-dihydroxy-4-oxo-2-(2,4-dihydroxyphenyl)-2,3-dihydro-4H-chromene-7-oxide; 3-hydroxy-4-(3,5,7-trihydroxy-4-oxo-2,3-dihydro-4H-chromen-2-yl)phenolate; 3-hydroxy-6-(3,5,7-trihydroxy-4-oxo-2,3-dihydro-4H-chromen-2-yl)phenolate; 6,6,9-trimethyl-3-(3-methyloct-2-yl)-7,8,9,10-tetrahydro-6H-benzo[c]chromene-1-oxide; 7-hydroxy-4-oxo-2-(3-hydroxy-4-methoxyphenyl)-4H-chromene-5-oxide; 5-hydroxy-4-oxo-2-(3-hydroxy-4-methoxyphenyl)-4H-chromene-7-oxide; 2-methoxy-5-(5,7-dihydroxy-4-oxo-4H-chromen-2-yl)phenolate; 2-hydroxy-4-(2-oxoethyl)phenolate; 2-hydroxy-5-(2-oxoethyl)phenolate; 2-hydroxy-4-(1,2-dihydroxyethyl)phenolate; 2-hydroxy-5-(1,2-dihydroxyethyl)phenolate; 4-(4-ethenyl-4,7-dimethyl-1,6-octadien-2-yl)phenolate; 2-methoxy-4-(5-methoxy-9-oxo-2-{[(acetyl)oxy]methyl}-2,3-dihydropyrano[3,2-h][1,4]benzodioxin-3-yl)phenolate; 7-methoxy-4-oxo-2-(4-hydroxyphenyl)-4H-chromene-5-oxide; 2-(5-hydroxy-7-methoxy-4-oxo-4H-chromen-2-yl)phenolate; 3-[2,3-bis(hydroxymethyl)-4-(3-hydroxyphenyl)butyl]phenolate; 2,3-dihydroxy-5-({[5,7-dihydroxy-2-(3,4-dihydroxyphenyl)-3,4-dihydro-2H-chromen-3-yl]oxy}carbonyl)phenolate; 2,6-dihydroxy-4-({[5,7-dihydroxy-2-(3,4-dihydroxyphenyl)-3,4-dihydro-2H-chromen-3-yl]oxy}carbonyl)phenolate; 7-hydroxy-2-(3,4-dihydroxyphenyl)-3-{[(3,4,5-trihydroxyphenyl)carbonyl]oxy}-3,4-dihydro-2H-chromene-5-oxide; 5-hydroxy-2-(3,4-dihydroxyphenyl)-3-{[(3,4,5-trihydroxyphenyl)carbonyl]oxy}-3,4-dihydro-2H-chromene-7-oxide; 2-hydroxy-4-(5,7-dihydroxy-3-{[(3,4,5-trihydroxyphenyl)carbonyl]oxy}-3,4-dihydro-2H-chromen-2-yl)phenolate; 2-hydroxy-5-(5,7-dihydroxy-3-{[(3,4,5-trihydroxyphenyl)carbonyl]oxy}-3,4-dihydro-2H-chromen-2-yl)phenolate; 7-hydroxy-3-methoxy-4-oxo-2-(4-methoxyphenyl)-4H-chromene-5-oxide; 5-hydroxy-3-methoxy-4-oxo-2-(4-methoxyphenyl)-4H-chromene-7-oxide; 15,16,17-trihydroxy-13-methyl-6,7,8,9,11,12,14,15,16,17-decahydrocyclopenta[a]phenanthrene-3-oxide; 7-hydroxy-6-methoxy-4-oxo-2-(3,4-dimethoxyphenyl)-4H-chromene-5-oxide; 5-hydroxy-6-methoxy-4-oxo-2-(3,4-dimethoxyphenyl)-4H-chromene-7-oxide; 1-hydroxy-9-oxoxanthene-7-oxide; 8-hydroxy-9-oxoxanthene-2-oxide; 4b,8,8-trimethyl-2-isopropyl-5,6,7,8a,9,10-hexahydrophenanthren-3-oxide; 8-[(3,7-dimethyloct-2-enyl)oxy]-2-oxo-2H-chromene-7-oxide; 3-hydroxy-2-(3,4-dihydroxyphenyl)-3,4-dihydro-2H-chromene-7-oxide; 2-hydroxy-4-(3,7-dihydroxy-3,4-dihydro-2H-chromen-2-yl)phenolate; 2-hydroxy-5-(3,7-dihydroxy-3,4-dihydro-2H-chromen-2-yl)phenolate; 2,7,8-trimethyl-2-(4,8,12-trimethyltrideca-3,7,11-trienyl)-3,4-dihydro-2H-chromene-6-oxide; 3-hydroxy-4-oxo-2-(4-hydroxyphenyl)-2,3-dihydro-4H-chromene-7-oxide; 4-(3,7-dihydroxy-4-oxo-2,3-dihydro-4H-chromen-2-yl)phenolate; 7-methoxy-4-oxo-2-(4-hydroxyphenyl)-4H-chromene-5-oxide; 4-(5-hydroxy-7-methoxy-4-oxo-4H-chromen-2-yl)phenolate; 4-oxo-2-(4-hydroxy-3-methoxyphenyl)-4H-chromene-7-oxide; 2-methoxy-4-(7-hydroxy-4-oxo-4H-chromen-2-yl)phenolate; 4-[6,9,17,19,21-pentahydroxy-13-(4-hydroxyphenyl)-4,12,14-trioxapentacyclo[11.7.1.0$^{2,11}$.0$^{3,8}$.0$^{15,20}$]henicosa-2(11),3(8),9,15,17,19-hexaen-5-yl]phenolate; 4-[6,9,17,19,21-pentahydroxy-5-(4-hydroxyphenyl)-4,12,14-trioxapentacyclo[11.7.1.0$^{2,11}$.0$^{3,8}$.0$^{15,20}$]henicosa-2(11),3(8),9,15,17,19-hexaen-13-yl]phenolate; 6,17,19,21-tetrahydroxy-5,13-bis(4-hydroxyphenyl)-4,12,14-trioxapentacyclo[11.7.1.0$^{2,11}$.0$^{3,8}$.0$^{15,20}$]henicosa-2(11),3(8),9,15,17,19-hexaene-9-oxide; 6,9,19,21-tetrahydroxy-5,13-bis(4-hydroxyphenyl)-4,12,14-trioxapentacyclo[11.7.1.0$^{2,11}$.0$^{3,8}$.0$^{15,20}$]henicosa-2(11),3(8),9,15,17,19-hexaene-17-oxide; 6,9,17,21-tetrahydroxy-5,13-bis(4-hydroxyphenyl)-4,12,14-trioxapentacyclo[11.7.1.0$^{2,11}$.0$^{3,8}$.0$^{15,20}$]henicosa-2(11),3(8),9,15,17,19-hexaene-19-oxide; 3-(5-hydroxy-2,2-dimethyl-2H-chromen-8-yl)-2H-chromene-7-oxide; 2,2-dimethyl-8-(7-hydroxy-2H-chromen-3-yl)-2H-chromene-5-oxide; 3-hydroxy-4-[8,8-dimethyl-3,4-dihydro-2H-pyrano[2,3-f]chromen-3-yl]phenolate; 3-hydroxy-6-[8,8-dimethyl-3,4-dihydro-2H-pyrano[2,3-f]chromen-3-yl]phenolate; 6a-hydroxy-2,2-dimethyl-6,11a-dihydroxy-[1]benzofuro[3,2-c]pyrano[2,3-h]chromene-9-oxide; 7a-hydroxy-3,3-dimethyl-6,12a-dihydro-[1]benzofuro[3,2-c]pyrano[3,2-g]chromene-10-oxide; 6a-hydroxy-2-isopropenyl-1,2,6,11a-tetrahydro-[1]benzofuro[3,2-c]furo[3,2-g]chromene-9-oxide; 6a-hydroxy-2-isoprenyl-3-methoxy-6,11a-dihydro-[1]benzofuro[3,2-c]chromene-9-oxide; 3,6a-dihydroxy-6,11a-dihydro-[1]benzofuro[3,2-c]chromene-9-oxide; 6a,9-dihydroxy-6,11a-dihydro-[1]benzofuro[3,2-c]chromene-3-oxide; 6-methoxy-3-(4-hydroxyphenyl)-4-oxo-4H-chromene-7-oxide; 4-(7-hydroxy-6-methoxy-4-oxo-4H-chromen-3-yl)phenolate;

9-hydroxy-2,8-diisoprenyl-1-methoxy-6H-[1]benzofuro[3,2-c]chromene-3-oxide; 3-hydroxy-2,8-diisoprenyl-1-methoxy-6H-[1]benzofuro[3,2-c]chromene-9-oxide; 5,7,8-trihydroxy-4-oxo-2-(3,4-dihydroxyphenyl)-4H-chromene-3-oxide; 3,7,8-trihydroxy-4-oxo-2-(3,4-dihydroxyphenyl)-4H-chromene-5-oxide; 3,5,8-trihydroxy-4-oxo-2-(3,4-dihydroxyphenyl)-4H-chromene-7-oxide; 3,5,7-trihydroxy-4-oxo-2-(3,4-dihydroxyphenyl)-4H-chromene-8-oxide; 2-hydroxy-4-(3,5,7,8-tetrahydroxy-4-oxo-4H-chromen-2-yl)phenolate; 2-hydroxy-5-(3,5,7,8-tetrahydroxy-4-oxo-4H-chromen-2-yl)phenolate; 3-hydroxy-2-(4-hydroxyphenyl)-3,4-dihydro-2H-chromene-7-oxide; 4-(3,7-dihydroxy-3,4-dihydro-2H-chromen-2-yl)phenolate; 4-[(heptyloxy)carbonyl]phenolate; 7-hydroxy-6-methoxy-4-oxo-2-(4-hydroxyphenyl)-4H-chromene-5-oxide; 5-hydroxy-6-methoxy-4-oxo-2-(4-hydroxyphenyl)-4H-chromene-7-oxide; 4-(5,7-dihydroxy-6-methoxy-4-oxo-4H-chromen-2-yl)phenolate; 9-hydroxymethyl-6,6-dimethyl-3-(2-methyloct-2-yl)-6a,7,10,10a-tetrahydro-6H-benzo[c]chromene-1-oxide; 9-hydroxymethyl-6,6-dimethyl-3-(2-methyloct-2-yl)-6a,7,8,9,10,10a-hexahydro-6H-benzo[c]chromene-1-oxide; 3-(6-isopropenyl-3-methylcyclohex-2-enyl)-6-pentyl-1,4-benzoquinone-2-oxide; 2-methoxy-4-(hydroxy-{4-oxo-5-[(4-hydroxy-3-methoxyphenyl)methyl]-3-oxacyclopentyl}methyl)phenolate; 2-methoxy-4-({2-oxo-5-[hydroxy-(4-hydroxy-3-methoxyphenyl)methyl]-3-oxacyclopentyl}methyl)phenolate; 7-hydroxy-6,8-dimethoxy-4-oxo-2-(3,4-dimethoxyphenyl)-4H-chromene-5-oxide; 5-hydroxy-6,8-dimethoxy-4-oxo-2-(3,4-dimethoxyphenyl)-4H-chromene-7-oxide; 7,8-dihydroxy-4-oxo-2-(3,4-dihydroxyphenyl)-4H-chromene-5-oxide; 5,8-dihydroxy-4-oxo-2-(3,4-dihydroxyphenyl)-4H-chromene-7-oxide; 5,7-dihydroxy-4-oxo-2-(3,4-dihydroxyphenyl)-4H-chromene-8-oxide; 2-hydroxy-4-(5,7,8-trihydroxy-4-oxo-4H-chromen-2-yl)phenolate; 2-hydroxy-5-(5,7,8-trihydroxy-4-oxo-4H-chromen-2-yl)phenolate; 2-iodo-6-methoxy-4-(2-oxo-2-{[(13-benzyl-6-hydroxy-4,17-dimethyl-5-oxo-15-isopropenyl-12,14,18-trioxapentacyclo[11.4.1.0$^{1,10}$0.$^{2,6}$.0$^{11,15}$]octadeca-3,8-dien-8-yl)methyl]oxy}ethyl)phenolate; 8-oxo-7-(4-hydroxyphenyl)-[1,3]diolxolo[4,5-g]chromen-9-oxide; 4-(9-hydroxy-8-oxo-[1,3]diolxolo[4,5-g]chromen-7-yl)phenolate; 10,11-dihydroxy-3,3-dimethyl-7-oxopyrano[2,3-c]xanthen-6-oxide; 6,11-dihydroxy-3,3-dimethyl-7-oxopyrano[2,3-c]xanthen-10-oxide; 6,10-dihydroxy-3,3-dimethyl-7-oxopyrano[2,3-c]xanthen-11-oxide; [3-oxo-3-(2,4-dihydroxyphenyl)prop-1-enyl]phenolate; 3-hydroxy-4-[1-oxo-3-(4-hydroxyphenyl)prop-2-enyl]phenolate; 3-hydroxy-6-[1-oxo-3-(4-hydroxyphenyl)prop-2-enyl]phenolate; 5,7-dihydroxy-4-oxo-2-(4-hydroxy-3-methoxyphenyl)-4H-chromene-3-oxide; 3,7-dihydroxy-4-oxo-2-(4-hydroxy-3-methoxyphenyl)-4H-chromene-5-oxide; 3,5-dihydroxy-4-oxo-2-(4-hydroxy-3-methoxyphenyl)-4H-chromene-7-oxide; 2-methoxy-4-(3,5,7-trihydroxy-4-oxo-4H-chromen-2-yl)phenolate; 7-hydroxy-4-oxo-2-(4-methoxyphenyl)-2,3-dihydro-4H-chromene-5-oxide; 5-hydroxy-4-oxo-2-(4-methoxyphenyl)-2,3-dihydro-4H-chromene-7-oxide; 7,8-dihydroxy-4-oxo-2-(4-hydroxyphenyl)-4H-chromene-5-oxide; 5,8-dihydroxy-4-oxo-2-(4-hydroxyphenyl)-4H-chromene-7-oxide; 5,7-dihydroxy-4-oxo-2-(4-hydroxyphenyl)-4H-chromene-8-oxide; 4-(5,7,8-trihydroxy-4-oxo-4H-chromen-2-yl)phenolate; 3,7-dihydroxy-4-oxo-2-[7-hydroxy-3-(hydroxymethyl)-2-(4-hydroxy-3-methoxyphenyl)-2,3-dihydro-1-benzofuran-4-yl]-2,3-dihydro-4H-chromene-5-oxide; 3,5-dihydroxy-4-oxo-2-[7-hydroxy-3-(hydroxymethyl)-2-(4-hydroxy-3-methoxyphenyl)-2,3-dihydro-1-benzofuran-4-yl]-2,3-dihydro-4H-chromene-7-oxide; 2-methoxy-4-[7-hydroxy-3-(hydroxymethyl)-4-(3,5,7-trihydroxy-4-oxo-2,3-dihydro-4H-chromen-2-yl)-2,3-dihydro-1-benzofuran-2-yl]phenolate; 3-(hydroxymethyl)-2-(4-hydroxy-3-methoxyphenyl)-4-(3,5,7-trihydroxy-4-oxo-2,3-dihydro-4H-chromen-2-yl)-1-benzofuran-7-oxide; 8-isoprenyl-5-methoxy-4-oxo-2-(4-hydroxyphenyl)-2,3-dihyro-4H-chromene-7-oxide; 4-(8-isoprenyl-7-hydroxy-5-methoxy-4-oxo-2,3-dihydro-4H-chromen-2-yl)phenolate; 7-hydroxy-6-methoxy-4-oxo-2-(4-hydroxy-3-methoxyphenyl)-4H-chromene-5-oxide; 5-hydroxy-6-methoxy-4-oxo-2-(4-hydroxy-3-methoxyphenyl)-4H-chromene-7-oxide; 2-methoxy-4-(5,7-dihydroxy-6-methoxy-4-oxo-4H-chromen-2-yl)phenolate; 2,3,4,5-tetramethoxy-6-(1-oxo-3-phenylprop-2-enyl)phenolate; 6,6,9-trimethyl-3-(2-phenylprop-2-yl)-6a,7,10,10a-tetrahydro-6H-benzo[c]chromene-1-oxide; 3-hydroxy-4-(3-isoprenyl-5,7-dihydroxy-4-oxo-8-{3-methyl-6-[(2,4-dihydroxyphenyl)carbonyl]-5-(2,4-dihydroxyphenyl)cyclohex-2-enyl]-4H-chromen-2-yl)phenolate; 3-hydroxy-6-(3-isoprenyl-5,7-dihydroxy-4-oxo-8-{3-methyl-6-[(2,4-dihydroxyphenyl)carbonyl]-5-(2,4-dihydroxyphenyl)cyclohex-2-enyl]-4H-chromen-2-yl)phenolate; 3-isoprenyl-7-hydroxy-4-oxo-2-(2,4-dihydroxyphenyl)-8-{3-methyl-6-[(2,4-dihydroxyphenyl)carbonyl]-5-(2,4-dihydroxyphenyl)cyclohex-2-enyl}-4H-chromene-5-oxide; 3-isoprenyl-5-hydroxy-4-oxo-2-(2,4-dihydroxyphenyl)-8-{3-methyl-6-[(2,4-dihydroxyphenyl)carbonyl]-5-(2,4-dihydroxyphenyl)cyclohex-2-enyl}-4H-chromene-7-oxide; 3-hydroxy-4-{3-methyl-6-[(2,4-dihydroxyphenyl)carbonyl]-5-[3-isoprenyl-5,7-dihydroxy-4-oxo-2-(2,4-dihydroxyphenyl)-4H-chromen-8-yl]cyclohex-3-enyl}phenolate; 3-hydroxy-6-{3-methyl-6-[(2,4-dihydroxyphenyl)carbonyl]-5-[3-isoprenyl-5,7-dihydroxy-4-oxo-2-(2,4-dihydroxyphenyl)-4H-chromen-8-yl]cyclohex-3-enyl}phenolate; 3-hydroxy-4-({4-methyl-6-(2,4-dihydroxyphenyl)-2-[3-isoprenyl-5,7-dihydroxy-4-oxo-2-(2,4-dihydroxyphenyl)-4H-chromen-8-yl]cyclohex-3-enyl}carbonyl)phenolate; 3-hydroxy-6-({4-methyl-6-(2,4-dihydroxyphenyl)-2-[3-isoprenyl-5,7-dihydroxy-4-oxo-2-(2,4-dihydroxyphenyl)-4H-chromen-8-yl]cyclohex-3-enyl}carbonyl)phenolate; 2-methoxy-4-{2-(hydroxymethyl)-3-[(4-hydroxy-3-methoxyphenyl)methyl]-5-oxacyclopentyl}phenolate; 2-methoxy-4-{[2-(hydroxymethyl)-3-(4-hydroxy-3-methoxyphenyl)-4-oxacyclopentyl]methyl}phenolate; 5,7-dihydroxy-4-oxo-2-(4,5-dihydroxy-3-methoxyphenyl)-4H-chromene-3-oxide; 3,7-dihydroxy-4-oxo-2-(4,5-dihydroxy-3-methoxyphenyl)-4H-chromene-5-oxide; 3,5-dihydroxy-4-oxo-2-(4,5-dihydroxy-3-methoxyphenyl)-4H-chromene-7-oxide; 6-hydroxy-2-methoxy-4-(3,5,7-trihydroxy-4-oxo-4H-chromen-2-yl)phenolate; 2-hydroxy-3-methoxy-5-(3,5,7-trihydroxy-4-oxo-4H-chromen-2-yl)phenolate; 7-methoxy-3-oxo-2-[(3,4-dihydroxyphenyl)methylidene]-1-benzofuran-6-oxide; 2-hydroxy-4-[(6-hydroxy-7-methoxy-3-oxo-1-benzofuran-2-ylidene)methyl]phenolate; 2-hydroxy-5-[(6-hydroxy-7-methoxy-3-oxo-1-benzofuran-2-ylidene)methyl]phenolate; 3-hydroxy-2-(4-hydroxy-5-methyl-7-oxo-5,6-dihydro-4H-2-benzofuran-1-yl)phenolate; 3,4-dihydroxy-2-(3,4-dihydroxyphenyl)-3,4-dihydro-2H-chromene-7-oxide; 2-hydroxy-4-(3,4,7-trihydroxy-3,4-dihydro-2H-chromen-2-yl)phenolate; 2-hydroxy-5-(3,4,7-trihydroxy-3,4-dihydro-2H-chromen-2-yl)phenolate; 3,4,7-trihydroxy-2-(4-hydroxyphenyl)-3,4-dihydro-2H-chromene-5-oxide; 3,4,5-trihydroxy-2-(4-hydroxyphenyl)-3,4-dihydro-2H-chromene-7-oxide; 4-(3,4,5,7-tetrahydroxy-3,4-dihydro-2H-chromen-2-yl)phenolate; 4,5,7-trihydroxy-2-(4-hydroxy-3-methoxyphenyl)-4H-chromene-3-oxide; 3,4,7- trihydroxy-2-(4-hydroxy-3-methoxyphenyl)-4H-chromene-5-oxide; 3,4,5-trihydroxy-2-(4-hydroxy-3-methoxyphenyl)-4H-chromene-7-oxide; 2-methoxy-4-(3,4,5,7-tetrahydroxy-4H-chromen-2-yl)phenolate; 4-oxo-2-(4-hydroxyphenyl)-2,3-dihydro-4H-chromen-7-oxide; 4-(7-hydroxy-4-oxo-2,3-dihydro-4H-chromen-2-yl)phenolate; 4,7-dihydroxy-2-(3,4-dihydroxyphenyl)-3,4-dihydro-2H-chromene-5-oxide; 4,5-dihydroxy-2-(3,4-dihydroxyphenyl)-3,4-dihydro-2H-chromene-7-oxide; 2-hydroxy-4-(4,5,7-trihydroxy-3,4-dihydro-2H-chromen-2-yl)phenolate; 2-hydroxy-5-(4,5,7-trihydroxy-3,4-dihydro-2H-chromen-2-yl)phenolate; 7-hydroxy-6-isoprenyl-4-oxo-3-(2,4-dihydroxyphenyl)-4H-chromene-5-oxide; 5-hydroxy-6-isoprenyl-4-oxo-3-(2,4-dihydroxyphenyl)-4H-chromene-7-oxide; 3-hydroxy-4-(5,7-dihydroxy-6-isoprenyl-4-oxo-4H-chromen-3-yl)phenolate; 3-hydroxy-6-(5,7-dihydroxy-6-isoprenyl-4-oxo-4H-chromen-3-yl)phenolate; 2-methoxy-4-[4-(1,3-benzodioxol-5-yl)-2,3-dimethylbutyl]phenolate; 2-methoxy-4-({3-oxo-2-[(4-hydroxy-3-methoxyphenyl)methyl]-4-oxacyclopentyl}methyl)phenolate; 2-methoxy-4-({2-oxo-5-[(4-hydroxy-3-methoxyphenyl)methyl]-3-oxacyclopentyl}methyl)phenolate; 5,7-dihydroxy-4-oxo-2-(3,5-dihydroxy-4-methoxyphenyl)-4H-chromene-3-oxide; 3,7-dihydroxy-4-oxo-2-(3,5-dihydroxy-4-methoxyphenyl)-4H-chromene-5-oxide; 3,5-dihydroxy-4-oxo-2-(3,5-dihydroxy-4-methoxyphenyl)-4H-chromene-7-oxide; 3-hydroxy-2-methoxy-5-(3,5,7-trihydroxy-4-oxo-4H-chromen-2-yl)phenolate; 7-hydroxy-3-methoxy-2-(3,4-dihydroxyphenyl)-3,4-dihydro-2H-chromene-5-oxide; 5-hydroxy-3-methoxy-2-(3,4-dihydroxyphenyl)-3,4-dihydro-2H-chromene-7-oxide; 2-hydroxy-4-(5,7-dihydroxy-3-methoxy-3,4-dihydro-2H-chromen-2-yl)phenolate; 2-hydroxy-5-(5,7-dihydroxy-3-methoxy-3,4-dihydro-2H-chromen-2-yl)phenolate; 3,4,8-trihydroxy-2-(3,4-dihydroxyphenyl)-3,4-dihydro-2H-chromene-7-oxide; 3,4,7-trihydroxy-2-(3,4-dihydroxyphenyl)-3,4-dihydro-2H-chromene-8-oxide; 2-hydroxy-4-(3,4,7,8-tetrahydroxy-3,4-dihydro-2H-chromen-2-yl)phenolate; 2-hydroxy-5-(3,4,7,8-tetrahydroxy-3,4-dihydro-2H-chromen-2-yl)phenolate; 4-methoxyphenolate; 3,8-dihydroxy-2-(3,4-dihydroxyphenyl)-3,4-dihydro-2H-chromene-7-oxide; 3,7-dihydroxy-2-(3,4-dihydroxyphenyl)-3,4-dihydro-2H-chromene-8-oxide; 2-hydroxy-4-(3,7,8-trihydroxy-3,4-dihydro-2H-chromen-2-yl)phenolate; 2-hydroxy-5-(3,7,8-trihydroxy-3,4-dihydro-2H-chromen-2-yl)phenolate; 5-hydroxy-6,7-dimethoxy-4-oxo-2-(4-methoxyphenyl)-4H-chromene-3-oxide; 3-hydroxy-6,7-dimethoxy-4-oxo-2-(4-methoxyphenyl)-4H-chromene-5-oxide; 3,6-dimethyl-1-(2-methylprop-1-enyl)-2,3-dihydro-1H-indene-5-oxide; 15-hydroxy-16,17-dimethoxy-9-oxotricyclo[12.3.1.1$^{2,6}$]nonadeca-1(17),2,4,6(19),14(18),15-hexaen-3-oxide; 3-hydroxy-16,17-dimethoxy-9-oxotricyclo[12.3.1.1$^{2,6}$]nonadeca-1(17),2,4,6(19),14(18),15-hexaen-15-oxide; 4-hydroxy-5,8-dioxonaphthalene-1-oxide; 6-hydroxy-7-methoxy-4-oxo-2-phenyl-4H-chromene-5-oxide; 5-hydroxy-7-methoxy-4-oxo-2-phenyl-4H-chromene-6-oxide; 7-hydroxy-6-methoxy-4-oxo-2-(3,4-dihydroxyphenyl)-4H-chromene-5-oxide; 5-hydroxy-6-methoxy-4-oxo-2-(3,4-dihydroxyphenyl)-4H-chromene-7-oxide; 2-hydroxy-4-(5,7-dihydroxy-6-methoxy-4-oxo-4H-chromen-2-yl)phenolate; 2-hydroxy-5-(5,7-dihydroxy-6-methoxy-4-oxo-4H-chromen-2-yl)phenolate; 7-hydroxy-6,8-dimethoxy-4-oxo-2-(4-methoxyphenyl)-4H-chromene-5-oxide; 5-hydroxy-6,8-dimethoxy-4-oxo-2-(4-methoxyphenyl)-4H-chromene-7-oxide; 6,7-dihydroxy-3-methoxy-1,4-dioxo-6-methyl-7,8-dihydro-5H-anthracene-9-oxide; 6,7-dihydroxy-4-oxo-2-(4-hydroxy-3-methoxyphenyl)-4H-chromene-5-oxide; 5,7-dihydroxy-4-oxo-2-(4-hydroxy-3-methoxyphenyl)-4H-chromene-6-oxide; 5,6-dihydroxy-4-oxo-2-(4-hydroxy-3-methoxyphenyl)-4H-chromene-7-oxide; 2-methoxy-4-(5,6,7-trihydroxy-4-oxo-4H-chromen-2-yl)phenolate; 7-hydroxy-4-oxo-2-(2,4-dihydroxyphenyl)-4H-chromen-5-oxide; 5-hydroxy-4-oxo-2-(2,4-dihydroxyphenyl)-4H-chromen-7-oxide; 3-hydroxy-4-(5,7-dihydroxy-4-oxo-4H-chromen-2-yl)phenolate; 3-hydroxy-6-(5,7-dihydroxy-4-oxo-4H-chromen-2-yl)phenolate; 7,8-dihydroxy-4-oxo-2-phenyl-4H-chromene-5-oxide; 5,8-dihydroxy-4-oxo-2-phenyl-4H-chromene-7-oxide; 5,7-dihydroxy-4-oxo-2-phenyl-4H-chromene-8-oxide; 3-hydroxy-5-methyl-4-(3-methyl-6-isopropenylcyclohex-2-enyl]phenolate; 2-cycloheptyl-3-hydroxy-5-(2-methyloct-2-yl)phenolate; 2-adamantyl-3-hydroxy-5-(2-methyloct-2-yl)phenolate; 3-hydroxy-2-(3,3-dimethylcyclohexyl)-5-(2-methyloct-2-yl)phenolate; 6,6,9-trimethyl-3-(6-bromohex-2-ynyl)-6a,7,10,10a-tetrahydro-6H-benzo[c]chromene-1-oxide; 2-hydroxy-5-(prop-2-enyl)-3-[4-(prop-2-enyl)phenoxy]phenolate; 2-hydroxy-4-(prop-2-enyl)-6-[4-(prop-2-enyl)phenoxy]phenolate; 3-hydroxy-5-pentylphenolate; 7-hydroxy-8-methoxy-4-oxo-2-(3,4-dihydroxyphenyl)-4H-chromene-5-oxide; 5-hydroxy-8-methoxy-4-oxo-2-(3,4-dihydroxyphenyl)-4H-chromene-7-oxide; 2-hydroxy-4-(5,7-dihydroxy-8-methoxy-4-oxo-4H-chromen-2-yl)phenolate; 2-hydroxy-5-(5,7-dihydroxy-8-methoxy-4-oxo-4H-chromen-2-yl)phenolate; 3,8-dihydroxy-2-(4-hydroxyphenyl)-3,4-dihydro-2H-chromene-7-oxide; 3,7-dihydroxy-2-(4-hydroxyphenyl)-3,4-dihydro-2H-chromene-8-oxide; 4-(3,7,8-trihydroxy-3,4-dihydro-2H-chromen-2-yl)phenolate; 7-hydroxy-4-oxo-3-(3,4-dihydroxyphenyl)-4H-chromene-5-oxide; 5-hydroxy-4-oxo-3-(3,4-dihydroxyphenyl)-4H-chromene-7-oxide; 2-hydroxy-4-(5,7-dihydroxy-4-oxo-4H-chromen-3-yl)phenolate; 2-hydroxy-5-(5,7-dihydroxy-4-oxo-4H-chromen-3-yl)phenolate; 2-phenylphenolate; 2,5-dihydroxy-9,10-dioxoanthracene-1-oxide; 1,5-dihydroxy-9,10-dioxoanthracene-2-oxide; 5,6-dihydroxy-9,10-dioxoanthracene-1-oxide; 2,8-dihydroxy-9,10-dioxoanthracene-1-oxide; 1,8-dihydroxy-9,10-dioxoanthracene-2-oxide; 7,8-dihydroxy-9,10-dioxo-anthracene-1-oxide; 3,7-dimethoxy-4-oxo-2-(4-hydroxy-3-methoxyphenyl)-4H-chromene-5-oxide; 2-methoxy-4-(5-hydroxy-3,7-dimethoxy-4-oxo-4H-chromen-2-yl)phenolate; 5,7-dihydroxy-6-methoxy-4-oxo-2-(3,4-dihydroxyphenyl)-4H-chromene-3-oxide; 3,7-dihydroxy-6-methoxy-4-oxo-2-(3,4-dihydroxyphenyl)-4H-chromene-5-oxide; 3,5-dihydroxy-6-methoxy-4-oxo-2-(3,4-dihydroxyphenyl)-4H-chromene-7-oxide; 2-hydroxy-4-(3,5,7-trihydroxy-6-methoxy-4-oxo-4H-chromen-2-yl)phenolate; 2-hydroxy-5-(3,5,7-trihydroxy-6-methoxy-4-oxo-4H-chromen-2-yl)phenolate; 6-hydroxy-7-methoxy-4-oxo-2-(3,4-dihydroxyphenyl)-4H-chromene-5-oxide; 5-hydroxy-7-methoxy-4-oxo-2-(3,4-dihydroxyphenyl)-4H-chromene-6-oxide; 2-hydroxy-4-(5,6-dihydroxy-7-methoxy-4-oxo-4H-chromen-2-yl)phenolate; 2-hydroxy-5-(5,6-dihydroxy-7-methoxy-4-oxo-4H-chromen-2-yl)phenolate; 6,6,9-trimethyl-3-(2-phenylethyl)-6a,7,8,10a-tetrahydro-6H-benzo[c]chromene-1-oxide; 2-methoxy-4-[(N-{12-[1-oxo-2-phenyl)ethyl]octadec-9-enyl}amino)methyl]phenolate; 4-hydroxy-2-methyl-3-(3,7,11,15-tetramethylhexadec-2-enyl)naphthalene-1-oxide; 4-hydroxy-3-methyl-2-(3,7,11,15-tetramethylhexadec-2-enyl)naphthalene-1-oxide; 2-hydroxy-4-[2-(3,5-dihydroxyphenyl)ethenyl]phenolate; 2-hydroxy-5-[2-(3,5-dihydroxyphenyl)ethenyl]phenolate; 3-hydroxy-5-[2-(3,4-dihydroxyphenyl)ethenyl]phenolate; 7-methoxy-4-oxo-2-(3-hydroxy-4-methoxyphenyl)-4H-chromene-5-oxide;

2-methoxy-5-(5-hydroxy-7-methoxy-4-oxo-4H-chromen-2-yl)phenolate; 3,7-dihydroxy-4-oxo-2-phenyl-2,3-dihydro-4H-chromene-5-oxide; 3,5-dihydroxy-4-oxo-2-phenyl-2,3-dihydro-4H-chromene-7-oxide; 7-hydroxy-4-oxo-2-phenyl-2,3-dihydro-4H-chromene-5-oxide; 5-hydroxy-4-oxo-2-phenyl-2,3-dihydro-4H-chromene-7-oxide; 2-methoxy-4-[6-(4-hydroxy-3-methoxyphenyl)-1,3,3a,4,6,6a-hexahydrofuro[3,4-c]furan-3-yl]phenolate; 7-methoxy-4-oxo-2-phenyl-2,3-dihydro-4H-chromene-5-oxide; 2,2-dimethyl-6-oxobenzofuro[3,2-c]pyrano[2,3-h]chromene-9-oxide; 6-isoprenyl-8,8-dimethyl-4-oxo-3-(3,4-dihydroxyphenyl)pyrano[2,3-h]-4H-chromene-5-oxide; 2-hydroxy-4-(5-hydroxy-6-isoprenyl-8,8-dimethyl-4-oxopyrano[2,3-h]chromen-3-yl)phenolate; 2-hydroxy-5-(5-hydroxy-6-isoprenyl-8,8-dimethyl-4-oxopyrano[2,3-h]chromen-3-yl)phenolate; 7-hydroxy-6-methyl-4-oxo-2-(4-hydroxyphenyl)-2,3-dihydro-4H-chromene-5-oxide; 5-hydroxy-6-methyl-4-oxo-2-(4-hydroxyphenyl)-2,3-dihydro-4H-chromene-7-oxide; 4-(5,7-dihydroxy-6-methyl-4-oxo-2,3-dihydro-4H-chromen-2-yl)phenolate; 4-oxo-2-(4-methoxyphenyl)-4H-chromene-7-oxide; 8-hydroxy-4-oxo-2-phenyl-4H-chromene-5-oxide; 5-hydroxy-4-oxo-2-phenyl-4H-chromene-8-oxide; 4-oxo-2-phenyl-4H-chromene-5-oxide; 2-oxo-3-[(2-hydroxyphenyl)methyl]-7-(2-methylnonan-2-yl)-2H-chromene-5-oxide; 2-{[5-hydroxy-2-oxo-7-(2-methylnonan-2-yl)-2H-chromen-3-yl]methyl}phenolate; 4-methoxy-2-(prop-1-enyl)phenolate; 7-hydroxy-8-methoxy-4-oxo-3-(4-hydroxyphenyl)-4H-chromene-5-oxide; 5-hydroxy-8-methoxy-4-oxo-3-(4-hydroxyphenyl)-4H-chromene-7-oxide; 4-(5,7-dihydroxy-8-methoxy-4-oxo-4H-chromen-3-yl)phenolate; 4-[2-(3,5-dimethoxyphenyl)ethenyl]phenolate; 3-hydroxy-9,10-dioxoanthracene-1-oxide; 4-hydroxy-9,10-dioxoanthracene-2-oxide; 4-hydroxy-9,10-dioxoanthracene-1-oxide; 2-methoxy-4-(2-oxo-2-{[(13-benzyl-6-hydroxy-4,17-dimethyl-5-oxo-15-isopropenyl-12,14,18-trioxapentacyclo[11.4.1.0$^{1,10}$.0$^{2,6}$.0$^{11,15}$]octadeca-3,8-dien-8-yl)methyl]oxy}ethyl)phenolate; 8-hydroxy-4-oxo-3-(4-methoxyphenyl)-4H-chromene-7-oxide; 7-hydroxy-4-oxo-3-(4-methoxyphenyl)-4H-chromene-8-oxide; 5-hydroxy-7-methoxy-4-oxo-2-(4-hydroxy-3-methoxyphenyl)-4H-chromene-3-oxide; 3-hydroxy-7-methoxy-4-oxo-2-(4-hydroxy-3-methoxyphenyl)-4H-chromene-5-oxide; 2-methoxy-4-(3,5-dihydroxy-7-methoxy-4-oxo-4H-chromen-2-yl)phenolate; 3-hydroxy-2-(3,4,5-trihydroxyphenyl)-3,4-dihydro-2H-chromene-7-oxide; 2,3-dihydroxy-5-(3,7-dihydroxy-3,4-dihydro-2H-chromen-2-yl)phenolate; 2,6-dihydroxy-4-(3,7-dihydroxy-3,4-dihydro-2H-chromen-2-yl)phenolate; 7-methoxy-4-oxo-2-(4-hydroxyphenyl)-2,3-dihydro-4H-chromene-5-oxide; 4-(5-hydroxy-7-methoxy-4-oxo-2,3-dihydro-4H-chromen-2-yl)phenolate; 3,4-dihydroxy-3-[(3,4-dihydroxyphenyl)methyl]-2,4-dihydro-3H-chromene-7-oxide; 2-hydroxy-4-[(3,4,7-trihydroxy-2,4-dihydro-3H-chromen-3-yl)methyl]phenolate; 2-hydroxy-5-[(3,4,7-trihydroxy-2,4-dihydro-3H-chromen-3-yl)methyl]phenolate; 7-hydroxy-6,8-dimethoxy-4-oxo-2-(5-hydroxy-3,4-dimethoxyphenyl)-4H-chromene-5-oxide; 5-hydroxy-6,8-dimethoxy-4-oxo-2-(5-hydroxy-3,4-dimethoxyphenyl)-4H-chromene-7-oxide; 2,3-dimethoxy-5-(5,7-dihydroxy-6,8-dimethoxy-4-oxo-4H-chromen-2-yl)phenolate; 5,7-dihydroxy-3',4'-dimethoxy-4-oxospiro[2H-chromene-3,7'-bicyclo[4.2.0]octa-1,3,5-triene]-2'-oxide; 2',7'-dihydroxy-3',4'-dimethoxy-4-oxospiro[2H-chromene-3,7'-bicyclo[4.2.0]octa-1,3,5-triene]-5-oxide; 2',5-dihydroxy-3',4'-dimethoxy-4-oxospiro[2H-chromene-3,7'-bicyclo[4.2.0]octa-1,3,5-triene]-7-oxide; 6,7-dimethoxy-4-oxo-3-[(3,4-dihydroxyphenyl)methyl]-2,3-dihydro-4H-chromene-5-oxide; 2-hydroxy-4-[(5-hydroxy-6,7-dimethoxy-4-oxo-2,3-dihydro-4H-chromen-3-yl)methyl]phenolate; 2-hydroxy-5-[(5-hydroxy-6,7-dimethoxy-4-oxo-2,3-dihydro-4H-chromen-3-yl)methyl]phenolate; 2-methoxy-4-[2,3-bis(hydroxymethyl)-4-(4-hydroxy-3-methoxyphenyl)butyl]phenolate; 6,17,19,21-tetrahydroxy-5,13-bis(4-hydroxyphenyl)-7-[3,5,7-trihydroxy-2-(4-hydroxyphenyl)-3,4-dihydro-2H-chromen-8-yl]-4,12,14-trioxapentacyclo[11.7.1.0$^{2,11}$.0$^{3,8}$.0$^{15,20}$]henicosa-2(11),3(8),9,15,17,19-hexaene-9-oxide; 6,9,19,21-tetrahydroxy-5,13-bis(4-hydroxyphenyl)-7-[3,5,7-trihydroxy-2-(4-hydroxyphenyl)-3,4-dihydro-2H-chromen-8-yl]-4,12,14-trioxapentacyclo[11.7.1.0$^{2,11}$.0$^{3,8}$.0$^{15,20}$]henicosa-2(11),3(8),9,15,17,19-hexaene-17-oxide; 6,9,17,21-tetrahydroxy-5,13-bis(4-hydroxyphenyl)-7-[3,5,7-trihydroxy-2-(4-hydroxyphenyl)-3,4-dihydro-2H-chromen-8-yl]-4,12,14-trioxapentacyclo[11.7.1.0$^{2,11}$0.0$^{3,8}$.0$^{15,20}$]henicosa-2(11),3(8),9,15,17,19-hexaene-19-oxide; {6,9,17,19,21-pentahydroxy-13-(4-hydroxyphenyl)-7-[3,5,7-trihydroxy-2-(4-hydroxyphenyl)-3,4-dihydro-2H-chromen-8-yl]-4,12,14-trioxapentacyclo[11.7.1.0$^{2,11}$.0$^{3,8}$.0$^{15,20}$]henicosa-2(11),3(8),9,15,17,19-hexaen-5-yl}phenolate; {6,9,17,19,21-pentahydroxy-5-(4-hydroxyphenyl)-7-[3,5,7-trihydroxy-2-(4-hydroxyphenyl)-3,4-dihydro-2H-chromen-8-yl]-4,12,14-trioxapentacyclo[11.7.1.0$^{2,11}$.0$^{3,8}$.0$^{15,20}$]henicosa-2(11),3(8),9,15,17,19-hexaen-13-yl}phenolate; 3,7-dihydroxy-2-(4-hydroxyphenyl)-8-{6,9,17,19,21-pentahydroxy-5,13-bis(4-hydroxyphenyl)-4,12,14-trioxapentacyclo[11.7.1.0$^{2,11}$.0$^{3,8}$.0$^{15,20}$]henicosa-2(11),3(8),9,15,17,19-hexaen-7-yl}-3,4-dihydro-2H-chromene-5-oxide; 7,8-dimethoxy-4-oxo-2-(2,3,4-trimethoxyphenyl)-4H-chromene-5-oxide; 1,3-benzodioxol-5-oxide; 2-methoxy-4-(3-oxodec-4-enyl)phenolate; 3,7-dihydroxy-4-oxo-2-[7-hydroxy-3-(hydroxymethyl)-2-(4-hydroxy-3-methoxyphenyl)-2,3-dihydro-1-benzofuran-5-yl]-2,3-dihydro-4H-chromene-5-oxide; 3,5-dihydroxy-4-oxo-2-[7-hydroxy-3-(hydroxymethyl)-2-(4-hydroxy-3-methoxyphenyl)-2,3-dihydro-1-benzofuran-5-yl]-2,3-dihydro-4H-chromene-7-oxide; 3-(hydroxymethyl)-5-(3,5,7-trihydroxy-4-oxo-2,3-dihydro-4H-chromen-2-yl)-2-(4-hydroxy-3-methoxyphenyl)-2,3-dihydro-1-benzofuran-7-oxide; 2-methoxy-4-[7-hydroxy-3-(hydroxymethyl)-5-(3,5,7-trihydroxy-4-oxo-2,3-dihydro-4H-chromen-2-yl)-2-(4-hydroxy-3-methoxyphenyl)-2,3-dihydro-1-benzofuran-2-yl]phenolate; 3,7-dihydroxy-4-oxo-2-{3-hydroxy-2-oxo-10-(4-hydroxy-3-methoxyphenyl)-4-oxatricyclo[4.3.1.0$^{3,7}$]dec-8-en-8-yl}-2,3-dihydro-4H-chromene-5-oxide; 3,5-dihydroxy-4-oxo-2-{3-hydroxy-2-oxo-10-(4-hydroxy-3-methoxyphenyl)-4-oxatricyclo[4.3.1.0$^{3,7}$]dec-8-en-8-yl}-2,3-dihydro-4H-chromene-7-oxide; 2-methoxy-4-{3-hydroxy-2-oxo-8-(3,5,7-trihydroxy-4-oxo-2,3-dihydro-4H-chromen-2-yl)-4-oxatricyclo[4.3.1.0$^{3,7}$]dec-8-en-10-yl}phenolate; 2,6-dimethoxy-4-(3-hydroxyprop-1-enyl)phenolate; 2-methoxy-4-(3-oxo-3-{[10,13-dimethyl-17-(5-isopropylhept-2-yl)-2,3,4,5,6,7,8,9,11,12,14,15,16,17-tetradecahydro-1H-cyclopenta[a]phenanthren-3-yl]oxy}prop-1-enyl)phenolate; 2-methoxy-4-(3-oxo-3-{[10,13-dimethyl-17-(5-isopropylhept-2-yl)-2,3,4,7,8,9,11,12,14,15,16,17-dodecahydro-1H-cyclopenta[a]phenanthren-3-yl]oxy}prop-1-enyl)phenolate; 3-hydroxy-2-isoprenyl-4-{1-oxo-3-[4-hydroxy-3,5-bis(isoprenyl)phenyl]prop-2-enyl}phenolate; 3-hydroxy-2-isoprenyl-6-{1-oxo-3-[4-hydroxy-3,5-bis(isoprenyl)phenyl]prop-2-enyl}phenolate; 2,6-bis(isoprenyl)-4-[3-oxo-3-(2,4-dihydroxy-3-isoprenylphenyl)prop-1-enyl]phenolate; 7-hydroxy-2-(2,4-dihydroxyphenyl)-4-oxo-8-(2-isopropenyl-5-methylhex-4-enyl)-2,3-dihydro-4H-chromene-5-oxide; 5-hydroxy-2-(2, 4-dihydroxyphenyl)-4-oxo-8-(2-isopropenyl-5-methylhex-4-enyl)-2,3-dihydro-4H-chromene-7-oxide; 3-hydroxy-4-[5,7-dihydroxy-4-oxo-8-(2-isopropenyl-5-methylhex-4-enyl)-2,3-dihydro-4H-chromen-2-yl]phenolate; 3-hydroxy-6-[5,7-dihydroxy-4-oxo-8-(2-isopropenyl-5-methylhex-4-enyl)-2,3-dihydro-4H-chromen-2-yl]phenolate; 6-hydroxy-7-methoxy-4-oxo-2-(4-hydroxyphenyl)-4H-chromene-5-oxide; 5-hydroxy-7-methoxy-4-oxo-2-(4-hydroxyphenyl)-4H-chromene-6-oxide; 4-(5,6-dihydroxy-7-methoxy-4-oxo-4H-chromen-2-yl)phenolate; 5,7-dihydroxy-6-methoxy-4-oxo-2-(4-hydroxy-3-methoxyphenyl)-4H-chromene-3-oxide; 3,7-dihydroxy-6-methoxy-4-oxo-2-(4-hydroxy-3-methoxyphenyl)-4H-chromene-5-oxide; 3,5-dihydroxy-6-methoxy-4-oxo-2-(4-hydroxy-3-methoxyphenyl)-4H-chromene-7-oxide; 2-methoxy-4-(3,5,7-trihydroxy-6-methoxy-4-oxo-4H-chromen-2-yl)phenolate; 3,6,7-trihydroxy-5,8-dioxonaphthalene-1-oxide; 4,6,7-trihydroxy-5,8-dioxonaphthalene-2-oxide; 3,5,7-trihydroxy-1,4-dioxonaphthalene-2-oxide; 3,6,8-trihydroxy-1,4-dioxonaphthalene-2-oxide; 7-methoxy-4-oxo-2-(3,4-dihydroxyphenyl)-2,3-dihydro-4H-chromene-5-oxide; 2-hydroxy-4-(5-hydroxy-7-methoxy-4-oxo-2,3-dihydro-4H-chromen-2-yl)phenolate; 2-hydroxy-5-(5-hydroxy-7-methoxy-4-oxo-2,3-dihydro-4H-chromen-2-yl)phenolate; 2-methoxy-4-(3-oxo-3-{[10,13-dimethyl-17-(5-isopropyl-hept-3-en-2-yl)-2,3,4,7,8,9,11,12,14,15,16,17-dodecahydro-1H-cyclopenta[a]phenanthren-3-yl]oxy}prop-1-enyl)phenolate; 5,7-dimethoxy-3-methyl-4-oxo-2-(4,6-dimethoxy-3,5,11-trimethyltrideca-7,9,11-trienyl)-4H-chromene-8-oxide; 7-hydroxy-6,8-dimethoxy-4-oxo-2-(4-hydroxy-3-methoxyphenyl)-4H-chromene-5-oxide; 5-hydroxy-6,8-dimethoxy-4-oxo-2-(4-hydroxy-3-methoxyphenyl)-4H-chromene-7-oxide; 2-methoxy-4-(5,7-dihydroxy-6,8-dimethoxy-4-oxo-4H-chromen-2-yl)phenolate; 2,6-dimethoxy-4-[(6-(4-hydroxy-3,5-dimethoxyphenyl)-1,3,3a,4,6,6a-hexahydrofuro[3,4-c]furan-3-yl]phenolate; 5,7-dihydroxy-4-oxo-2-(4-hydroxy-3,5-dimethoxyphenyl)-4H-chromene-3-oxide; 3,7-dihydroxy-4-oxo-2-(4-hydroxy-3,5-dimethoxyphenyl)-4H-chromene-5-oxide; 3,5-dihydroxy-4-oxo-2-(4-hydroxy-3,5-dimethoxyphenyl)-4H-chromene-7-oxide; 2,6-dimethoxy-4-(3,5,7-trihydroxy-4-oxo-4H-chromen-2-yl)phenolate; 2,6-dimethoxyphenolate; 3,7-dihydroxy-4-oxo-2-(3,4-dihydroxyphenyl)-2,3-dihydro-4H-chromene-5-oxide; 5,7-dihydroxy-4-oxo-2-(3,4-dihydroxyphenyl)-2,3-dihydro-4H-chromene-7-oxide; 2-hydroxy-4-(3,5,7-trihydroxy-4-oxo-2,3-dihydro-4H-chromen-2-yl)phenolate; 2-hydroxy-5-(3,5,7-trihydroxy-4-oxo-2,3-dihydro-4H-chromen-2-yl)phenolate; 9-hydroxy-2-isopropyl-4b,8,8-trimethyl-3-oxo-6,7,8a,9-tetrahydro-5H-phenanthrene-4-oxide; 7-methoxy-4-oxo-2-phenyl-4H-chromene-5-oxide; 1-oxo-3-[(3,4-dihydroxyphenyl)methylidene]-2-benzofuran-7-oxide; 2-hydroxy-4-[(7-hydroxy-1-oxo-2-benzofuran-3-ylidene)methyl]phenolate; 2-hydroxy-5-[(7-hydroxy-1-oxo-2-benzofuran-3-ylidene)methyl]phenolate; 1-oxo-3-(3,4-dihydroxyphenyl)-3,4-dihydro-1H-isochromen-8-oxide; 2-hydroxy-4-(8-hydroxy-1-oxo-3,4-dihydro-1H-isochromen-3-yl)phenolate; 2-hydroxy-5-(8-hydroxy-1-oxo-3,4-dihydro-1H-isochromen-3-yl)phenolate; 5,5-dimethyl-8-(3-methyloct-2-yl)-2,3-dihydro-1H-thiopyrano[2,3-c]chromene-10-oxide; 4-(2-oxo-2-{[(13-benzyl-6-hydroxy-4,17-dimethyl-5-oxo-15-isopropenyl-12,14,18-trioxapentacyclo[11.4.1.0$^{1,10}$.0$^{2,6}$.0$^{11,15}$]octadeca-3,8-dien-8-yl)methyl]oxy}ethyl)phenolate; 2-methoxy-4-(7-methoxy-4-oxo-4H-chromen-2-yl)phenolate; 7-hydroxy-4-oxo-2-(3,4,5-trihydroxyphenyl)-4H-chromene-5-oxide; 5-hydroxy-4-oxo-2-(3,4,5-trihydroxyphenyl)-4H-chromene-7-oxide; 2,3-dihydroxy-5-(5,7-dihydroxy-4-oxo-4H-chromen-2-yl)phenolate; 2,6-dihydroxy-4-(5,7-dihydroxy-4-oxo-4H-chromen-2-yl)phenolate; 7-hydroxy-4-oxo-2-(4-hydroxy-3,5-dimethoxyphenyl)-4H-chromene-5-oxide; 5-hydroxy-4-oxo-2-(4-hydroxy-3,5-dimethoxyphenyl)-4H-chromene-7-oxide; 2,6-dimethoxy-4-(5,7-dihydroxy-4-oxo-4H-chromen-2-yl)phenolate; 4-hydroxy-2,3-dimethoxy-5-methyl-6-(3,7,11,15,19,23,27,31,35,39-decamethyltetraconta-2,6,10,14,18,22,26,30,34,38-decaenyl)phenolate; 4-hydroxy-2,3-dimethoxy-6-methyl-5-(3,7,11,15,19,23,27,31,35,39-decamethyltetraconta-2,6,10,14,18,22,26,30,34,38-decaenyl)phenolate; 8-hydroxy-6-oxobenzo[c]chromene-3-oxide; 3-hydroxy-6-oxobenzo[c]chromene-8-oxide; 6-oxobenzo[c]chromene-3-oxide; 7-methoxy-4-oxo-2-(4-hydroxy-3-methoxyphenyl)-4H-chromene-5-oxide; 2-methoxy-4-(5-hydroxy-7-methoxy-4-oxo-4H-chromen-2-yl)phenolate; 3,7-dihydroxy-9-methoxy-6-oxo-1-(2,3,7-trihydroxy-9-methoxy-6-oxobenzo[c]chromen-1-yl)benzo[c]chromene-2-oxide; 2,7-dihydroxy-9-methoxy-6-oxo-1-(2,3,7-trihydroxy-9-methoxy-6-oxobenzo[c]chromen-1-yl)benzo[c]chromene-3-oxide; 2,3-dihydroxy-9-methoxy-6-oxo-1-(2,3,7-trihydroxy-9-methoxy-6-oxobenzo[c]chromen-1-yl)benzo[c]chromene-7-oxide; 3,7-dihydroxy-9-methoxy-6-oxo-1-(2,3,7-trihydroxy-9-methoxy-6-oxobenzo[c]chromen-4-yl)benzo[c]chromene-2-oxide; 2,7-dihydroxy-9-methoxy-6-oxo-1-(2,3,7-trihydroxy-9-methoxy-6-oxobenzo[c]chromen-4-yl)benzo[c]chromene-3-oxide; 2,3-dihydroxy-9-methoxy-6-oxo-1-(2,3,7-trihydroxy-9-methoxy-6-oxobenzo[c]chromen-4-yl)benzo[c]chromene-7-oxide; 3,7-dihydroxy-9-methoxy-6-oxo-4-(2,3,7-trihydroxy-9-methoxy-6-oxobenzo[c]chromen-1-yl)benzo[c]chromene-2-oxide; 2,7-dihydroxy-9-methoxy-6-oxo-4-(2,3,7-trihydroxy-9-methoxy-6-oxobenzo[c]chromen-1-yl)benzo[c]chromene-3-oxide; 2,3-dihydroxy-9-methoxy-6-oxo-4-(2,3,7-trihydroxy-9-methoxy-6-oxobenzo[c]chromen-1-yl)benzo[c]chromene-7-oxide; 15,19,25,26-pentahydroxy-9,17-dimethoxy-3-methyl-5,14,21-trioxo-4,22-dioxaheptacyclo[14.10.2.0$^{2,15}$.0$^{3,12}$.0$^{6,11}$.0$^{20,28}$.0$^{23,27}$]octacosa-1(26),6(11),7,9,12,16,18,20(28),23(27),24-decaene-7-oxide; 7,15,25,26-pentahydroxy-9,17-dimethoxy-3-methyl-5,14,21-trioxo-4,22-dioxaheptacyclo[14.10.2.0$^{2,15}$.0$^{3,12}$.0$^{6,11}$.0$^{20,28}$.0$^{23,27}$]octacosa-1(26),6(11),7,9,12,16,18,20(28),23(27),24-decaene-19-oxide; 7,15,19,26-pentahydroxy-9,17-dimethoxy-3-methyl-5,14,21-trioxo-4,22-dioxaheptacyclo[14.10.2.0$^{2,15}$.0$^{3,12}$.0$^{6,11}$.0$^{20,28}$.0$^{23,27}$]octacosa-1(26),6(11),7,9,12,16,18,20(28),23(27),24-decaene-25-oxide; 7,15,19,25-pentahydroxy-9,17-dimethoxy-3-methyl-5,14,21-trioxo-4,22-dioxaheptacyclo[14.10.2.0$^{2,15}$.0$^{3,12}$.0$^{6,11}$.0$^{20,28}$.0$^{23,27}$]octacosa-1(26),6(11),7,9,12,16,18,20(28),23(27),24-decaene-26-oxide; 8,9-dihydroxy-3-methoxy-6-oxo-benzofurano[3,2-c]chromene-1-oxide; 1,9-dihydroxy-3-methoxy-6-oxo-benzofurano[3,2-c]chromene-8-oxide; 1,8-dihydroxy-3-methoxy-6-oxo-benzofurano[3,2-c]chromene-9-oxide; 7-hydroxy-6-isoprenyl-4-oxo-3-(4-hydroxyphenyl)-4H-chromene-5-oxide; 5-hydroxy-6-isoprenyl-4-oxo-3-(4-hydroxyphenyl)-4H-chromene-7-oxide; 4-(5,7-dihydroxy-6-isoprenyl-4-oxo-4H-chromen-3-yl)phenolate; 7,8-dimethoxy-4-oxo-2-(3-hydroxy-2-methoxyphenyl)-4H-chromene-5-oxide; 2-methoxy-3-(5-hydroxy-7,8-dimethoxy-4-oxo-4H-chromen-2-yl)phenolate; 7-hydroxy-8-methoxy-4-oxo-2-phenyl-4H-chromene-5-oxide; 5-hydroxy-8-methoxy-4-oxo-2-phenyl-4H-chromene-7-oxide; 5-hydroxy-6-isoprenyl-3-methoxy-2-[1-oxo-3-(4-hydroxyphenyl)prop-2-enyl]phenolate; 5-hydroxy-6-isoprenyl-3-methoxy-4-[1-oxo-3-(4-hydroxyphenyl)prop-2-enyl]phenolate; 4-[3-oxo- 3-(4,6-dihydroxy-5-isoprenyl-2-methoxyphenyl)prop-1-enyl]phenolate; 6,7,8-trimethoxy-4-oxo-2-(4-hydroxyphenyl)-4H-chromene-5-oxide; 4-(5-hydroxy-6,7,8-trimethoxy-4-oxo-4H-chromen-2-yl)phenolate; 24-hydroxy-7,20-dipropyl-9,13,22,26-tetroxo-8,16,21,30-tetraoxaoctacyclo[15.11.1.1$^{4,28}$.0$^{2,15}$.0$^{3,12}$.0$^{5,10}$.0$^{18,23}$.0$^{25,29}$]triaconta-1,3,5(10),11,14,17(29),18(23),24,27-nonaene-11-oxide; 11-hydroxy-7,20-dipropyl-9,13,22,26-tetroxo-8,16,21,30-tetraoxaoctacyclo[15.11.1.1$^{4,28}$.0$^{2,15}$.0$^{3,12}$.0$^{5,10}$.0$^{18,23}$.0$^{25,29}$]triaconta-1,3,5(10),11,14,17(29),18(23),24,27-nonaene-24-oxide; 6-methoxy-4-oxo-2-(2,6-dimethoxyphenyl)-4H-chromene-5-oxide; 6-(3-hydroxycyclohexyl)-3-(2-methylhept-2-yl)phenolate; 6-(3-hydroxycyclohexyl)-3-(2-methyloct-2-yl)phenolate; 6-(3-hydroxycyclohexyl)-3-(2-methyldec-2-yl)phenolate; 2-methoxy-4-(3-oxotetradec-1,4-dienyl)phenolate; 2-methoxy-4-(3-oxotetradec-4-enyl)phenolate; 2-methoxy-4-(3-oxohexadec-4-enyl)phenolate; 2-methoxy-4-(3-oxooct-4-enyl)phenolate; 2-methoxy-4-(3-oxododec-1,4-dienyl)phenolate; 2-methoxy-4-(3-oxododec-4-enyl) phenolate; 6-hydroxy-9,10-dioxoanthracene-1-oxide; 5-hydroxy-9,10-dioxoanthracene-2-oxide; 4-[7-(4-hydroxyphenyl)-3-oxohepta-1,4,6-trieneyl]phenolate; 4-[7-(4-hydroxyphenyl)-5-oxohepta-1,3,6-trieneyl]phenolate; 9-(hydroxymethyl)-6,6-dimethyl-3-pentyl-6a,7,8,10a-tetrahydro-6H-benzo[c]chromene-1-oxide; 2-methoxy-5-[2-(4-methoxy-6-oxo-6H-pyran-2-yl)ethenyl]phenolate; 2-methoxy-4-[2-(4-methoxy-6-oxo-6H-pyran-2-yl)ethyl]phenolate; 9-hydroxy-6,6-dimethyl-3-pentyl-6a,7,8,9,10,10a-hexahydro-6H-benzo[c]chromene-1-oxide; 4-oxo-2-[3,5-bis(tert-butyl)-4-hydroxyphenyl]-4H-chromene-7-oxide; 2,6-bis(tert-butyl)-4-(7-hydroxy-4-oxo-4H-chromen-2-yl)phenolate; 5,7-dihydroxy-8-isoprenyl-4-oxo-2-(4-methoxyphenyl)-4H-chromene-3-oxide; or the anions of the plurality of anions consist of one, two, or each of 3,7-dihydroxy-8-isoprenyl-4-oxo-2-(4-methoxyphenyl)-4H-chromene-5-oxide; 3,5-dihydroxy-8-isoprenyl-4-oxo-2-(4-methoxyphenyl)-4H-chromene-7-oxide; 4,5-dihydroxy-9,10-dioxoanthracene-2-oxide; 3,8-dihydroxy-9,10-dioxoanthracene-1-oxide; 6,8-dihydroxy-9,10-dioxoanthracene-1-oxide; 4-oxo-2-(4-hydroxyphenyl)-4H-chromene-7-oxide; 4-(7-hydroxy-4-oxo-4H-chromen-2-yl)phenolate; 2-oxo-2H-chromene-4-oxide; 4-(2-oxoethyl)phenolate; 4-chloro-2-[(phenyl)carbonyl]phenolate; 4-methoxy-6-oxo-2-(2-phenylethenyl)-6H-pyran-3-oxide; 5-methoxy-4-oxo-3-(4-hydroxyphenyl)-4H-chromene-7-oxide; 4-(7-hydroxy-5-methoxy-4-oxo-4H-chromen-3-yl)phenolate; 2-phenyl-4-oxo-4H-chromene-6-oxide; 6,7-dihydroxy-4-oxo-2-(3,4-dihydroxyphenyl)-4H-chromene-5-oxide; 5,7-dihydroxy-4-oxo-2-(3,4-dihydroxyphenyl)-4H-chromene-6-oxide; 5,6-dihydroxy-4-oxo-2-(3,4-dihydroxyphenyl)-4H-chromene-7-oxide; 2-hydroxy-4-(5,6,7-trihydroxy-4-oxo-4H-chromen-2-yl)phenolate; 2-hydroxy-5-(5,6,7-trihydroxy-4-oxo-4H-chromen-2-yl)phenolate; 8-hydroxy-4-oxo-2-phenyl-4H-chromene-7-oxide; 7-hydroxy-4-oxo-2-phenyl-4H-chromene-8-oxide; 4-(8-isoprenyl-5,7-dimethoxy-4-oxo-2,3-dihydro-4H-chromen-2-yl)phenolate; 4-(8-isoprenyl-5-methoxy-4-oxo-7-pentyloxy-2,3-dihydro-4H-chromen-2-yl)phenolate; 8,9-dihydroxy-3-methylanthracene-1-oxide; 8,9-dihydroxy-6-methylanthracene-1-oxide; 1,8-dihydroxy-3-methylanthracene-9-oxide; 6-[3-(1,3-benzodioxol-5-yl)-1,3,3a,4,6,6a-hexahydrofuro[3,4-c]furan-6-yl]-1,3-benzodioxol-5-oxide; 6-methoxy-2-[(4-methoxy-3,5-dimethylpyridin-2-yl)methylsulfinyl]-1,3-benzimidazole; 3-[2-(N,N-dimethylamino)ethyl]-1H-indol-4-oxide; 2-geranyl-3-hydroxy-5-pentylphenolate; 3-hydroxy-2-(6-isopropenyl-3-methylcyclohex-2-enyl)-5-pentylphenolate; 3-hydroxy-2-(6-isopropenyl-3-methylcyclohex-3-enyl)-5-pentylphenolate; 6,6,9-trimethyl-3-pentyl-6a,7,8,10a-tetrahydro-6H-benzo[c]chromene-1-oxide; 6,6,9-trimethyl-3-pentyl-6a,7,10,10a-tetrahydro-6H-benzo[c]chromene-1-oxide; and 6,6,9-trimethyl-3-pentyl-6H-benzo[c]chromene-1-oxide. Molecular forms of the anions of this paragraph are described, for example, in PCT Patent Application Publication No. WO 2022/182527 A1.

Various aspects of this disclosure relate to a composition described anywhere in this document, for use to manufacture a medicament.

Various aspects of this disclosure relate to a composition described anywhere in this document, for use to manufacture a medicament, wherein manufacturing the medicament comprises combining the composition with an aqueous composition that comprises water at a concentration of at least 50 molar.

Various aspects of this disclosure relate to a container, comprising a chamber that contains a composition described anywhere in this document. In some embodiments, the container is in fluid communication with air; and the container inhibits fluid communication between the composition and the air.

In some embodiments, the chamber contains at least 100 milligrams of the composition. In some embodiments, the chamber contains at least 200 milligrams of the composition. In some embodiments, the chamber contains at least 400 milligrams of the composition. In some embodiments, the chamber contains at least 800 milligrams of the composition. In some embodiments, the chamber contains at least 1600 milligrams of the composition.

In some embodiments, the chamber contains no greater than 256 kilograms of the composition. In some embodiments, the chamber contains no greater than 128 kilograms of the composition. In some embodiments, the chamber contains no greater than 64 kilograms of the composition. In some embodiments, the chamber contains no greater than 32 kilograms of the composition. In some embodiments, the chamber contains no greater than 16 kilograms of the composition. In some embodiments, the chamber contains no greater than 8 kilograms of the composition. In some embodiments, the chamber contains no greater than 4 kilograms of the composition. In some embodiments, the chamber contains no greater than 2 kilograms of the composition. In some embodiments, the chamber contains no greater than 1 kilogram of the composition. In some embodiments, the chamber contains no greater than 640 grams of the composition. In some embodiments, the chamber contains no greater than 320 grams of the composition. In some embodiments, the chamber contains no greater than 160 grams of the composition. In some embodiments, the chamber contains no greater than 80 grams of the composition. In some embodiments, the chamber contains no greater than 40 grams of the composition. In some embodiments, the chamber contains no greater than 20 grams of the composition. In some embodiments, the chamber contains no greater than 10 grams of the composition. In some embodiments, the chamber contains no greater than 6 grams of the composition.

In some embodiments, the composition comprises a gas phase at a concentration of no greater than 1 percent by mass. In some embodiments, the composition comprises a gas phase at a concentration of no greater than 0.8 percent by mass. In some embodiments, the composition comprises a gas phase at a concentration of no greater than 0.6 percent by mass. In some embodiments, the composition comprises a gas phase at a concentration of no greater than 0.4 percent by mass. In some embodiments, the composition comprises a gas phase at a concentration of no greater than 0.2 percent by mass.

In some embodiments, the composition comprises a gas phase that lacks a partial pressure of the solvent that is greater than 1600 pascals. In some embodiments, the composition comprises a gas phase that lacks a partial pressure of the solvent that is greater than 800 pascals. In some embodiments, the composition comprises a gas phase that lacks a partial pressure of the solvent that is greater than 400 pascals. In some embodiments, the composition comprises a gas phase that lacks a partial pressure of the solvent that is greater than 200 pascals. In some embodiments, the composition comprises a gas phase that lacks a partial pressure of the solvent that is greater than 100 pascals. In some embodiments, the composition comprises a gas phase that lacks a partial pressure of the solvent that is greater than 50 pascals.

In some embodiments, the composition comprises a gas phase that lacks a partial pressure of molecular oxygen that is greater than 20 kilopascals. In some embodiments, the composition comprises a gas phase that lacks a partial pressure of molecular oxygen that is greater than 10 kilopascals. In some embodiments, the composition comprises a gas phase that lacks a partial pressure of molecular oxygen that is greater than 5 kilopascals. In some embodiments, the composition comprises a gas phase that lacks a partial pressure of molecular oxygen that is greater than 2 kilopascals. In some embodiments, the composition comprises a gas phase that lacks a partial pressure of molecular oxygen that is greater than 1 kilopascal.

In some embodiments, the composition lacks an amount by mole of molecular oxygen that is greater than the amount by mole of the anion in the composition. In some embodiments, the composition lacks an amount by mole of molecular oxygen that is greater than 50 percent of the amount by mole of the anion in the composition. In some embodiments, the composition lacks an amount by mole of molecular oxygen that is greater than 25 percent of the amount by mole of the anion in the composition. In some embodiments, the composition lacks an amount by mole of molecular oxygen that is greater than 10 percent of the amount by mole of the anion in the composition. In some embodiments, the composition lacks an amount by mole of molecular oxygen that is greater than 5 percent of the amount by mole of the anion in the composition. In some embodiments, the composition lacks an amount by mole of molecular oxygen that is greater than 2 percent of the amount by mole of the anion in the composition.

Various aspects of this disclosure relate to a method to produce a pH-buffered composition, comprising providing the composition described anywhere in this document; providing an aqueous composition that comprises water at a concentration of at least 10 molar; and combining an amount of the composition with an amount of the aqueous composition to produce the pH-buffered composition.

Various aspects of this disclosure relate to a method to produce a pH-buffered composition, comprising providing the container described anywhere in this document; providing an aqueous composition that comprises water at a concentration of at least 10 molar; and combining an amount of the composition with an amount of the aqueous composition to produce the pH-buffered composition.

In some embodiments, the composition comprises water at a concentration of at least 20 molar. In some embodiments, the composition comprises water at a concentration of at least 30 molar. In some embodiments, the composition comprises water at a concentration of at least 40 molar. In some embodiments, the composition comprises water at a concentration of at least 50 molar.

In some embodiments, the method comprises combining at least 100 milligrams of the composition with the aqueous composition. In some embodiments, the method comprises combining at least 200 milligrams of the composition with the aqueous composition. In some embodiments, the method comprises combining at least 400 milligrams of the composition with the aqueous composition. In some embodiments, the method comprises combining at least 800 milligrams of the composition with the aqueous composition. In some embodiments, the method comprises combining at least 1600 milligrams of the composition with the aqueous composition.

In some embodiments, the method comprises combining no greater than 12 grams of the composition with the aqueous composition. In some embodiments, the method comprises combining no greater than 6 grams of the composition with the aqueous composition.

In some embodiments, the method comprises combining at least 100 milliliters of the aqueous composition with the composition. In some embodiments, the method comprises combining at least 200 milliliters of the aqueous composition with the composition.

In some embodiments, the method comprises combining no greater than 1200 milliliters of the aqueous composition with the composition. In some embodiments, the method comprises combining no greater than 600 milliliters of the aqueous composition with the composition.

In some embodiments, the method comprises combining the composition and the aqueous composition at a ratio such that the pH-buffered composition has a pH of at least 7.2. In some embodiments, the method comprises combining the composition and the aqueous composition at a ratio such that the pH-buffered composition has a pH of at least 7.4. In some embodiments, the method comprises combining the composition and the aqueous composition at a ratio such that the pH-buffered composition has a pH of at least 7.6. In some embodiments, the method comprises combining the composition and the aqueous composition at a ratio such that the pH-buffered composition has a pH of at least 7.8. In some embodiments, the method comprises combining the composition and the aqueous composition at a ratio such that the pH-buffered composition has a pH of at least 8.

In some embodiments, the method comprises combining the composition and the aqueous composition at a ratio such that the pH-buffered composition has a pH of no greater than 10.6. In some embodiments, the method comprises combining the composition and the aqueous composition at a ratio such that the pH-buffered composition has a pH of no greater than 10.4. In some embodiments, the method comprises combining the composition and the aqueous composition at a ratio such that the pH-buffered composition has a pH of no greater than 10.2. In some embodiments, the method comprises combining the composition and the aqueous composition at a ratio such that the pH-buffered composition has a pH of no greater than 10.

THE EXAMPLE

Manufacturing and packaging a composition comprising a buffer, a conjugate acid, an excipient, an anion, and a solvent. 31.117 kilograms of coarsely-ground xylitol (excipient) and 15.559 kilograms of finely-ground xylitol (excipient) are added to a container to which 500 grams of sodium carbonate (buffer) is then added. The two different sizes of xylitol improve pouring of a composition made from the xylitol. Sugar alcohols such as xylitol are utilized because they are stable under alkaline conditions.

The xylitol (excipient) and sodium carbonate (buffer) are transferred into an industrial mixer in a glovebox under an inert gas (such as argon or nitrogen) to purge oxygen from the excipient and buffer. The (excipient) and sodium carbonate (buffer) are mixed together with the industrial mixer until homogenized to produce a solid phase. 105.263 grams of 95-percent-pure cannabigerol (molecular form of an anion) and 306.122 grams of 98-percent-pure cannabidiol (molecular form of an anion) are dissolved in 2.125 kilograms of propylene glycol (solvent) in the glovebox under the inert gas to produce a liquid phase. 287.5 grams of distilled water (cosolvent) is added to the liquid phase and mixed until dissolved.

The liquid phase is added to the industrial mixer and mixed with the solid phase to produce a composition. The composition is then packaged into containers.

The carbonate deprotonates the cannabigerol and cannabidiol into 3-hydroxy-2-geranyl-5-pentylphenolate (an anion) and 3-hydroxy-5-pentyl-2-(3-methyl-6-isopropenyl-cyclohex-2-enyl)phenolate (an anion), respectively. Deprotonation produces bicarbonate (conjugate acid) from the carbonate.

Some of the composition is packaged into sachets containing approximately five grams each of the composition. Such packaging is suitable, for example, as a single serving beverage powder and allows for the dispersion of the anion in a beverage. The dispersion of the anion in a beverage increases its surface area, which improves the pharmacokinetics and bioavailability of the first anion and the second anion.

The skilled person will recognize many modifications to the foregoing example, many of which are disclosed in the preceding description and the claims that follow. This disclosure encompasses all combinations of the embodiments of this disclosure that grammar and reason allow.

What is claimed is:

1. A composition, comprising each of a buffer, a conjugate acid, an excipient, an anion, and a solvent at both a concentration by mass and an amount by mole, wherein:

the anion is selected from the group consisting of 3-hydroxy-2-geranyl-5-pentylphenolate, and 3-hydroxy-5-pentyl-2-(3-methyl-6-isopropenylcyclohex-2-enyl) phenolate, and combinations thereof the composition comprises the buffer and the conjugate acid at a combined concentration by mass of at least 0.05 percent and no greater than 2 percent;

the concentration by mass of the excipient in the composition is greater than the combined concentration by mass of the buffer and the conjugate acid in the composition;

the concentration by mass of the solvent in the composition is greater than the concentration by mass of the anion in the composition; the composition comprises the buffer and the conjugate acid at a combined amount by mole that is greater than the amount by mole of the anion in the composition;

the amount by mole of the solvent in the composition is at least 5 times greater than the amount by mole of the anion in the composition; the composition comprises the buffer and the conjugate acid at a ratio by mole of at least 1:800 and no greater than 80:1;

the composition comprises a solid phase at a concentration of at least 88 percent and no greater than 98 percent by mass;

the composition comprises a liquid phase at a concentration of at least 2 percent and no greater than 12 percent by mass;

the solid phase and the liquid phase are in chemical communication such that buffer, conjugate acid, and excipient of the solid phase can dissolve into the liquid phase and such that buffer, conjugate acid, and excipient of the liquid phase can precipitate into the solid phase;

the buffer has a solubility in the liquid phase, which is the maximum mass of the buffer that will dissolve in the liquid phase at thermodynamic equilibrium per volume of the liquid phase;

the conjugate acid has a solubility in the liquid phase, which is the maximum mass of the conjugate acid that will dissolve in the liquid phase at thermodynamic equilibrium per volume of the liquid phase;

the composition comprises one or both of (i) a mass-to-volume ratio of buffer-to-liquid-phase that is greater than the solubility of the buffer in the liquid phase and (ii) a mass-to-volume ratio of conjugate acid-to-liquid-phase that is greater than the solubility of the conjugate acid in the liquid phase;

the excipient has a solubility in the liquid phase, which is the maximum mass of the excipient that will dissolve in the liquid phase at thermodynamic equilibrium per volume of the liquid phase;

the composition comprises a mass-to-volume ratio of excipient-to-liquid-phase that is greater than the solubility of the excipient in the liquid phase;

each of the buffer, the conjugate acid, and the anion have an association constant for protonation in water at 20 degrees Celsius ("Kb,buffer", "Kb, conjugate acid", and "Kb,anion");

the association constant for protonation of the anion is both greater than 10 times the association constant for protonation of the conjugate acid and less than the product of the association constant for protonation of the buffer and the ratio by mole of the buffer and the conjugate acid (10×Kb, conjugate acid<Kb,anion<Kb, buffer×ratio by mole of the buffer and the conjugate acid);

the liquid phase comprises each of the anion and the solvent at both an amount by mass and an amount by mole;

the amount by mass of the solvent in the liquid phase is greater than the amount by mass of the anion in the liquid phase;

the amount by mole of the solvent in the liquid phase is at least 5 times greater than the amount by mole of the anion in the liquid phase; the liquid phase lacks each of the buffer, the conjugate acid, and the excipient at an amount by mole that is greater than the amount by mole of the solvent in the liquid phase;

the solid phase lacks an amount by mass of the anion that is greater than the amount by mass of the anion in the liquid phase;

the solid phase lacks an amount by mass of the solvent that is greater than the amount by mass of the solvent in the liquid phase; the solid phase comprises the excipient at an amount by mass;

the solid phase comprises the buffer and the conjugate acid at a combined amount by mass that is less than the amount by mass of the excipient in the solid phase; and the liquid phase lacks an amount by mass of the excipient that is greater than the amount by mass of the excipient in the solid phase.

2. The composition of claim 1, wherein the buffer is carbonate.

3. The composition of claim 1, wherein the buffer is a carbonate salt.

4. The composition of claim 1, wherein the buffer is sodium carbonate or potassium carbonate.

5. The composition of claim 1, wherein the buffer is phosphate.

6. The composition of claim 1, wherein the buffer is a phosphate salt.

7. The composition of claim 1, wherein the buffer is trisodium phosphate or tripotassium phosphate.

8. The composition of claim 1, comprising the buffer and the conjugate acid at a combined concentration by mass of no greater than 0.2 percent.

9. The composition of claim 1, comprising the buffer and the conjugate acid at a combined concentration by mass of no greater than 0.1 percent.

* * * * *